(12) United States Patent
Opatowsky et al.

(10) Patent No.: US 11,406,682 B2
(45) Date of Patent: Aug. 9, 2022

(54) ROUNDABOUT (ROBO) RECEPTOR INHIBITORS AND USES THEREOF

(71) Applicant: Bar-Ilan University, Ramat-Gan (IL)

(72) Inventors: Yarden Opatowsky, RaAnana (IL); Reut Barak-Fucks, Rehovot (IL); Julia Guez-Haddad, RaAnana (IL); Galit Yom-Tov, Yavne (IL)

(73) Assignee: Bar-Ilan University, Ramat-Gan (IL)

( * ) Notice: Subject to any disclaimer, the term of this patent is extended or adjusted under 35 U.S.C. 154(b) by 0 days.

(21) Appl. No.: 16/641,263

(22) PCT Filed: Aug. 24, 2018

(86) PCT No.: PCT/IL2018/050936
§ 371 (c)(1),
(2) Date: Feb. 24, 2020

(87) PCT Pub. No.: WO2019/038772
PCT Pub. Date: Feb. 28, 2019

(65) Prior Publication Data
US 2020/0353030 A1 Nov. 12, 2020

Related U.S. Application Data

(60) Provisional application No. 62/549,472, filed on Aug. 24, 2017.

(51) Int. Cl.
| | | |
|---|---|---|
| *C07K 16/46* | (2006.01) | |
| *C07K 16/00* | (2006.01) | |
| *A61K 38/10* | (2006.01) | |
| *C07K 9/00* | (2006.01) | |

(52) U.S. Cl.
CPC ............... *A61K 38/10* (2013.01); *C07K 9/00* (2013.01)

(58) Field of Classification Search
None
See application file for complete search history.

(56) References Cited

U.S. PATENT DOCUMENTS

| | | | |
|---|---|---|---|
| 6,861,228 B2 * | 3/2005 | Goodman | G01N 33/68 435/7.1 |
| 7,005,411 B1 | 2/2006 | Goodman et al. | |
| 2006/0141462 A1 | 6/2006 | Reynisdottir et al. | |
| 2009/0092544 A1 | 4/2009 | Iwanari et al. | |
| 2010/0233819 A1 | 9/2010 | Goodman et al. | |
| 2013/0039912 A1 | 2/2013 | Blanche et al. | |
| 2013/0143320 A1 | 6/2013 | Li et al. | |
| 2015/0037325 A1 | 2/2015 | Lu et al. | |
| 2016/0120940 A1 | 5/2016 | Robinson et al. | |
| 2017/0114124 A1 | 4/2017 | Wu et al. | |
| 2017/0281726 A1 | 10/2017 | Robinson et al. | |
| 2020/0157212 A1 * | 5/2020 | Berasi | C07K 16/2803 |

FOREIGN PATENT DOCUMENTS

| | | |
|---|---|---|
| JP | 2015-062367 | 4/2015 |
| WO | WO 2011/128561 | 10/2011 |
| WO | WO 2013/103811 | 7/2013 |
| WO | WO 2019/038772 | 2/2019 |

OTHER PUBLICATIONS

Edwards et al., The remarkable flexibility of the human antibody repertoire; isolation of over one thousand different antibodies to a single protein, BLyS. J Mol Biol. Nov. 14, 2003;334(1): 103-18. (Year: 2003).*
Lloyd et al., Modelling the human immune response: performance of a 1011 human antibody repertoire against a broad panel of therapeutically relevant antigens. Protein Eng Des Sel. Mar. 2009;22(3):159-68. (Year: 2009).*
Goel et al., Plasticity within the antigen-combining site may manifest as molecular mimicry in the humoral immune response. J Immunol. Dec. 15, 2004; 173(12):7358-67. (Year: 2004).*
Kanyavuz et al., Breaking the law: unconventional strategies for antibody diversification. Nat Rev Immunol. Jun. 2019; 19(6):355-368. (Year: 2019).*
Campbell A, General properties and applications of monoclonal antibodies, Elsevier Science Publishers, section 1.1, pp. 1-32, 1984. (Year: 1984).*
Evans and Bashaw. Functional diversity of Robo receptor immunoglobulin domains promotes distinct axon guidance decisions. Curr Biol. Mar. 23, 2010;20(6):567-72. (Year: 2010).*
International Preliminary Report on Patentability dated Mar. 5, 2020 From the International Bureau of WIPO Re. Application No. PCT/IL2018/050936. (8 Pages).
International Search Report and the Written Opinion dated Nov. 8, 2018 From the International Searching Authority Re. Application No. PCT/IL2018/050936. (12 Pages).
Aleksandrova et al. "Robo1 Forms a Compact Dimer-of-Dimers Assembly", Structure, 26(2): 320-328, Feb. 6, 2018.
Ballard et al. "A Roundabout Way to Cancer", Advances in Cancer Research, 114: 187-235, Jan. 2012.
Barak et al. "Crystal Structure of the Extracellular Juxtamembrane Region of Robo1", Journal of Structural Biology, 186(2): 283-235. Available Online Mar. 6, 2014.
Barak et al. "Expression, Derivatization, Crystallization and Experimental Phasing of Art Extracellular Segment of the Human Robo1 Receptor", Acta Crystallographica Section F: Structural Biology and Crystallization Communications, F69(Pt.7): 771-775, Published Online Jun. 28, 2013.
Baumgarten et al. "Roundabout-Like 1 [Exaiptasia Pallida]", Database NCBI [Online], GenBank: KXJ15078.1, Database Accession No. KXJ15078, Feb. 23, 2016.

(Continued)

*Primary Examiner* — Maher M Haddad

(57) ABSTRACT

The present invention, in some embodiments thereof, relates to inhibitory compositions binding to the ectodomain of a Roundabout (Robo) receptor and to the use of same for downregulating Robo-mediated signaling. In particular, the present invention provides moieties that bind to and prevent dimerization of an Ig-like Robo receptor ectodomain, thereby inhibiting Robo receptor activity.

6 Claims, 9 Drawing Sheets
(9 of 9 Drawing Sheet(s) Filed in Color)

Specification includes a Sequence Listing.

(56) References Cited

OTHER PUBLICATIONS

Blockus et al. "Slit-Robo Signaling", Development, 143(17): 3037-3044, Sep. 2016.
Carr et al. "Expression Patterns of Slit and Robo Family Members in Adult Mouse Spinal Cord and Peripheral Nervous System", PLOS One, 12(2): e0172736-1-e0172736-30, Published Online Feb. 24, 2017.
Chang et al. "Activation of Slit2-Robo1 Signaling Promotes Liver Fibrosis", Journal of Hepatology, 63(6): 1413-1420, Published Online Aug. 8, 2015.
Evans et al. "Robo2 Acts in Trans to Inhibit Slit-Robo1 Repulsion in Pre-Crossing Commissural Axons", eLife, 4: e08407-1-e08407-26, Published Online Jul. 17, 2015.
Fukuhara et al. "Structural and Functional Analysis of Slit and Heparin Binding to Immunoglobulin-Like Domains 1 and 2 of *Drosophila* Robo", The Journal of Biological Chemistry, 283(23): 16226-16234, Jun. 6, 2008.
Gara et al. "Slit/Robo Pathway: A Promising Therapeutic Target for Cancer", Drug Discovery Today, 20(1): 156-164, Jan. 2015.
Göhrig et al. "Axon Guidance Factor SLIT1 Inhibits Neural Invasion and Metastasis in Pancreatic Cancer", Cancer Research, 74(5): 1529-1540, Published Online Jan. 21, 2014.
Goodman et al. "Protocadherin Cis-Dimer Architecture and Recognition Unit Diversity ", Proc. Natl. Acad. Sci. USA, PNAS, 114(46): E9829-9837, Published Online Oct. 30, 2017.
Gu et al. "Function of Slit/Robo Signaling in Breast Cancer", Frontiers of Medicine, 9(4): 431-436, Published Online Nov. 5, 2015.
Guez-Haddad et al. "The Neuronal Migration Factor SrGAP2 Achieves Specificity in Ligand Binding Through a Two-Component Molecular Mechanism", Structure, 23(11): 1989-2000, Nov. 3, 2015.
Havlioglu et al. "Slit Proteins, Potential Endogenous Modulators of Inflammation", Journal of Neurovirology, 8(6): 486-495, Dec. 2002.
Hivert et al. "Robo1 and Robo2 Are Homophilic Binding Molecules That Promote Axonal Growth", Molecular and Cellular Neuroscience, 21(4): 534-545, Dec. 2002.
Hohenester "Structural Insight Into Slit-Robo Signalling", Biochemical Society Transactions, 36(2): 271-256, Apr. 1, 2008.
Howitt et al. "Binding Site for Robo Receptors Revealed by Dissection of the Leucine-Rich Repeat Region of Slit", The EMBO Journal, 23(22): 4406-4412, Published Online Oct. 21, 2004.
Huang et al. "The Emerging Role of Slit-Robo Pathway in Gastric and Other Gastro Intestinal Cancers", BMC Cancer, 15(1): 950-1-950-9, Published Online Dec. 16, 2015.
Hussain et al. "A Molecular Mechanism for the Heparan Sulfate Dependence of Slit-Robo Signaling", The Journal of Biological Chemistry, 281(51): 39693-39698, Dec. 22, 2006.
Hwang et al. "Mutations of the SLIT2-ROBO2 Pathway Genes SLIT2 and SRGAP1 Confer Risk for Congenital Anomalies of the Kidney and Urinary Tract", Human Genetics, 134(8): 905-916, Aug. 2015.
Ito et al. "Identification of ROBO1 as a Novel Hepatocellular Carcinoma Antigen and a Potential Therapeutic and Diagnostic Target", Clinical Cancer Research, 12(11): 3257-3264, Jun. 1, 2006.
Jen et al. "RecName: Full=Roundabout Homolog 3; AltName: Full=Roundabout-Like Protein; Flags: Precursor", Database NCBI [Online], UniProtKB/Swiss-Prot: Q96MS0.2, Database Accession No. Q96MS0, Oct. 25, 2017.
Jones et al. "Robo4 Stabilizes the Vascular Network by Inhibiting Pathologic Angiogenesis and Endothelial Hyperpermeability", Nature Medicine, 14(4): 448-453, Apr. 2008.
Jones et al. "Slit2-Robo4 Signalling Promotes Vascular Stability by Blocking Arf6 Activity", Nature Cell Biology, 11(11): 1325-1331, Nov. 2009.
Kidd et al. "RecName: Full=Roundabout Homolog 1; AltName: Full=Deleted in U Twenty Twenty; AltName: Full=H-Robo-1; Flags: Precursor", Database NCBI [Dabase], UniProtKB/Swiss-Prot: Q9Y6N7.1, Database Accession No. Q9Y6N7, Oct. 25, 2017.

Kidd et al. "Roundabout 1 [*Drosophila melanogaster*]", Database NCBI [Online], GenBank: AAC38849.1, Database Accession No. AAC38849, Feb. 5, 1998.
Kidd et al. "Slit Is the Midline Repellent for the Robo Receptor in *Drosophila*", Cell, 96(6): 785-794, Mar. 19, 1999.
Li et al. "Inhibition of Endothelial Slit2/Robo1 Signaling by Thalidomide Restrains Angiogenesis by Blocking the PI3K/Akt Pathway", Digestive Disease and Sciences, 59: 2958-2966, Published Online Oct. 18, 2014.
Liu et al. "Extracellular Ig Domains 1 and 2 of Robo Are Important for Ligand (Slit) Binding", Molecular and Cellular Neuroscience, 26(2): 232-240, Available Online Apr. 16, 2004.
McConnell et al. "A Requirement for Filopodia Extension Toward Slit During Robo-Mediated Axon Repulsion", Journal of Cell Biology, 213(2): 261-274, Published Online Apr. 18, 2016.
Mehlen et al. "Novel Roles for Slits and Netrins: Axon Guidance Cues as Anticancer Targets?", Nature Reviews Cancer, 11(3): 188-197, Published Online Feb. 17, 2011.
Mitsioni et al. "*Homo sapiens* Roundabout Guidance Receptor 2 (ROBO2), Transcript Variant 2, mRNA", Database NCBI [Online], NCBI Reference Sequence: NM_002942.4, Database Accession No. NM_002942, Oct. 2, 2017.
Mitsioni et al. "Roundabout Homolog 2 Isoform ROBO2a [*Homo sapiens*]", Database NCBI [Online], NCBI Reference Sequence: NP_001122401.1, Database Accession No. NP_001122401, Oct. 3, 2017.
Mitsioni et al. "Roundabout Homolog 2 Isoform ROBO2b Precursor [*Homo sapiens*]", Database NCBI [Online], NCBI Reference Sequence: NP_002933.1, Database Accession No. NP_002933, Oct. 2, 2017.
Morlot et al. "Structural Insights Into the Slit-Robo Complex", Proc. Natl. Acad. Sci. USA, PNAS, 104(38): 14923-14928, Sep. 18, 2007.
Mulik et al. "Activation of Endothelial Roundabout Receptor 4 (Robo4) Reduces the Severity of Virus Induced Keratitis", The Journal of Immunology, 186(12): 7195-7204, Jun. 15, 2011.
Nguyen et al. "Diversity and Specificity of Actions of Slit2 Proteolytic Fragments in Axon Guidance" The Journal of Neuroscience, 21(12): 4281-4289, Jun. 15, 2001.
Opatowsky et al. "Structure, Domain Organization, and Different Conformational States of Stem Cell Factor-Induced Intact KIT Dimers", Proc. Natl. Acad. Sci. USA, PNAS, 111(5): 1772-1777, Feb. 4, 2014.
Piper et al. "Signaling Mechanisms Underlying Slit2-Induced Collapse of Xenopus Retinal Growth Cones", Neuron, 49(2): 215-228, Jan. 19, 2006.
Rama et al. "Slit2 Signaling Through Robo1 and Robo2 Is Required for Retinal Neovascularization", Nature Medicine, 21(5): 483-491, May 2015.
Reshetnyak et al. "The Strength and Cooperativity of Contacts in KIT Extracellular Domain Determine Normal Ligand Dependent Stimulation or Oncogenic Activation in Cancer", Molecular Cell, 57(1): 191-201, Jan. 8, 2015.
Seiradake et al. "Structure and Functional Releance of the Slit2 Homodimerization Domain", EMBO Reports, 10(7): 736-741, Published Online Jun. 5, 2009.
Seki et al. "Human ROBO1 Is Cleaved by Metalloproteinases and Gamma-Secretase and Migrates to the Nucleus in Cancer Cells", FEBS Letters, 584(13): 2909-2915, Available Online May 13, 2010.
Sporny et al. "Molecular Symmetry-Constrained Systematic Search Approach to Structure Solution of the Coiled-Coil SRGAP2 F-BARx Domain", Acta Crystallica Section D: Structural Biology, D72(Pt. 12): 1241-1253, Published Online Nov. 29, 2016.
Sulson et al. "Protein Sax-3 [Caenorhabditis Elegans]", Database NCBI [Online], NCBI Reference Sequence: NP_001024990.1, Database Accession No. NP_001024990, Oct. 11, 2017.
Wade et al. "*Homo sapiens* Roundabout, Axon Guidance Receptor, Homolog 2 (*Drosophila*) (ROBO2), Transcript Variant 1, mRNA", Database NCBI [Online], NCBI Reference Sequence: NM_001128929.2, Database Accession No. NM_001128929, Sep. 28, 2013.
Wang et al. "Biochemical Purification of a Mammalian Slit Protein as a Positive Regulator of Sensory Axon Elongation and Branching", Cell, 96(6): 771-784, Mar. 19, 1999.

(56) References Cited

OTHER PUBLICATIONS

Wang et al. "Induction of Tumor Angiogenesis by Slit-Robo Signaling and Inhibition of Cancer Growth by Blocking Robo Activity", Cancer Cell, 4(1): 19-29, Jul. 2003.
Wu et al. "The Neuronal Repellent Slit Inhibits Leukocyte Chemotaxis Induced by Chemotactic Factors", Nature, 410(6831): 948-952, Apr. 19, 2001.
Xiao et al. "Assembly of lamina-Specific Neuronal Connections by Slit Bound to Type IV Collagen", Cell, 146(1): 164-176, Jul. 8, 2011.
Xu et al. "Targeting Skeletal Endothelium to Ameliorate Bone Loss", Nature Medicine, 24(6): 823-833, Published Online May 21, 2018.
Yi et al. "Dynamic Changes in Robo2 and Slit1 Expression in Adult Rat Dorsal Root Ganglion and Sciatic Nerve After Peripheral and Central Axonal Injury", Neuroscience Research, 56(3): 314-321, Available Online Sep. 18, 2006.
Yom-Tov et al. "Robo Ig4 Is a Dimerization Domain", Journal of Molecular Biology, 429(23): 3606-3616, Published Online Oct. 7, 2017.
Yuasa-Kawada et al. "Midline Crossing and Slit Responsiveness of Commissural Axons Require USP33", Nature Neuroscience, 12(9): 1087-1089, Published Online Aug. 16, 2009.
Yue et al. "RecName: Full=Roundabout Homolog 2; Flags: Precursor", Database NCBI [Online], UniProtKB/Swiss-Prot: Q9HCK4.2, Database Accession No. Q9HCK4, Oct. 25, 2017.
Yuen et al. "Slit2-Robo Signaling: A Novel Regulator of Vascular Injury", Current Opinion in Nephrology and Hypertension, 22(4): 445-451, Jul. 2013.
Yuzawa et al. "Structural Basis for Activation of the Receptor Tyrosine Kinase KIT by Stem Cell Factor", Cell, 130(2): 323-334, Jul. 27, 2007.
Zakrys et al. "Roundabout 1 Exists Predominantly as a Basal Dimeric Complex and This Is Uneffected by Binding of the Ligand Slit2", Biochemical Journal 461(1): 61-73, Jul. 2014.
Zhang et al. "Slit2/Robo1 Signaling Promotes Intestinal Tumorigenesis Through Src-Mediated Activation of the Wnt/Beta-Catenin Pathway", Oncotarget, 6(5): 3123-3135, Published Online Dec. 18, 2014.
Zhao et al. "Slit2-Robo1 Signaling Promotes the Adhesion, Invasion and Migration of Tongue Carcinoma Cells via Upregulating Matrix Metalloproteinases 2 and 9, and Downregulating E-Cadherin", Molecular Medicine Reports, 14(3): 1901-1906, Sep. 2016.
Supplementary European Search Report and the European Search Opinion dated Apr. 21, 2021 From the European Patent Office Re. Application No. 18847524.8. (9 Pages).
Abcam "Product Datasheet Anti-Robo2 Antibody AB85278": 4P, XP55495653A, Jan. 2018.
Kanellis et al. "Modulation of Inflammation by Slit Protein In Vivo in Experimental Crescentic Glomerulonephritis", American Journal of Pathology, 165(1):341-352, Jul. 2004.

\* cited by examiner

FIG. 1
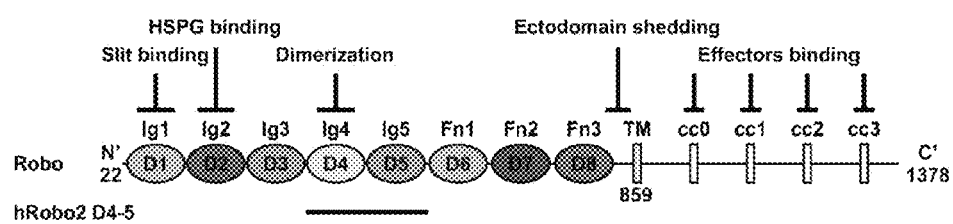
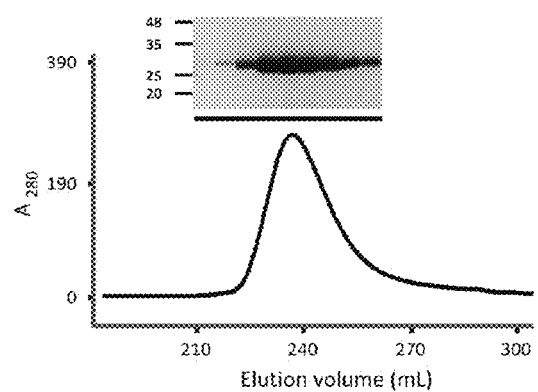
FIG. 2
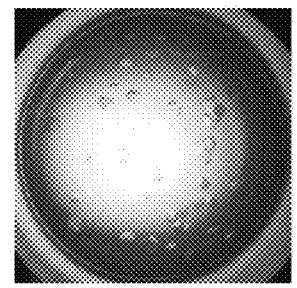
FIG. 3
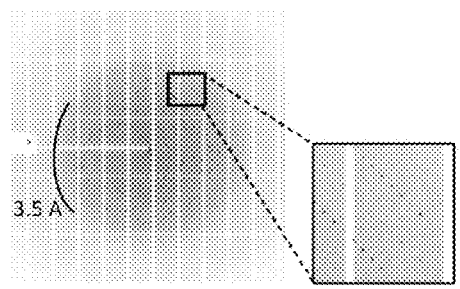
FIG. 4
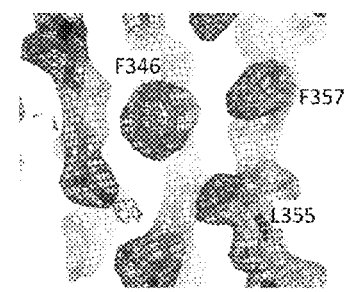
FIG. 5

FIG. 6

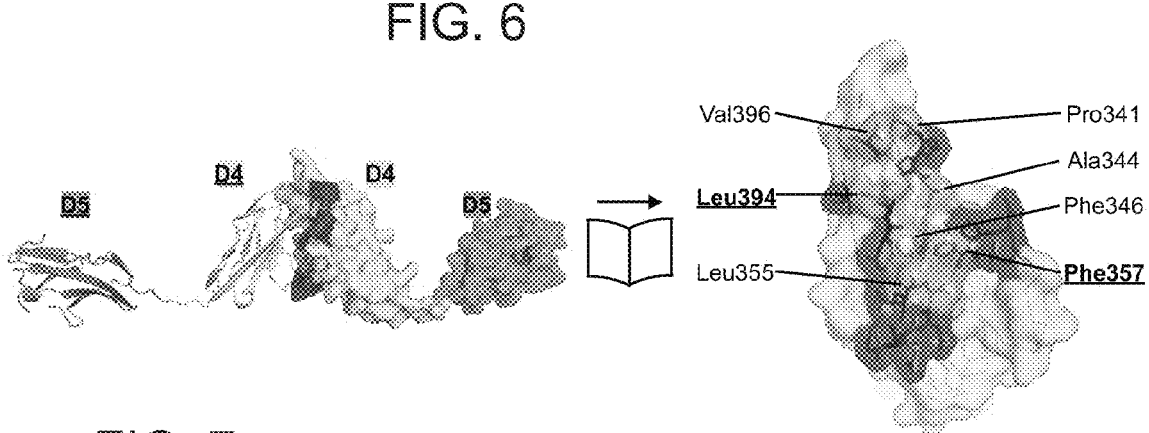

FIG. 7

```
                         320       330       340       350       360
Robo2 Human          308 LTVRAPPQFVVRPRDQIVAQGRTVTFPCETKGNPQPAVFWQKEGSSQNLLPNQPQQPNS
Robo1 Human          345 LTVQEPPHFVVKPRDQVVALGRTVTFQCEATGNPQPAIFWRREGSQNLLESYQPPQSSS
Robo3 Human          341 LSVHVPPQLVTQPQDQMAAPGESVAFQCETKGNPPPAIFWQKEGSQVLLFPSQSLQPTG
Robo1 Drosophila     339 LIVHAPPNFTKRPSNKKVGLNGVVQLPCMASGNPPSVFWTKEGVSTLMFPNSS---HG
SAX-3 C.elegans      311 LRVQAPPSFQTKPADQSVPAGGTATFECTLVGQPSPAYFWSKEGQQDLLFPSYV-SADG
Robo-like Cnidaria   325 PLPQAKPSITMLPKDVIVREGATAKFSCKATGNPLPTVFWDQKSTRQTMFPHQN---NG
                          :  *   :   *  .  . . :  *   *:*  *:  **  ::.   :*    .

380       390       400       410       420
Robo2 Human          367 RCSVSPTGDLTITNIQRSDAGYYICQALTVAGSILAKAQLEVTD-----VLTDRPPPII
Robo1 Human          404 RFSVSQTGDLTITNVQRSDVGYYICQTINVAGSIITKAYLEVTD-----VIADRPPPVI
Robo3 Human          400 RFSVSPRGQLNITAVQRGDAGYYVCQAVSVAGSILAKALLEIKG-----ASLDGLPPVI
Robo1 Drosophila     395 RQYVAADGTLQITDVRQEDEGYYVCSAFSIVDSSTVRVFLQVSS------VDERPPPII
SAX-3 C.elegans      369 RTKVSPTGTLTIEEVRQVDEGAYVCAGINSAGSSLSKAALKVTTKAVTGNTPAKPPPTI
Robo-like Cnidaria   381 RFEVKTXGDLIIKNVQKQDKGEYVCSAFSQAGVETASAMLVVVG-----IL--DTKPTL
                          *   *    *  *   ::: * * *:*    .     . * :        *  * :

430       440       450       460       470
Robo2 Human          421 LQGPANQTLAVDGTALLKCKATGDPLPVISWLKEGFTFPGRDPRATI-QEQGTLQIKNL
Robo1 Human          458 RQGPVNQTVAVDGTFVLSCVATGSPVPTILWRKDGVLVSTQDSRIKQ-LENGVLQIRYA
Robo3 Human          455 LQGPANQTLVLGSSVWLPCRVTGNPQPSVRWKKDGQWLQGDDLQFKT-MANGTLYIANV
Robo1 Drosophila     448 QIGPANQTLPKGSVATLPCRATGNPSPRIKWFHDGHAVQAG-NRYSI-IQGSSLRVDDL
SAX-3 C.elegans      428 EHGHQNQTLMVGSSAILPCQASGKPTPGISWLRDGLPIDITDSRISQ-HSTGSLHIADL
Robo-like Cnidaria   433 KTKPLNQTVNKFEDAIFSCTFDGVPVPSIEWSKGLVLSNSAKYIIKTVGSTSQLKVISS
                         ***:         :   *     *   *  * :           .  *  :

490       500       510
Robo2 Human          479 RISDTGTYTCVATSSSGETSWSAVLDVTESGA
Robo1 Human          516 KLGDTGRYTCIASTPSGEATWSAYIEVQEFGV
Robo3 Human          512 QEMDMGFYSCVAKSSTGEATWSGWLKMREDW-
Robo1 Drosophila     505 QLSDSGTYTCTASGERGETSWAATLTVEKPG-
SAX-3 C.elegans      486 KKPDTGVYTCIAKNEDGESTWSASLTVEDHTS
Robo-like Cnidaria   492 TQNDAGQYECTATNTLGTVKGVVQLTVVDPTT
                          *  *  * .    *       :  :  .

Robo2 Human Q9HCK4
Robo1 Human Q9Y6N7
Robo3 Human Q96MS0
Robo1 Drosophila AAC38849.1
SAX-3 C.elegans NP_001024990.1
Robo-like Cnidaria KXJ15078.1
```

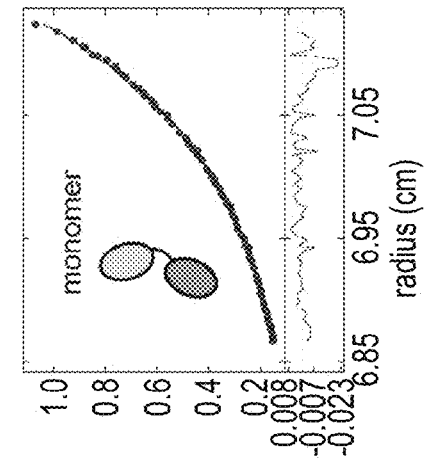
FIG. 8A hRobo2 D4-5 WT
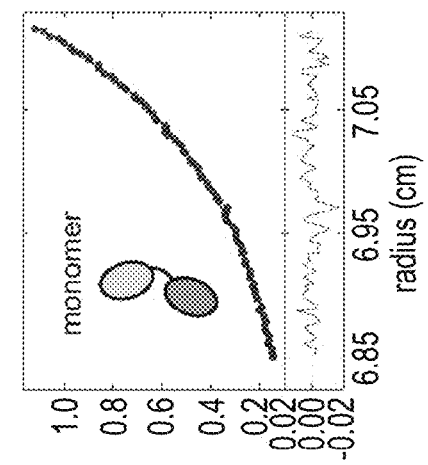
FIG. 8B hRobo2 D4-5 F357R
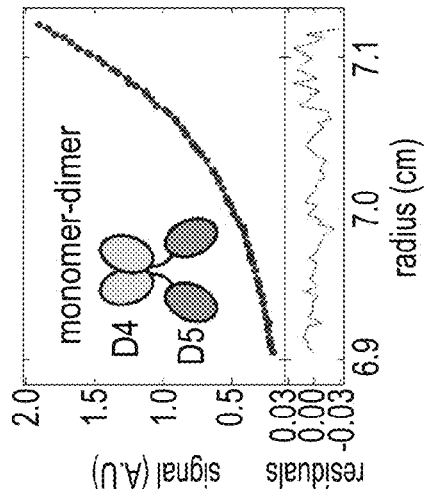
FIG. 8C hRobo2 D4-5 L394R
| construct | molecular weight (Da) polypeptide | molecular weight (Da) glycosylation | total molecular weight (Da) | partial specific volume ($\bar{v}$) | global distribution (Da) sedimentation equilibrium | monomer-dimer equilibrium $K_D$ |
|---|---|---|---|---|---|---|
| hRobo2 D4-5 WT | 24022 | 655 | 24677 | 0.722 | 36299 | 16.9 µM |
| hRobo2 D4-5 F357R | 24031 | 655 | 24686 | 0.722 | 24097 | monomer |
| hRobo2 D4-5 L394R | 24065 | 655 | 24720 | 0.722 | 24692 | monomer |
FIG. 9

FIG. 10A
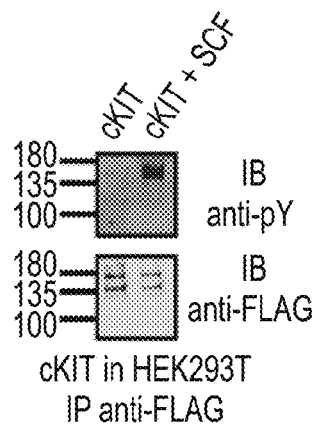 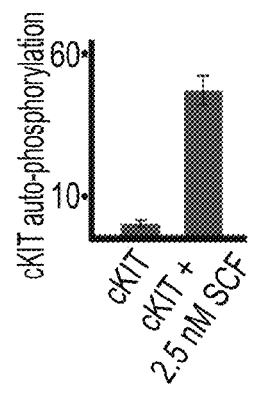 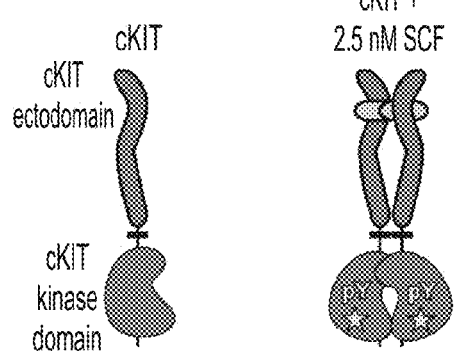
FIG. 10B
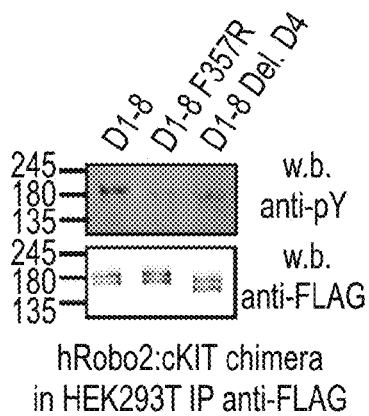 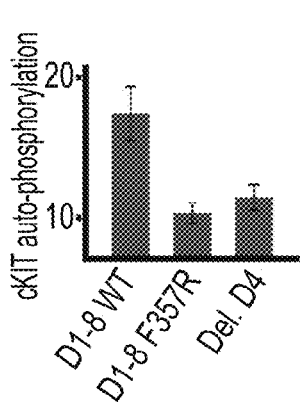 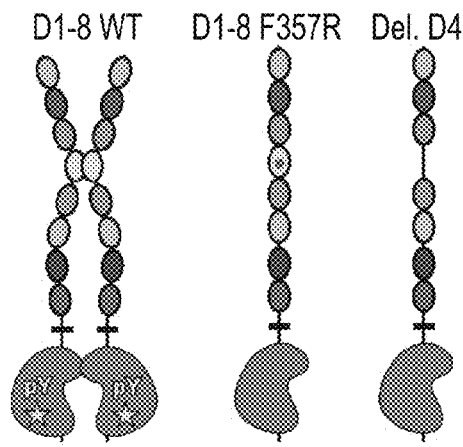
FIG. 10C
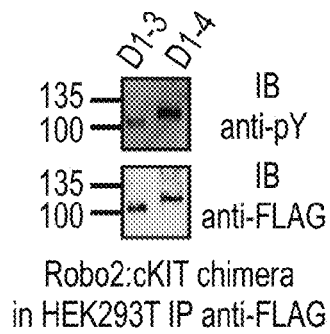 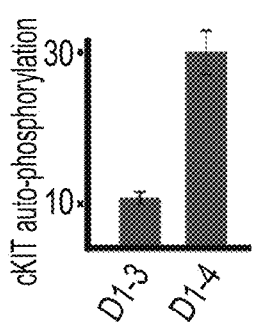 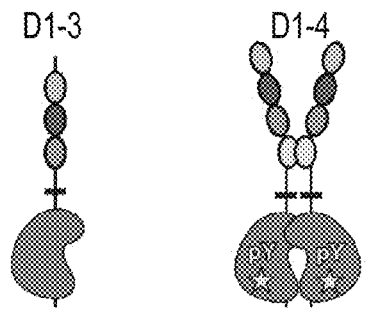

FIG. 10D
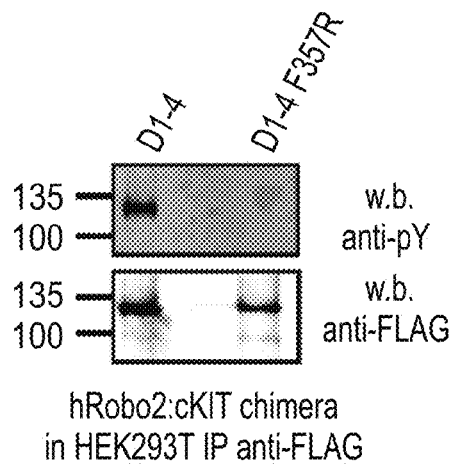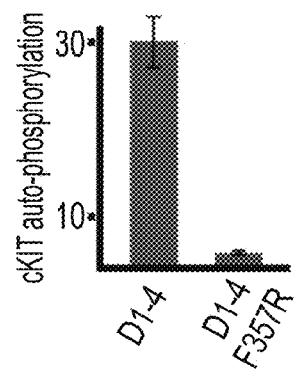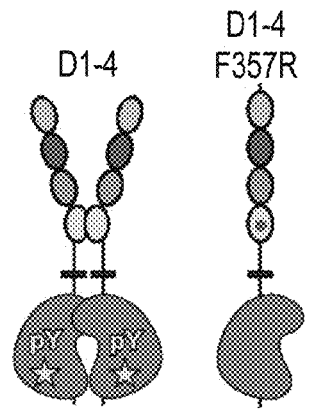
hRobo2:cKIT chimera
in HEK293T IP anti-FLAG
FIG. 10E
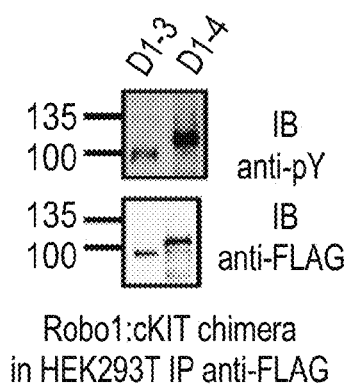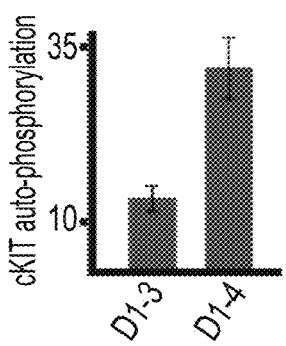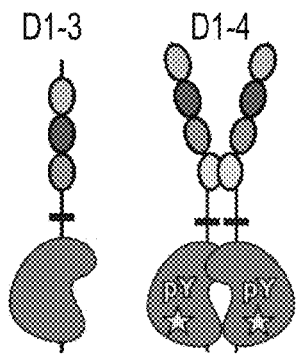
Robo1:cKIT chimera
in HEK293T IP anti-FLAG
FIG. 10F
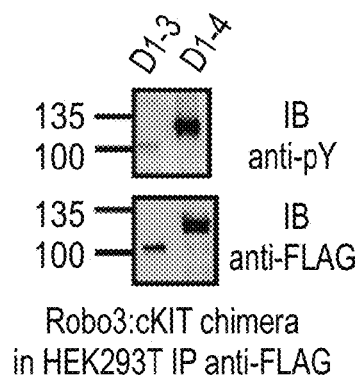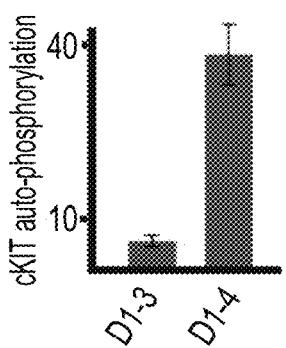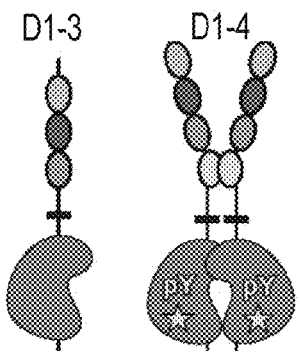
Robo3:cKIT chimera
in HEK293T IP anti-FLAG FIG. 11A
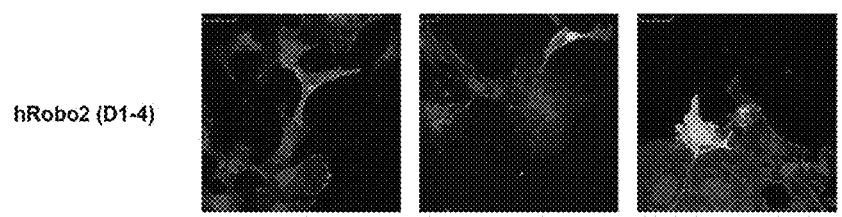
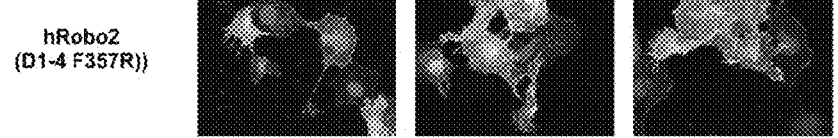
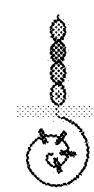
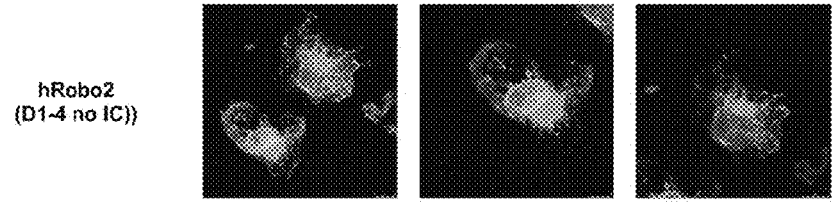

SEQUENCE LISTING

<160> NUMBER OF SEQ ID NOS: 36

<210> SEQ ID NO 1
<211> LENGTH: 1394
<212> TYPE: PRT
<213> ORGANISM: Homo sapiens

<400> SEQUENCE: 1

Met Ala Arg Arg His Glu Arg Val Thr Arg Met Trp Thr Trp Ala
1               5                   10                  15

Pro Gly Leu Leu Met Met Thr Val Val Phe Trp Gly His Gln Gly Asn
            20                  25                  30

Gly Gln Gly Gln Gly Ser Arg Leu Arg Gln Glu Asp Phe Pro Pro Arg

```
             35                  40                  45
Ile Val Glu His Pro Ser Asp Val Ile Val Ser Lys Gly Glu Pro Thr
 50                  55                  60
Thr Leu Asn Cys Lys Ala Glu Gly Arg Pro Thr Pro Thr Ile Glu Trp
 65                  70                  75                  80
Tyr Lys Asp Gly Glu Arg Val Glu Thr Asp Lys Asp Asp Pro Arg Ser
                     85                  90                  95
His Arg Met Leu Leu Pro Ser Gly Ser Leu Phe Phe Leu Arg Ile Val
                100                 105                 110
His Gly Arg Arg Ser Lys Pro Asp Glu Gly Ser Tyr Val Cys Val Ala
            115                 120                 125
Arg Asn Tyr Leu Gly Glu Ala Val Ser Arg Asn Ala Ser Leu Glu Val
130                 135                 140
Ala Leu Leu Arg Asp Asp Phe Arg Gln Asn Pro Thr Asp Val Val Val
145                 150                 155                 160
Ala Ala Gly Glu Pro Ala Ile Leu Glu Cys Gln Pro Pro Arg Gly His
                165                 170                 175
Pro Glu Pro Thr Ile Tyr Trp Lys Lys Asp Lys Val Arg Ile Asp Asp
                180                 185                 190
Lys Glu Glu Arg Ile Ser Ile Arg Gly Gly Lys Leu Met Ile Ser Asn
            195                 200                 205
Thr Arg Lys Ser Asp Ala Gly Met Tyr Thr Cys Val Gly Thr Asn Met
210                 215                 220
Val Gly Glu Arg Asp Ser Asp Pro Ala Glu Leu Thr Val Phe Glu Arg
225                 230                 235                 240
Pro Thr Phe Leu Arg Arg Pro Ile Asn Gln Val Val Leu Glu Glu Glu
                245                 250                 255
Ala Val Glu Phe Arg Cys Gln Val Gln Gly Asp Pro Gln Pro Thr Val
                260                 265                 270
Arg Trp Lys Lys Asp Asp Ala Asp Leu Pro Arg Gly Arg Tyr Asp Ile
            275                 280                 285
Lys Asp Asp Tyr Thr Leu Arg Ile Lys Lys Thr Met Ser Thr Asp Glu
290                 295                 300
Gly Thr Tyr Met Cys Ile Ala Glu Asn Arg Val Gly Lys Met Glu Ala
305                 310                 315                 320
Ser Ala Thr Leu Thr Val Arg Ala Pro Pro Gln Phe Val Val Arg Pro
                325                 330                 335
Arg Asp Gln Ile Val Ala Gln Gly Arg Thr Val Thr Phe Pro Cys Glu
                340                 345                 350
Thr Lys Gly Asn Pro Gln Pro Ala Val Phe Trp Gln Lys Glu Gly Ser
            355                 360                 365
Gln Asn Leu Leu Phe Pro Asn Gln Pro Gln Gln Pro Asn Ser Arg Cys
            370                 375                 380
Ser Val Ser Pro Thr Gly Asp Leu Thr Ile Thr Asn Ile Gln Arg Ser
385                 390                 395                 400
Asp Ala Gly Tyr Tyr Ile Cys Gln Ala Leu Thr Val Ala Gly Ser Ile
                405                 410                 415
Leu Ala Lys Ala Gln Leu Glu Val Thr Asp Val Leu Thr Asp Arg Pro
            420                 425                 430
Pro Pro Ile Ile Leu Gln Gly Pro Ala Asn Gln Thr Leu Ala Val Asp
            435                 440                 445
Gly Thr Ala Leu Leu Lys Cys Lys Ala Thr Gly Asp Pro Leu Pro Val
450                 455                 460
```

-continued

```
Ile Ser Trp Leu Lys Glu Gly Phe Thr Phe Pro Gly Arg Asp Pro Arg
465                 470                 475                 480

Ala Thr Ile Gln Glu Gln Gly Thr Leu Gln Ile Lys Asn Leu Arg Ile
                485                 490                 495

Ser Asp Thr Gly Thr Tyr Thr Cys Val Ala Thr Ser Ser Ser Gly Glu
            500                 505                 510

Thr Ser Trp Ser Ala Val Leu Asp Val Thr Glu Ser Gly Ala Thr Ile
        515                 520                 525

Ser Lys Asn Tyr Asp Leu Ser Asp Leu Pro Gly Pro Pro Ser Lys Pro
    530                 535                 540

Gln Val Thr Asp Val Thr Lys Asn Ser Val Thr Leu Ser Trp Gln Pro
545                 550                 555                 560

Gly Thr Pro Gly Thr Leu Pro Ala Ser Ala Tyr Ile Ile Glu Ala Phe
                565                 570                 575

Ser Gln Ser Val Ser Asn Ser Trp Gln Thr Val Ala Asn His Val Lys
            580                 585                 590

Thr Thr Leu Tyr Thr Val Arg Gly Leu Arg Pro Asn Thr Ile Tyr Leu
        595                 600                 605

Phe Met Val Arg Ala Ile Asn Pro Gln Gly Leu Ser Asp Pro Ser Pro
610                 615                 620

Met Ser Asp Pro Val Arg Thr Gln Asp Ile Ser Pro Pro Ala Gln Gly
625                 630                 635                 640

Val Asp His Arg Gln Val Gln Lys Glu Leu Gly Asp Val Leu Val Arg
                645                 650                 655

Leu His Asn Pro Val Val Leu Thr Pro Thr Thr Val Gln Val Thr Trp
            660                 665                 670

Thr Val Asp Arg Gln Pro Gln Phe Ile Gln Gly Tyr Arg Val Met Tyr
        675                 680                 685

Arg Gln Thr Ser Gly Leu Gln Ala Thr Ser Ser Trp Gln Asn Leu Asp
    690                 695                 700

Ala Lys Val Pro Thr Glu Arg Ser Ala Val Leu Val Asn Leu Lys Lys
705                 710                 715                 720

Gly Val Thr Tyr Glu Ile Lys Val Arg Pro Tyr Phe Asn Glu Phe Gln
                725                 730                 735

Gly Met Asp Ser Glu Ser Lys Thr Val Arg Thr Thr Glu Glu Ala Pro
            740                 745                 750

Ser Ala Pro Pro Gln Ser Val Thr Val Leu Thr Val Gly Ser Tyr Asn
        755                 760                 765

Ser Thr Ser Ile Ser Val Ser Trp Asp Pro Pro Pro Asp His Gln
    770                 775                 780

Asn Gly Ile Ile Gln Glu Tyr Lys Ile Trp Cys Leu Gly Asn Glu Thr
785                 790                 795                 800

Arg Phe His Ile Asn Lys Thr Val Asp Ala Ala Ile Arg Ser Val Ile
                805                 810                 815

Ile Gly Gly Leu Phe Pro Gly Ile Gln Tyr Arg Val Glu Val Ala Ala
            820                 825                 830

Ser Thr Ser Ala Gly Val Gly Val Lys Ser Glu Pro Gln Pro Ile Ile
        835                 840                 845

Ile Gly Arg Arg Asn Glu Val Val Ile Thr Glu Asn Asn Asn Ser Ile
    850                 855                 860

Thr Glu Gln Ile Thr Asp Val Val Lys Gln Pro Ala Phe Ile Ala Gly
865                 870                 875                 880
```

Ile Gly Gly Ala Cys Trp Val Ile Leu Met Gly Phe Ser Ile Trp Leu
            885                 890                 895

Tyr Trp Arg Arg Lys Lys Arg Lys Gly Leu Ser Asn Tyr Ala Val Thr
        900                 905                 910

Phe Gln Arg Gly Asp Gly Gly Leu Met Ser Asn Gly Ser Arg Pro Gly
        915                 920                 925

Leu Leu Asn Ala Gly Asp Pro Ser Tyr Pro Trp Leu Ala Asp Ser Trp
    930                 935                 940

Pro Ala Thr Ser Leu Pro Val Asn Asn Ser Asn Ser Gly Pro Asn Glu
945                 950                 955                 960

Ile Gly Asn Phe Gly Arg Gly Asp Val Leu Pro Pro Val Pro Gly Gln
            965                 970                 975

Gly Asp Lys Thr Ala Thr Met Leu Ser Asp Gly Ala Ile Tyr Ser Ser
            980                 985                 990

Ile Asp Phe Thr Thr Lys Thr Ser Tyr Asn Ser Ser Ser Gln Ile Thr
        995                 1000                1005

Gln Ala Thr Pro Tyr Ala Thr Thr Gln Ile Leu His Ser Asn Ser
    1010                1015                1020

Ile His Glu Leu Ala Val Asp Leu Pro Asp Pro Gln Trp Lys Ser
    1025                1030                1035

Ser Ile Gln Gln Lys Thr Asp Leu Met Gly Phe Gly Tyr Ser Leu
    1040                1045                1050

Pro Asp Gln Asn Lys Gly Asn Asn Gly Gly Lys Gly Gly Lys Lys
    1055                1060                1065

Lys Lys Asn Lys Asn Ser Ser Lys Pro Gln Lys Asn Asn Gly Ser
    1070                1075                1080

Thr Trp Ala Asn Val Pro Leu Pro Pro Pro Val Gln Pro Leu
    1085                1090                1095

Pro Gly Thr Glu Leu Glu His Tyr Ala Val Glu Gln Gln Glu Asn
    1100                1105                1110

Gly Tyr Asp Ser Asp Ser Trp Cys Pro Pro Leu Pro Val Gln Thr
    1115                1120                1125

Tyr Leu His Gln Gly Leu Glu Asp Glu Leu Glu Glu Asp Asp Asp
    1130                1135                1140

Arg Val Pro Thr Pro Pro Val Arg Gly Val Ala Ser Ser Pro Ala
    1145                1150                1155

Ile Ser Phe Gly Gln Gln Ser Thr Ala Thr Leu Thr Pro Ser Pro
    1160                1165                1170

Arg Glu Glu Met Gln Pro Met Leu Gln Ala His Leu Asp Glu Leu
    1175                1180                1185

Thr Arg Ala Tyr Gln Phe Asp Ile Ala Lys Gln Thr Trp His Ile
    1190                1195                1200

Gln Ser Asn Asn Gln Pro Pro Gln Pro Pro Val Pro Pro Leu Gly
    1205                1210                1215

Tyr Val Ser Gly Ala Leu Ile Ser Asp Leu Glu Thr Asp Val Ala
    1220                1225                1230

Asp Asp Asp Ala Asp Asp Glu Glu Glu Ala Leu Glu Ile Pro Arg
    1235                1240                1245

Pro Leu Arg Ala Leu Asp Gln Thr Pro Gly Ser Ser Met Asp Asn
    1250                1255                1260

Leu Asp Ser Ser Val Thr Gly Lys Ala Phe Thr Ser Ser Gln Arg
    1265                1270                1275

Pro Arg Pro Thr Ser Pro Phe Ser Thr Asp Ser Asn Thr Ser Ala

```
              1280                1285                1290

Ala Leu Ser Gln Ser Gln Arg Pro Arg Pro Thr Lys Lys His Lys
        1295                1300                1305

Gly Gly Arg Met Asp Gln Gln Pro Ala Leu Pro His Arg Arg Glu
        1310                1315                1320

Gly Met Thr Asp Glu Glu Ala Leu Val Pro Tyr Ser Lys Pro Ser
        1325                1330                1335

Phe Pro Ser Pro Gly Gly His Ser Ser Ser Gly Thr Ala Ser Ser
        1340                1345                1350

Lys Gly Ser Thr Gly Pro Arg Lys Thr Glu Val Leu Arg Ala Gly
        1355                1360                1365

His Gln Arg Asn Ala Ser Asp Leu Leu Asp Ile Gly Tyr Met Gly
        1370                1375                1380

Ser Asn Ser Gln Gly Gln Phe Thr Gly Glu Leu
        1385                1390

<210> SEQ ID NO 2
<211> LENGTH: 1378
<212> TYPE: PRT
<213> ORGANISM: Homo sapiens

<400> SEQUENCE: 2

Met Ser Leu Leu Met Phe Thr Gln Leu Leu Cys Gly Phe Leu Tyr
1               5                   10                  15

Val Arg Val Asp Gly Ser Arg Leu Arg Gln Glu Asp Phe Pro Pro Arg
                20                  25                  30

Ile Val Glu His Pro Ser Asp Val Ile Val Ser Lys Gly Glu Pro Thr
            35                  40                  45

Thr Leu Asn Cys Lys Ala Glu Gly Arg Pro Thr Pro Thr Ile Glu Trp
    50                  55                  60

Tyr Lys Asp Gly Glu Arg Val Glu Thr Asp Lys Asp Asp Pro Arg Ser
65                  70                  75                  80

His Arg Met Leu Leu Pro Ser Gly Ser Leu Phe Phe Leu Arg Ile Val
                85                  90                  95

His Gly Arg Arg Ser Lys Pro Asp Glu Gly Ser Tyr Val Cys Val Ala
            100                 105                 110

Arg Asn Tyr Leu Gly Glu Ala Val Ser Arg Asn Ala Ser Leu Glu Val
        115                 120                 125

Ala Leu Leu Arg Asp Asp Phe Arg Gln Asn Pro Thr Asp Val Val Val
    130                 135                 140

Ala Ala Gly Glu Pro Ala Ile Leu Glu Cys Gln Pro Pro Arg Gly His
145                 150                 155                 160

Pro Glu Pro Thr Ile Tyr Trp Lys Lys Asp Lys Val Arg Ile Asp Asp
                165                 170                 175

Lys Glu Glu Arg Ile Ser Ile Arg Gly Gly Lys Leu Met Ile Ser Asn
            180                 185                 190

Thr Arg Lys Ser Asp Ala Gly Met Tyr Thr Cys Val Gly Thr Asn Met
        195                 200                 205

Val Gly Glu Arg Asp Ser Asp Pro Ala Glu Leu Thr Val Phe Glu Arg
    210                 215                 220

Pro Thr Phe Leu Arg Arg Pro Ile Asn Gln Val Val Leu Glu Glu Glu
225                 230                 235                 240

Ala Val Glu Phe Arg Cys Gln Val Gln Gly Asp Pro Gln Pro Thr Val
                245                 250                 255
```

```
Arg Trp Lys Lys Asp Asp Ala Asp Leu Pro Arg Gly Arg Tyr Asp Ile
            260                 265                 270

Lys Asp Asp Tyr Thr Leu Arg Ile Lys Lys Thr Met Ser Thr Asp Glu
        275                 280                 285

Gly Thr Tyr Met Cys Ile Ala Glu Asn Arg Val Gly Lys Met Glu Ala
        290                 295                 300

Ser Ala Thr Leu Thr Val Arg Ala Pro Pro Gln Phe Val Val Arg Pro
305                 310                 315                 320

Arg Asp Gln Ile Val Ala Gln Gly Arg Thr Val Thr Phe Pro Cys Glu
                325                 330                 335

Thr Lys Gly Asn Pro Gln Pro Ala Val Phe Trp Gln Lys Glu Gly Ser
            340                 345                 350

Gln Asn Leu Leu Phe Pro Asn Gln Pro Gln Gln Pro Asn Ser Arg Cys
            355                 360                 365

Ser Val Ser Pro Thr Gly Asp Leu Thr Ile Thr Asn Ile Gln Arg Ser
            370                 375                 380

Asp Ala Gly Tyr Tyr Ile Cys Gln Ala Leu Thr Val Ala Gly Ser Ile
385                 390                 395                 400

Leu Ala Lys Ala Gln Leu Glu Val Thr Asp Val Leu Thr Asp Arg Pro
                405                 410                 415

Pro Pro Ile Ile Leu Gln Gly Pro Ala Asn Gln Thr Leu Ala Val Asp
            420                 425                 430

Gly Thr Ala Leu Leu Lys Cys Lys Ala Thr Gly Asp Pro Leu Pro Val
            435                 440                 445

Ile Ser Trp Leu Lys Glu Gly Phe Thr Phe Pro Gly Arg Asp Pro Arg
450                 455                 460

Ala Thr Ile Gln Glu Gln Gly Thr Leu Gln Ile Lys Asn Leu Arg Ile
465                 470                 475                 480

Ser Asp Thr Gly Thr Tyr Thr Cys Val Ala Thr Ser Ser Ser Gly Glu
                485                 490                 495

Thr Ser Trp Ser Ala Val Leu Asp Val Thr Glu Ser Gly Ala Thr Ile
            500                 505                 510

Ser Lys Asn Tyr Asp Leu Ser Asp Leu Pro Gly Pro Pro Ser Lys Pro
            515                 520                 525

Gln Val Thr Asp Val Thr Lys Asn Ser Val Thr Leu Ser Trp Gln Pro
            530                 535                 540

Gly Thr Pro Gly Thr Leu Pro Ala Ser Ala Tyr Ile Ile Glu Ala Phe
545                 550                 555                 560

Ser Gln Ser Val Ser Asn Ser Trp Gln Thr Val Ala Asn His Val Lys
                565                 570                 575

Thr Thr Leu Tyr Thr Val Arg Gly Leu Arg Pro Asn Thr Ile Tyr Leu
            580                 585                 590

Phe Met Val Arg Ala Ile Asn Pro Gln Gly Leu Ser Asp Pro Ser Pro
            595                 600                 605

Met Ser Asp Pro Val Arg Thr Gln Asp Ile Ser Pro Pro Ala Gln Gly
            610                 615                 620

Val Asp His Arg Gln Val Gln Lys Glu Leu Gly Asp Val Leu Val Arg
625                 630                 635                 640

Leu His Asn Pro Val Val Leu Thr Pro Thr Thr Val Gln Val Thr Trp
                645                 650                 655

Thr Val Asp Arg Gln Pro Gln Phe Ile Gln Gly Tyr Arg Val Met Tyr
            660                 665                 670

Arg Gln Thr Ser Gly Leu Gln Ala Thr Ser Ser Trp Gln Asn Leu Asp
```

-continued

```
            675                 680                 685
Ala Lys Val Pro Thr Glu Arg Ser Ala Val Leu Val Asn Leu Lys Lys
        690                 695                 700

Gly Val Thr Tyr Glu Ile Lys Val Arg Pro Tyr Phe Asn Glu Phe Gln
705                 710                 715                 720

Gly Met Asp Ser Glu Ser Lys Thr Val Arg Thr Thr Glu Glu Ala Pro
        725                 730                 735

Ser Ala Pro Pro Gln Ser Val Thr Val Leu Thr Val Gly Ser Tyr Asn
            740                 745                 750

Ser Thr Ser Ile Ser Val Ser Trp Asp Pro Pro Pro Asp His Gln
        755                 760                 765

Asn Gly Ile Ile Gln Glu Tyr Lys Ile Trp Cys Leu Gly Asn Glu Thr
        770                 775                 780

Arg Phe His Ile Asn Lys Thr Val Asp Ala Ala Ile Arg Ser Val Ile
785                 790                 795                 800

Ile Gly Gly Leu Phe Pro Gly Ile Gln Tyr Arg Val Glu Val Ala Ala
                    805                 810                 815

Ser Thr Ser Ala Gly Val Gly Val Lys Ser Glu Pro Gln Pro Ile Ile
                820                 825                 830

Ile Gly Arg Arg Asn Glu Val Val Ile Thr Glu Asn Asn Ser Ile
        835                 840                 845

Thr Glu Gln Ile Thr Asp Val Val Lys Gln Pro Ala Phe Ile Ala Gly
850                 855                 860

Ile Gly Gly Ala Cys Trp Val Ile Leu Met Gly Phe Ser Ile Trp Leu
865                 870                 875                 880

Tyr Trp Arg Arg Lys Lys Arg Lys Gly Leu Ser Asn Tyr Ala Val Thr
                    885                 890                 895

Phe Gln Arg Gly Asp Gly Gly Leu Met Ser Asn Gly Ser Arg Pro Gly
                900                 905                 910

Leu Leu Asn Ala Gly Asp Pro Ser Tyr Pro Trp Leu Ala Asp Ser Trp
        915                 920                 925

Pro Ala Thr Ser Leu Pro Val Asn Asn Ser Asn Ser Gly Pro Asn Glu
930                 935                 940

Ile Gly Asn Phe Gly Arg Gly Asp Val Leu Pro Pro Val Pro Gly Gln
945                 950                 955                 960

Gly Asp Lys Thr Ala Thr Met Leu Ser Asp Gly Ala Ile Tyr Ser Ser
                965                 970                 975

Ile Asp Phe Thr Thr Lys Thr Ser Tyr Asn Ser Ser Ser Gln Ile Thr
                980                 985                 990

Gln Ala Thr Pro Tyr Ala Thr Thr Gln Ile Leu His Ser Asn Ser Ile
        995                 1000                1005

His Glu Leu Ala Val Asp Leu Pro Asp Pro Gln Trp Lys Ser Ser
        1010                1015                1020

Ile Gln Gln Lys Thr Asp Leu Met Gly Phe Gly Tyr Ser Leu Pro
        1025                1030                1035

Asp Gln Asn Lys Gly Asn Asn Gly Gly Lys Gly Lys Lys Lys
        1040                1045                1050

Lys Asn Lys Asn Ser Ser Lys Pro Gln Lys Asn Asn Gly Ser Thr
        1055                1060                1065

Trp Ala Asn Val Pro Leu Pro Pro Pro Val Gln Pro Leu Pro
        1070                1075                1080

Gly Thr Glu Leu Glu His Tyr Ala Val Glu Gln Gln Glu Asn Gly
        1085                1090                1095
```

Tyr Asp Ser Asp Ser Trp Cys Pro Pro Leu Pro Val Gln Thr Tyr
1100                1105                1110

Leu His Gln Gly Leu Glu Asp Glu Leu Glu Glu Asp Asp Asp Arg
1115                1120                1125

Val Pro Thr Pro Pro Val Arg Gly Val Ala Ser Ser Pro Ala Ile
1130                1135                1140

Ser Phe Gly Gln Gln Ser Thr Ala Thr Leu Thr Pro Ser Pro Arg
1145                1150                1155

Glu Glu Met Gln Pro Met Leu Gln Ala His Leu Asp Glu Leu Thr
1160                1165                1170

Arg Ala Tyr Gln Phe Asp Ile Ala Lys Gln Thr Trp His Ile Gln
1175                1180                1185

Ser Asn Asn Gln Pro Pro Gln Pro Pro Val Pro Pro Leu Gly Tyr
1190                1195                1200

Val Ser Gly Ala Leu Ile Ser Asp Leu Glu Thr Asp Val Ala Asp
1205                1210                1215

Asp Asp Ala Asp Asp Glu Glu Glu Ala Leu Glu Ile Pro Arg Pro
1220                1225                1230

Leu Arg Ala Leu Asp Gln Thr Pro Gly Ser Ser Met Asp Asn Leu
1235                1240                1245

Asp Ser Ser Val Thr Gly Lys Ala Phe Thr Ser Ser Gln Arg Pro
1250                1255                1260

Arg Pro Thr Ser Pro Phe Ser Thr Asp Ser Asn Thr Ser Ala Ala
1265                1270                1275

Leu Ser Gln Ser Gln Arg Pro Arg Pro Thr Lys Lys His Lys Gly
1280                1285                1290

Gly Arg Met Asp Gln Gln Pro Ala Leu Pro His Arg Arg Glu Gly
1295                1300                1305

Met Thr Asp Glu Glu Ala Leu Val Pro Tyr Ser Lys Pro Ser Phe
1310                1315                1320

Pro Ser Pro Gly Gly His Ser Ser Ser Gly Thr Ala Ser Ser Lys
1325                1330                1335

Gly Ser Thr Gly Pro Arg Lys Thr Glu Val Leu Arg Ala Gly His
1340                1345                1350

Gln Arg Asn Ala Ser Asp Leu Leu Asp Ile Gly Tyr Met Gly Ser
1355                1360                1365

Asn Ser Gln Gly Gln Phe Thr Gly Glu Leu
1370                1375

<210> SEQ ID NO 3
<211> LENGTH: 279
<212> TYPE: PRT
<213> ORGANISM: Artificial sequence
<220> FEATURE:
<223> OTHER INFORMATION: Amino acid sequence of Fd chain of AbD32836.1

<400> SEQUENCE: 3

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ala Leu Ser Trp Val Arg Gln Ala Pro Gly Lys Gly Leu Glu Trp Val
            35                  40                  45

Gly His Ile Lys Ser Lys Thr Asp Gly Gly Ala Thr Glu Tyr Ala Ala
        50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Ser Tyr Ser Glu Tyr Ile Pro Leu Tyr Ala Phe Ala
            100                 105                 110

Val Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
210                 215                 220

Lys Ser Glu Phe Gly Gly Ala Pro Gly Lys Pro Ile Pro Asn Pro Leu
225                 230                 235                 240

Leu Gly Leu Asp Ser Thr Asp Ala Pro Ser Ala Trp Ser His Pro Gln
            245                 250                 255

Phe Glu Lys Gly Gly Gly Ser Gly Gly Ser Gly Ser Ala Trp
            260                 265                 270

Ser His Pro Gln Phe Glu Lys
        275

<210> SEQ ID NO 4
<211> LENGTH: 215
<212> TYPE: PRT
<213> ORGANISM: Artificial sequence
<220> FEATURE:
<223> OTHER INFORMATION: AbD32836.1 Amino acid sequence of light chain

<400> SEQUENCE: 4

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Ser Lys
            20                  25                  30

Tyr Val Ser Trp Tyr Gln Gln Leu Pro Gly Thr Ala Pro Lys Leu Leu
        35                  40                  45

Ile Tyr Tyr Thr Ser Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Tyr Ala Trp Asp Ser Thr Ser
                85                  90                  95

Thr Ser Thr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

```
Pro Gly Ala Val Thr Val Ala Trp Lys Ala Asp Ser Ser Pro Val Lys
145                 150                 155                 160

Ala Gly Val Glu Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Ala
    210                 215

<210> SEQ ID NO 5
<211> LENGTH: 5
<212> TYPE: PRT
<213> ORGANISM: Artificial sequence
<220> FEATURE:
<223> OTHER INFORMATION: Heavy Chain CDRs

<400> SEQUENCE: 5

Ser Tyr Ala Leu Ser
1               5

<210> SEQ ID NO 6
<211> LENGTH: 19
<212> TYPE: PRT
<213> ORGANISM: Artificial sequence
<220> FEATURE:
<223> OTHER INFORMATION: Heavy Chain CDRs

<400> SEQUENCE: 6

His Ile Lys Ser Lys Thr Asp Gly Gly Ala Thr Glu Tyr Ala Ala Pro
1               5                   10                  15

Val Lys Gly

<210> SEQ ID NO 7
<211> LENGTH: 13
<212> TYPE: PRT
<213> ORGANISM: Artificial sequence
<220> FEATURE:
<223> OTHER INFORMATION: Heavy Chain CDRs

<400> SEQUENCE: 7

Ser Tyr Ser Glu Tyr Ile Pro Leu Tyr Ala Phe Ala Val
1               5                   10

<210> SEQ ID NO 8
<211> LENGTH: 13
<212> TYPE: PRT
<213> ORGANISM: Artificial sequence
<220> FEATURE:
<223> OTHER INFORMATION: Light Chain CDR

<400> SEQUENCE: 8

Ser Gly Ser Ser Ser Asn Ile Gly Ser Lys Tyr Val Ser
1               5                   10

<210> SEQ ID NO 9
<211> LENGTH: 7
<212> TYPE: PRT
<213> ORGANISM: Artificial sequence
<220> FEATURE:
<223> OTHER INFORMATION: Light Chain CDR

<400> SEQUENCE: 9
```

Tyr Thr Ser Gln Arg Pro Ser
1               5

<210> SEQ ID NO 10
<211> LENGTH: 11
<212> TYPE: PRT
<213> ORGANISM: Artificial sequence
<220> FEATURE:
<223> OTHER INFORMATION: Light Chain CDR

<400> SEQUENCE: 10

Tyr Ala Trp Asp Ser Thr Ser Thr Val
1               5                   10

<210> SEQ ID NO 11
<211> LENGTH: 103
<212> TYPE: PRT
<213> ORGANISM: Artificial sequence
<220> FEATURE:
<223> OTHER INFORMATION: CL amino acid sequence

<400> SEQUENCE: 11

Pro Lys Ala Ala Pro Ser Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Ser Ser Pro Val Lys
        35                  40                  45

Ala Gly Val Glu Thr Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Ala
            100

<210> SEQ ID NO 12
<211> LENGTH: 102
<212> TYPE: PRT
<213> ORGANISM: Artificial sequence
<220> FEATURE:
<223> OTHER INFORMATION: CH1 amino acid sequence

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser
            100

```
<210> SEQ ID NO 13
<211> LENGTH: 2730
<212> TYPE: PRT
<213> ORGANISM: Drosophila melanogaster

<400> SEQUENCE: 13

Met His Pro Met His Pro Glu Asn His Ala Ile Ala Arg Ser Thr Ser
1               5                   10                  15

Thr Thr Asn Asn Pro Ser Arg Ser Arg Ser Arg Met Trp Leu Leu
            20                  25                  30

Pro Ala Trp Leu Leu Leu Val Leu Val Ala Ser Asn Gly Leu Pro Ala
            35                  40                  45

Val Arg Gly Gln Tyr Gln Ser Pro Arg Ile Ile Glu His Pro Thr Asp
50                  55                  60

Leu Val Val Lys Lys Asn Glu Pro Ala Thr Leu Asn Cys Lys Val Glu
65                  70                  75                  80

Gly Lys Pro Glu Pro Thr Ile Glu Trp Phe Lys Asp Gly Glu Pro Val
                85                  90                  95

Ser Thr Asn Glu Lys Lys Ser His Arg Val Gln Phe Lys Asp Gly Ala
            100                 105                 110

Leu Phe Phe Tyr Arg Thr Met Gln Gly Lys Lys Glu Gln Asp Gly Gly
            115                 120                 125

Glu Tyr Trp Cys Val Ala Lys Asn Arg Val Gly Gln Ala Val Ser Arg
130                 135                 140

His Ala Ser Leu Gln Ile Ala Val Leu Arg Asp Asp Phe Arg Val Glu
145                 150                 155                 160

Pro Lys Asp Thr Arg Val Ala Lys Gly Glu Thr Ala Leu Leu Glu Cys
                165                 170                 175

Gly Pro Pro Lys Gly Ile Pro Glu Pro Thr Leu Ile Trp Ile Lys Asp
            180                 185                 190

Gly Val Pro Leu Asp Asp Leu Lys Ala Met Ser Phe Gly Ala Ser Ser
            195                 200                 205

Arg Val Arg Ile Val Asp Gly Gly Asn Leu Leu Ile Ser Asn Val Glu
210                 215                 220

Pro Ile Asp Glu Gly Asn Tyr Lys Cys Ile Ala Gln Asn Leu Val Gly
225                 230                 235                 240

Thr Arg Glu Ser Ser Tyr Ala Lys Leu Ile Val Gln Val Lys Pro Tyr
                245                 250                 255

Phe Met Lys Glu Pro Lys Asp Gln Val Met Leu Tyr Gly Gln Thr Ala
            260                 265                 270

Thr Phe His Cys Ser Val Gly Gly Asp Pro Pro Lys Val Leu Trp
            275                 280                 285

Lys Lys Glu Glu Gly Asn Ile Pro Val Ser Arg Ala Arg Ile Leu His
290                 295                 300

Asp Glu Lys Ser Leu Glu Ile Ser Asn Ile Thr Pro Thr Asp Glu Gly
305                 310                 315                 320

Thr Tyr Val Cys Glu Ala His Asn Asn Val Gly Gln Ile Ser Ala Arg
                325                 330                 335

Ala Ser Leu Ile Val His Ala Pro Pro Asn Phe Thr Lys Arg Pro Ser
            340                 345                 350

Asn Lys Lys Val Gly Leu Asn Gly Val Val Gln Leu Pro Cys Met Ala
            355                 360                 365

Ser Gly Asn Pro Pro Ser Val Phe Trp Thr Lys Glu Gly Val Ser
370                 375                 380
```

```
Thr Leu Met Phe Pro Asn Ser Ser His Gly Arg Gln Tyr Val Ala Ala
385                 390                 395                 400

Asp Gly Thr Leu Gln Ile Thr Asp Val Arg Gln Glu Asp Glu Gly Tyr
            405                 410                 415

Tyr Val Cys Ser Ala Phe Ser Val Asp Ser Ser Thr Val Arg Val
        420                 425                 430

Phe Leu Gln Val Ser Ser Val Asp Glu Arg Pro Pro Ile Ile Gln
        435                 440                 445

Ile Gly Pro Ala Asn Gln Thr Leu Pro Lys Gly Ser Val Ala Thr Leu
450                 455                 460

Pro Cys Arg Ala Thr Gly Asn Pro Ser Pro Arg Ile Lys Trp Phe His
465                 470                 475                 480

Asp Gly His Ala Val Gln Ala Gly Asn Arg Tyr Ser Ile Ile Gln Gly
                485                 490                 495

Ser Ser Leu Arg Val Asp Asp Leu Gln Leu Ser Asp Ser Gly Thr Tyr
            500                 505                 510

Thr Cys Thr Ala Ser Gly Glu Arg Gly Glu Thr Ser Trp Ala Ala Thr
        515                 520                 525

Leu Thr Val Glu Lys Pro Gly Ser Thr Ser Leu His Arg Ala Ala Asp
530                 535                 540

Pro Ser Thr Tyr Pro Ala Pro Pro Gly Thr Pro Lys Val Leu Asn Val
545                 550                 555                 560

Ser Arg Thr Ser Ile Ser Leu Arg Trp Ala Lys Ser Gln Glu Lys Pro
                565                 570                 575

Gly Ala Val Gly Pro Ile Ile Gly Tyr Thr Val Glu Tyr Phe Ser Pro
            580                 585                 590

Asp Leu Gln Thr Gly Trp Ile Val Ala Ala His Arg Val Gly Asp Thr
            595                 600                 605

Gln Val Thr Ile Ser Gly Leu Thr Pro Gly Thr Ser Tyr Val Phe Leu
610                 615                 620

Val Arg Ala Glu Asn Thr Gln Gly Ile Ser Val Pro Ser Gly Leu Ser
625                 630                 635                 640

Asn Val Ile Lys Thr Ile Glu Ala Asp Phe Asp Ala Ala Ser Ala Asn
                645                 650                 655

Asp Leu Ser Ala Ala Arg Thr Leu Leu Thr Gly Lys Ser Val Glu Leu
            660                 665                 670

Ile Asp Ala Ser Ala Ile Asn Ala Ser Ala Val Arg Leu Glu Trp Met
        675                 680                 685

Leu His Val Ser Ala Asp Glu Lys Tyr Val Glu Gly Leu Arg Ile His
        690                 695                 700

Tyr Lys Asp Ala Ser Val Pro Ser Ala Gln Tyr His Ser Ile Thr Val
705                 710                 715                 720

Met Asp Ala Ser Ala Glu Ser Phe Val Val Gly Asn Leu Lys Lys Tyr
                725                 730                 735

Thr Lys Tyr Glu Phe Phe Leu Thr Pro Phe Phe Glu Thr Ile Glu Gly
            740                 745                 750

Gln Pro Ser Asn Ser Lys Thr Ala Leu Thr Tyr Glu Asp Val Pro Ser
        755                 760                 765

Ala Pro Pro Asp Asn Ile Gln Ile Gly Met Tyr Asn Gln Thr Ala Gly
        770                 775                 780

Trp Val Arg Trp Thr Pro Pro Ser Gln His Asn Gly Asn Leu
785                 790                 795                 800
```

```
Tyr Gly Tyr Lys Ile Glu Val Ser Ala Gly Asn Thr Met Lys Val Leu
                805                 810                 815
Ala Asn Met Thr Leu Asn Ala Thr Thr Thr Ser Val Leu Leu Asn Asn
        820                 825                 830
Leu Thr Thr Gly Ala Val Tyr Ser Val Arg Leu Asn Ser Phe Thr Lys
            835                 840                 845
Ala Gly Asp Gly Pro Tyr Ser Lys Pro Ile Ser Leu Phe Met Asp Pro
850                 855                 860
Thr His His Val His Pro Arg Ala His Pro Ser Gly Thr His Asp
865                 870                 875                 880
Gly Arg His Glu Gly Gln Asp Leu Thr Tyr His Asn Asn Gly Asn Ile
                885                 890                 895
Pro Pro Gly Asp Ile Asn Pro Thr Thr His Lys Lys Thr Thr Asp Tyr
            900                 905                 910
Leu Ser Gly Pro Trp Leu Met Val Leu Val Cys Ile Val Leu Leu Val
        915                 920                 925
Leu Val Ile Ser Ala Ala Ile Ser Met Val Tyr Phe Lys Arg Lys His
    930                 935                 940
Gln Met Thr Lys Glu Leu Gly His Leu Ser Val Val Ser Asp Asn Glu
945                 950                 955                 960
Ile Thr Ala Leu Asn Ile Asn Ser Lys Glu Ser Leu Trp Ile Asp His
                965                 970                 975
His Arg Gly Trp Arg Thr Ala Asp Thr Asp Lys Asp Ser Gly Leu Ser
            980                 985                 990
Glu Ser Lys Leu Leu Ser His Val Asn Ser Ser Gln Ser Asn Tyr Asn
        995                 1000                1005
Asn Ser Asp Gly Gly Thr Asp Tyr Ala Glu Val Asp Thr Arg Asn
    1010                1015                1020
Leu Thr Thr Phe Tyr Asn Cys Arg Lys Ser Pro Asp Asn Pro Thr
    1025                1030                1035
Pro Tyr Ala Thr Thr Met Ile Ile Gly Thr Ser Ser Ser Glu Thr
    1040                1045                1050
Cys Thr Lys Thr Thr Ser Ile Ser Ala Asp Lys Asp Ser Gly Thr
    1055                1060                1065
His Ser Pro Tyr Ser Asp Ala Phe Ala Gly Gln Val Pro Ala Val
    1070                1075                1080
Pro Val Val Lys Ser Asn Tyr Leu Gln Tyr Pro Val Glu Pro Ile
    1085                1090                1095
Asn Trp Ser Glu Phe Leu Pro Pro Pro Glu His Pro Pro Pro
    1100                1105                1110
Ser Ser Thr Tyr Gly Tyr Ala Gln Gly Ser Pro Glu Ser Ser Arg
    1115                1120                1125
Lys Ser Ser Lys Ser Ala Gly Ser Gly Ile Ser Thr Asn Gln Ser
    1130                1135                1140
Ile Leu Asn Ala Ser Ile His Ser Ser Ser Ser Gly Gly Phe Ser
    1145                1150                1155
Ala Trp Gly Val Ser Pro Gln Tyr Ala Val Ala Cys Pro Pro Glu
    1160                1165                1170
Asn Val Tyr Ser Asn Pro Leu Ser Ala Val Ala Gly Gly Thr Gln
    1175                1180                1185
Asn Arg Tyr Gln Ile Thr Pro Thr Asn Gln His Pro Pro Gln Leu
    1190                1195                1200
Pro Ala Tyr Phe Ala Thr Thr Gly Pro Gly Gly Ala Val Pro Pro
```

```
                  1205                1210                1215

Asn His Leu Pro Phe Ala Thr Gln Arg His Ala Ala Ser Glu Tyr
            1220                1225                1230

Gln Ala Gly Leu Asn Ala Ala Arg Cys Ala Gln Ser Arg Ala Cys
            1235                1240                1245

Asn Ser Cys Asp Ala Leu Ala Thr Pro Ser Pro Met Gln Pro Pro
            1250                1255                1260

Pro Pro Val Pro Val Pro Glu Gly Trp Tyr Gln Pro Val His Pro
            1265                1270                1275

Asn Ser His Pro Met His Pro Thr Ser Ser Asn His Gln Ile Tyr
            1280                1285                1290

Gln Cys Ser Ser Glu Cys Ser Asp His Ser Arg Ser Ser Gln Ser
            1295                1300                1305

His Lys Arg Gln Leu Gln Leu Glu Glu His Gly Ser Ser Ala Lys
            1310                1315                1320

Gln Arg Gly Gly His His Arg Arg Ala Pro Val Val Gln Pro
            1325                1330                1335

Cys Met Glu Ser Glu Asn Glu Asn Met Leu Ala Glu Tyr Glu Gln
            1340                1345                1350

Arg Gln Tyr Thr Ser Asp Cys Cys Asn Ser Ser Arg Glu Gly Asp
            1355                1360                1365

Thr Cys Ser Cys Ser Glu Gly Ser Cys Leu Tyr Ala Glu Ala Gly
            1370                1375                1380

Glu Pro Ala Pro Arg Gln Met Thr Ala Lys Asn Thr His Pro Thr
            1385                1390                1395

Asp Leu Val Val Lys Lys Asn Glu Pro Ala Thr Leu Asn Cys Lys
            1400                1405                1410

Val Glu Gly Lys Pro Glu Pro Thr Ile Glu Trp Phe Lys Asp Gly
            1415                1420                1425

Glu Pro Val Ser Thr Asn Glu Lys Lys Ser His Arg Val Gln Phe
            1430                1435                1440

Lys Asp Gly Ala Leu Phe Phe Tyr Arg Thr Met Gln Gly Lys Lys
            1445                1450                1455

Glu Gln Asp Gly Gly Glu Tyr Trp Cys Val Ala Lys Asn Arg Val
            1460                1465                1470

Gly Gln Ala Val Ser Arg His Ala Ser Leu Gln Ile Ala Val Leu
            1475                1480                1485

Arg Asp Asp Phe Arg Val Glu Pro Lys Asp Thr Arg Val Ala Lys
            1490                1495                1500

Gly Glu Thr Ala Leu Leu Glu Cys Gly Pro Pro Lys Gly Ile Pro
            1505                1510                1515

Glu Pro Thr Leu Ile Trp Ile Lys Asp Gly Val Pro Leu Asp Asp
            1520                1525                1530

Leu Lys Ala Met Ser Phe Gly Ala Ser Ser Arg Val Arg Ile Val
            1535                1540                1545

Asp Gly Gly Asn Leu Leu Ile Ser Asn Val Glu Pro Ile Asp Glu
            1550                1555                1560

Gly Asn Tyr Lys Cys Ile Ala Gln Asn Leu Val Gly Thr Arg Glu
            1565                1570                1575

Ser Ser Tyr Ala Lys Leu Ile Val Gln Val Lys Pro Tyr Phe Met
            1580                1585                1590

Lys Glu Pro Lys Asp Gln Val Met Leu Tyr Gly Gln Thr Ala Thr
            1595                1600                1605
```

```
Phe His Cys Ser Val Gly Gly Asp Pro Pro Lys Val Leu Trp
    1610            1615            1620

Lys Lys Glu Glu Gly Asn Ile Pro Val Ser Arg Ala Arg Ile Leu
1625            1630            1635

His Asp Glu Lys Ser Leu Glu Ile Ser Asn Ile Thr Pro Thr Asp
    1640            1645            1650

Glu Gly Thr Tyr Val Cys Glu Ala His Asn Asn Val Gly Gln Ile
    1655            1660            1665

Ser Ala Arg Ala Ser Leu Ile Val His Ala Pro Pro Asn Phe Thr
    1670            1675            1680

Lys Arg Pro Ser Asn Lys Lys Val Gly Leu Asn Gly Val Val Gln
    1685            1690            1695

Leu Pro Cys Met Ala Ser Gly Asn Pro Pro Pro Ser Val Phe Trp
    1700            1705            1710

Thr Lys Glu Gly Val Ser Thr Leu Met Phe Pro Asn Ser Ser His
    1715            1720            1725

Gly Arg Gln Tyr Val Ala Ala Asp Gly Thr Leu Gln Ile Thr Asp
    1730            1735            1740

Val Arg Gln Glu Asp Glu Gly Tyr Tyr Val Cys Ser Ala Phe Ser
    1745            1750            1755

Val Val Asp Ser Ser Thr Val Arg Val Phe Leu Gln Val Ser Ser
    1760            1765            1770

Val Asp Glu Arg Pro Pro Pro Ile Ile Gln Ile Gly Pro Ala Asn
    1775            1780            1785

Gln Thr Leu Pro Lys Gly Ser Val Ala Thr Leu Pro Cys Arg Ala
    1790            1795            1800

Thr Gly Asn Pro Ser Pro Arg Ile Lys Trp Phe His Asp Gly His
    1805            1810            1815

Ala Val Gln Ala Gly Asn Arg Tyr Ser Ile Ile Gln Gly Ser Ser
    1820            1825            1830

Leu Arg Val Asp Asp Leu Gln Leu Ser Asp Ser Gly Thr Tyr Thr
    1835            1840            1845

Cys Thr Ala Ser Gly Glu Arg Gly Glu Thr Ser Trp Ala Ala Thr
    1850            1855            1860

Leu Thr Val Glu Lys Pro Gly Ser Thr Ser Leu His Arg Ala Ala
    1865            1870            1875

Asp Pro Ser Thr Tyr Pro Ala Pro Pro Gly Thr Pro Lys Val Leu
    1880            1885            1890

Asn Val Ser Arg Thr Ser Ile Ser Leu Arg Trp Ala Lys Ser Gln
    1895            1900            1905

Glu Lys Pro Gly Ala Val Gly Pro Ile Ile Gly Tyr Thr Val Glu
    1910            1915            1920

Tyr Phe Ser Pro Asp Leu Gln Thr Gly Trp Ile Val Ala Ala His
    1925            1930            1935

Arg Val Gly Asp Thr Gln Val Thr Ile Ser Gly Leu Thr Pro Gly
    1940            1945            1950

Thr Ser Tyr Val Phe Leu Val Arg Ala Glu Asn Thr Gln Gly Ile
    1955            1960            1965

Ser Val Pro Ser Gly Leu Ser Asn Val Ile Lys Thr Ile Glu Ala
    1970            1975            1980

Asp Phe Asp Ala Ala Ser Ala Asn Asp Leu Ser Ala Ala Arg Thr
    1985            1990            1995
```

```
Leu Leu Thr Gly Lys Ser Val Glu Leu Ile Asp Ala Ser Ala Ile
    2000                2005                2010

Asn Ala Ser Ala Val Arg Leu Glu Trp Met Leu His Val Ser Ala
    2015                2020                2025

Asp Glu Lys Tyr Val Glu Gly Leu Arg Ile His Tyr Lys Asp Ala
    2030                2035                2040

Ser Val Pro Ser Ala Gln Tyr His Ser Ile Thr Val Met Asp Ala
    2045                2050                2055

Ser Ala Glu Ser Phe Val Val Gly Asn Leu Lys Lys Tyr Thr Lys
    2060                2065                2070

Tyr Glu Phe Phe Leu Thr Pro Phe Phe Glu Thr Ile Glu Gly Gln
    2075                2080                2085

Pro Ser Asn Ser Lys Thr Ala Leu Thr Tyr Glu Asp Val Pro Ser
    2090                2095                2100

Ala Pro Pro Asp Asn Ile Gln Ile Gly Met Tyr Asn Gln Thr Ala
    2105                2110                2115

Gly Trp Val Arg Trp Thr Pro Pro Pro Ser Gln His His Asn Gly
    2120                2125                2130

Asn Leu Tyr Gly Tyr Lys Ile Glu Val Ser Ala Gly Asn Thr Met
    2135                2140                2145

Lys Val Leu Ala Asn Met Thr Leu Asn Ala Thr Thr Thr Ser Val
    2150                2155                2160

Leu Leu Asn Asn Leu Thr Thr Gly Ala Val Tyr Ser Val Arg Leu
    2165                2170                2175

Asn Ser Phe Thr Lys Ala Gly Asp Gly Pro Tyr Ser Lys Pro Ile
    2180                2185                2190

Ser Leu Phe Met Asp Pro Thr His His Val His Pro Pro Arg Ala
    2195                2200                2205

His Pro Ser Gly Thr His Asp Gly Arg His Glu Gly Gln Asp Leu
    2210                2215                2220

Thr Tyr His Asn Asn Gly Asn Ile Pro Pro Gly Asp Ile Asn Pro
    2225                2230                2235

Thr Thr His Lys Lys Thr Thr Asp Tyr Leu Ser Gly Pro Trp Leu
    2240                2245                2250

Met Val Leu Val Cys Ile Val Leu Leu Val Leu Val Ile Ser Ala
    2255                2260                2265

Ala Ile Ser Met Val Tyr Phe Lys Arg Lys His Gln Met Thr Lys
    2270                2275                2280

Glu Leu Gly His Leu Ser Val Val Ser Asp Asn Glu Ile Thr Ala
    2285                2290                2295

Leu Asn Ile Asn Ser Lys Glu Ser Leu Trp Ile Asp His His Arg
    2300                2305                2310

Gly Trp Arg Thr Ala Asp Thr Asp Lys Asp Ser Gly Leu Ser Glu
    2315                2320                2325

Ser Lys Leu Leu Ser His Val Asn Ser Ser Gln Ser Asn Tyr Asn
    2330                2335                2340

Asn Ser Asp Gly Gly Thr Asp Tyr Ala Glu Val Asp Thr Arg Asn
    2345                2350                2355

Leu Thr Thr Phe Tyr Asn Cys Arg Lys Ser Pro Asp Asn Pro Thr
    2360                2365                2370

Pro Tyr Ala Thr Thr Met Ile Ile Gly Thr Ser Ser Ser Glu Thr
    2375                2380                2385

Cys Thr Lys Thr Thr Ser Ile Ser Ala Asp Lys Asp Ser Gly Thr
```

His Ser Pro Tyr Ser Asp Ala Phe Ala Gly Gln Val Pro Ala Val
2405                2410                2415

Pro Val Val Lys Ser Asn Tyr Leu Gln Tyr Pro Val Glu Pro Ile
2420                2425                2430

Asn Trp Ser Glu Phe Leu Pro Pro Pro Glu His Pro Pro Pro
2435                2440                2445

Ser Ser Thr Tyr Gly Tyr Ala Gln Gly Ser Pro Glu Ser Ser Arg
2450                2455                2460

Lys Ser Ser Lys Ser Ala Gly Ser Gly Ile Ser Thr Asn Gln Ser
2465                2470                2475

Ile Leu Asn Ala Ser Ile His Ser Ser Ser Gly Gly Phe Ser
2480                2485                2490

Ala Trp Gly Val Ser Pro Gln Tyr Ala Val Ala Cys Pro Pro Glu
2495                2500                2505

Asn Val Tyr Ser Asn Pro Leu Ser Ala Val Ala Gly Gly Thr Gln
2510                2515                2520

Asn Arg Tyr Gln Ile Thr Pro Thr Asn Gln His Pro Pro Gln Leu
2525                2530                2535

Pro Ala Tyr Phe Ala Thr Thr Gly Pro Gly Gly Ala Val Pro Pro
2540                2545                2550

Asn His Leu Pro Phe Ala Thr Gln Arg His Ala Ala Ser Glu Tyr
2555                2560                2565

Gln Ala Gly Leu Asn Ala Ala Arg Cys Ala Gln Ser Arg Ala Cys
2570                2575                2580

Asn Ser Cys Asp Ala Leu Ala Thr Pro Ser Pro Met Gln Pro Pro
2585                2590                2595

Pro Pro Val Pro Val Pro Glu Gly Trp Tyr Gln Pro Val His Pro
2600                2605                2610

Asn Ser His Pro Met His Pro Thr Ser Ser Asn His Gln Ile Tyr
2615                2620                2625

Gln Cys Ser Ser Glu Cys Ser Asp His Ser Arg Ser Ser Gln Ser
2630                2635                2640

His Lys Arg Gln Leu Gln Leu Glu Glu His Gly Ser Ser Ala Lys
2645                2650                2655

Gln Arg Gly Gly His His Arg Arg Arg Ala Pro Val Val Gln Pro
2660                2665                2670

Cys Met Glu Ser Glu Asn Glu Asn Met Leu Ala Glu Tyr Glu Gln
2675                2680                2685

Arg Gln Tyr Thr Ser Asp Cys Cys Asn Ser Ser Arg Glu Gly Asp
2690                2695                2700

Thr Cys Ser Cys Ser Glu Gly Ser Cys Leu Tyr Ala Glu Ala Gly
2705                2710                2715

Glu Pro Ala Pro Arg Gln Met Thr Ala Lys Asn Thr
2720                2725                2730

<210> SEQ ID NO 14
<211> LENGTH: 1273
<212> TYPE: PRT
<213> ORGANISM: Caenorhabditis elegans

<400> SEQUENCE: 14

Met Phe Asn Arg Lys Thr Leu Leu Cys Thr Ile Leu Leu Val Leu Gln
1                5                  10                  15

```
Ala Val Ile Arg Ser Phe Cys Glu Asp Ala Ser Asn Leu Ala Pro Val
            20                  25                  30
Ile Ile Glu His Pro Ile Asp Val Val Ser Arg Gly Ser Pro Ala
        35                  40                  45
Thr Leu Asn Cys Gly Ala Lys Pro Ser Thr Ala Lys Ile Thr Trp Tyr
        50                  55                  60
Lys Asp Gly Gln Pro Val Ile Thr Asn Lys Glu Gln Val Asn Ser His
65                      70                  75                  80
Arg Ile Val Leu Asp Thr Gly Ser Leu Phe Leu Leu Lys Val Asn Ser
                85                  90                  95
Gly Lys Asn Gly Lys Asp Ser Asp Ala Gly Ala Tyr Tyr Cys Val Ala
                100                 105                 110
Ser Asn Glu His Gly Glu Val Lys Ser Asn Glu Gly Ser Leu Lys Leu
            115                 120                 125
Ala Met Leu Arg Glu Asp Phe Arg Val Arg Pro Arg Thr Val Gln Ala
        130                 135                 140
Leu Gly Gly Glu Met Ala Val Leu Glu Cys Ser Pro Pro Arg Gly Phe
145                 150                 155                 160
Pro Glu Pro Val Val Ser Trp Arg Lys Asp Asp Lys Glu Leu Arg Ile
                165                 170                 175
Gln Asp Met Pro Arg Tyr Thr Leu His Ser Asp Gly Asn Leu Ile Ile
            180                 185                 190
Asp Pro Val Asp Arg Ser Asp Ser Gly Thr Tyr Gln Cys Val Ala Asn
        195                 200                 205
Asn Met Val Gly Glu Arg Val Ser Asn Pro Ala Arg Leu Ser Val Phe
210                 215                 220
Glu Lys Pro Lys Phe Glu Gln Glu Pro Lys Asp Met Thr Val Asp Val
225                 230                 235                 240
Gly Ala Ala Val Leu Phe Asp Cys Arg Val Thr Gly Asp Pro Gln Pro
                245                 250                 255
Gln Ile Thr Trp Lys Arg Lys Asn Glu Pro Met Pro Val Thr Arg Ala
            260                 265                 270
Tyr Ile Ala Lys Asp Asn Arg Gly Leu Arg Ile Glu Arg Val Gln Pro
        275                 280                 285
Ser Asp Glu Gly Glu Tyr Val Cys Tyr Ala Arg Asn Pro Ala Gly Thr
290                 295                 300
Leu Glu Ala Ser Ala His Leu Arg Val Gln Ala Pro Pro Ser Phe Gln
305                 310                 315                 320
Thr Lys Pro Ala Asp Gln Ser Val Pro Ala Gly Gly Thr Ala Thr Phe
                325                 330                 335
Glu Cys Thr Leu Val Gly Gln Pro Ser Pro Ala Tyr Phe Trp Ser Lys
            340                 345                 350
Glu Gly Gln Gln Asp Leu Leu Phe Pro Ser Tyr Val Ser Ala Asp Gly
        355                 360                 365
Arg Thr Lys Val Ser Pro Thr Gly Thr Leu Thr Ile Glu Glu Val Arg
370                 375                 380
Gln Val Asp Glu Gly Ala Tyr Val Cys Ala Gly Met Asn Ser Ala Gly
385                 390                 395                 400
Ser Ser Leu Ser Lys Ala Ala Leu Lys Val Thr Thr Lys Ala Val Thr
                405                 410                 415
Gly Asn Thr Pro Ala Lys Pro Pro Thr Ile Glu His Gly His Gln
            420                 425                 430
Asn Gln Thr Leu Met Val Gly Ser Ser Ala Ile Leu Pro Cys Gln Ala
```

```
            435                 440                 445
Ser Gly Lys Pro Thr Pro Gly Ile Ser Trp Leu Arg Asp Gly Leu Pro
450                 455                 460

Ile Asp Ile Thr Asp Ser Arg Ile Ser Gln His Ser Thr Gly Ser Leu
465                 470                 475                 480

His Ile Ala Asp Leu Lys Lys Pro Asp Thr Gly Val Tyr Thr Cys Ile
                485                 490                 495

Ala Lys Asn Glu Asp Gly Glu Ser Thr Trp Ser Ala Ser Leu Thr Val
                500                 505                 510

Glu Asp His Thr Ser Asn Ala Gln Phe Val Arg Met Pro Asp Pro Ser
                515                 520                 525

Asn Phe Pro Ser Ser Pro Thr Gln Pro Ile Ile Val Asn Val Thr Asp
                530                 535                 540

Thr Glu Val Glu Leu His Trp Asn Ala Pro Ser Thr Ser Gly Ala Gly
545                 550                 555                 560

Pro Ile Thr Gly Tyr Ile Ile Gln Tyr Tyr Ser Pro Asp Leu Gly Gln
                565                 570                 575

Thr Trp Phe Asn Ile Pro Asp Tyr Val Ala Ser Thr Glu Tyr Arg Ile
                580                 585                 590

Lys Gly Leu Lys Pro Ser His Ser Tyr Met Phe Val Ile Arg Ala Glu
                595                 600                 605

Asn Glu Lys Gly Ile Gly Thr Pro Ser Val Ser Ser Ala Leu Val Thr
                610                 615                 620

Thr Ser Lys Pro Ala Ala Gln Val Ala Leu Ser Asp Lys Asn Lys Met
625                 630                 635                 640

Asp Met Ala Ile Ala Glu Lys Arg Leu Thr Ser Glu Gln Leu Ile Lys
                645                 650                 655

Leu Glu Glu Val Lys Thr Ile Asn Ser Thr Ala Val Arg Leu Phe Trp
                660                 665                 670

Lys Lys Arg Lys Leu Glu Glu Leu Ile Asp Gly Tyr Tyr Ile Lys Trp
                675                 680                 685

Arg Gly Pro Pro Arg Thr Asn Asp Asn Gln Tyr Val Asn Val Thr Ser
690                 695                 700

Pro Ser Thr Glu Asn Tyr Val Val Ser Asn Leu Met Pro Phe Thr Asn
705                 710                 715                 720

Tyr Glu Phe Phe Val Ile Pro Tyr His Ser Gly Val His Ser Ile His
                725                 730                 735

Gly Ala Pro Ser Asn Ser Met Asp Val Leu Thr Ala Glu Ala Pro Pro
                740                 745                 750

Ser Leu Pro Pro Glu Asp Val Arg Ile Arg Met Leu Asn Leu Thr Thr
                755                 760                 765

Leu Arg Ile Ser Trp Lys Ala Pro Lys Ala Asp Gly Ile Asn Gly Ile
                770                 775                 780

Leu Lys Gly Phe Gln Ile Val Ile Val Gly Gln Ala Pro Asn Asn Asn
785                 790                 795                 800

Arg Asn Ile Thr Thr Asn Glu Arg Ala Ala Ser Val Thr Leu Phe His
                805                 810                 815

Leu Val Thr Gly Met Thr Tyr Lys Ile Arg Val Ala Ala Arg Ser Asn
                820                 825                 830

Gly Gly Val Gly Val Ser His Gly Thr Ser Glu Val Ile Met Asn Gln
                835                 840                 845

Asp Thr Leu Glu Lys His Leu Ala Ala Gln Gln Glu Asn Glu Ser Phe
850                 855                 860
```

```
Leu Tyr Gly Leu Ile Asn Lys Ser His Val Pro Val Ile Val
865                 870                 875                 880

Ala Ile Leu Ile Ile Phe Val Val Ile Ile Ala Tyr Cys Tyr Trp
                885                 890                 895

Arg Asn Ser Arg Asn Ser Asp Gly Lys Asp Arg Ser Phe Ile Lys Ile
            900                 905                 910

Asn Asp Gly Ser Val His Met Ala Ser Asn Asn Leu Trp Asp Val Ala
            915                 920                 925

Gln Asn Pro Asn Gln Asn Pro Met Tyr Asn Thr Ala Gly Arg Met Thr
    930                 935                 940

Met Asn Asn Arg Asn Gly Gln Ala Leu Tyr Ser Leu Thr Pro Asn Ala
945                 950                 955                 960

Gln Asp Phe Phe Asn Asn Cys Asp Asp Tyr Ser Gly Thr Met His Arg
                965                 970                 975

Pro Gly Ser Glu His His Tyr His Tyr Ala Gln Leu Thr Gly Gly Pro
            980                 985                 990

Gly Asn Ala Met Ser Thr Phe Tyr  Gly Asn Gln Tyr His  Asp Asp Pro
            995                 1000                1005

Ser Pro  Tyr Ala Thr Thr Thr  Leu Val Leu Ser Asn  Gln Gln Pro
    1010                1015                1020

Ala Trp  Leu Asn Asp Lys Met  Leu Arg Ala Pro Ala  Met Pro Thr
    1025                1030                1035

Asn Pro  Val Pro Pro Glu Pro  Pro Ala Arg Tyr Ala  Asp His Thr
    1040                1045                1050

Ala Gly  Arg Arg Ser Arg Ser  Ser Arg Ala Ser Asp  Gly Arg Gly
    1055                1060                1065

Thr Leu  Asn Gly Gly Leu His  His Arg Thr Ser Gly  Ser Gln Arg
    1070                1075                1080

Ser Asp  Ser Pro Pro His Thr  Asp Val Ser Tyr Val  Gln Leu His
    1085                1090                1095

Ser Ser  Asp Gly Thr Gly Ser  Ser Lys Glu Arg Thr  Gly Glu Arg
    1100                1105                1110

Arg Thr  Pro Pro Asn Lys Thr  Leu Met Asp Phe Ile  Pro Pro Pro
    1115                1120                1125

Pro Ser  Asn Pro Pro Pro Pro  Gly Gly His Val Tyr  Asp Asp Ile
    1130                1135                1140

Phe Gln  Thr Ala Thr Arg Arg  Gln Leu Asn Arg Gly  Ser Thr Pro
    1145                1150                1155

Arg Glu  Asp Thr Tyr Asp Ser  Val Ser Asp Gly Ala  Phe Ala Arg
    1160                1165                1170

Val Asp  Val Asn Ala Arg Pro  Thr Ser Arg Asn Arg  Asn Leu Gly
    1175                1180                1185

Gly Arg  Pro Leu Lys Gly Lys  Arg Asp Asp Asp Ser  Gln Arg Ser
    1190                1195                1200

Ser Leu  Met Met Asp Asp Asp  Gly Gly Ser Ser Glu  Ala Asp Gly
    1205                1210                1215

Glu Asn  Ser Glu Gly Asp Val  Pro Arg Gly Gly Val  Arg Lys Ala
    1220                1225                1230

Val Pro  Arg Met Gly Ile Ser  Ala Ser Thr Leu Ala  His Ser Cys
    1235                1240                1245

Tyr Gly  Thr Asn Gly Thr Ala  Gln Arg Phe Arg Ser  Ile Pro Arg
    1250                1255                1260
```

```
Asn Asn Gly Ile Val Thr Gln   Glu Gln Thr
    1265                1270
```

<210> SEQ ID NO 15
<211> LENGTH: 1525
<212> TYPE: PRT
<213> ORGANISM: Exaiptasia pallida
<220> FEATURE:
<221> NAME/KEY: misc_feature
<222> LOCATION: (387)..(387)
<223> OTHER INFORMATION: Xaa can be any naturally occurring amino acid
<220> FEATURE:
<221> NAME/KEY: misc_feature
<222> LOCATION: (791)..(791)
<223> OTHER INFORMATION: Xaa can be any naturally occurring amino acid

<400> SEQUENCE: 15

```
Met Val Tyr Trp Glu Lys Leu Val Cys Leu Leu Val Val Ile Val
1               5                   10                  15

Asn Tyr Gln His Cys Ser Ala Asp Ser Leu Pro Gln Ile Ile Glu His
            20                  25                  30

Pro Glu Asp Val Ile Ala Ala Lys Asn Ser Asn Thr Glu Leu Arg Cys
        35                  40                  45

Lys Ala Thr Gly Ser Pro Lys Pro Ile Ile His Trp Leu Arg Asn Gly
50                  55                  60

Lys Lys Val Pro Thr Asp Glu Asp Pro Glu Lys Arg Arg Tyr Ile
65                  70                  75                  80

Leu Pro Ser Gly Asn Leu Thr Phe Ile Arg Val Ile Gln Lys Lys Lys
                85                  90                  95

Arg Thr Asp Ser Gly Lys Tyr Gln Cys Val Ala Val Asn Lys Val Gly
            100                 105                 110

Lys Thr Thr Ser Lys Ala Ala Thr Leu Leu Val Gly Val Leu Arg Ser
        115                 120                 125

Gln Phe Lys Thr Glu Pro Arg Asp Arg Thr Val Thr Ala Gly Asn Pro
130                 135                 140

Val Thr Leu Lys Cys Asn Pro Pro Arg Gly Lys Pro Ser Pro Lys Val
145                 150                 155                 160

Ser Trp Ile Lys Asp Gly Val Met Val Lys Pro Asp Gly Lys Arg Val
                165                 170                 175

Leu Ile Lys Glu Pro Gly Ser Leu Tyr Ile Ser Ala Ala Arg Lys Val
            180                 185                 190

Asp Gln Gly Lys Tyr Val Cys Leu Ala Thr Asn Pro Leu Gly Gln Lys
        195                 200                 205

Lys Ser Asn Thr Ala Arg Leu Thr Val Lys Glu Leu Pro Ala Thr Ala
    210                 215                 220

Leu Arg Ile Arg Pro Ala Gln Lys Thr Val Ser Ala Gly Ser Ser Val
225                 230                 235                 240

Thr Phe Gln Cys Asp Tyr Arg Asp Gly Pro Gln Gly Ala Ile Arg Trp
                245                 250                 255

Ser Lys Lys Gly Gly Thr Leu Pro Asn Gln Arg Phe Ser Thr Thr Gln
            260                 265                 270

His Gly Lys Leu Thr Leu Asn Asn Ile Gln Pro Gly Asp Glu Gly Glu
        275                 280                 285

Tyr Val Cys Ser Val Ser Pro Thr Leu Ser Val Ser Ser Met Leu Ile
    290                 295                 300

Val Gln Met Thr Ser Pro Ser Phe Asn Lys Leu Phe Pro Asp Gly Thr
305                 310                 315                 320
```

```
Ser Thr Ala Ser Pro Leu Pro Gln Ala Lys Pro Ser Ile Thr Met Leu
            325                 330                 335

Pro Lys Asp Val Ile Val Arg Glu Gly Ala Thr Ala Lys Phe Ser Cys
        340                 345                 350

Lys Ala Thr Gly Asn Pro Leu Pro Thr Val Phe Trp Asp Gln Lys Ser
            355                 360                 365

Thr Arg Gln Thr Met Phe Pro His Gln Asn Asn Gly Arg Phe Glu Val
    370                 375                 380

Lys Thr Xaa Gly Asp Leu Ile Ile Lys Asn Val Gln Lys Gln Asp Lys
385                 390                 395                 400

Gly Glu Tyr Val Cys Ser Ala Ile Ser Gln Ala Gly Val Glu Thr Ala
                405                 410                 415

Ser Ala Met Leu Val Val Val Gly Ile Leu Asp Thr Lys Pro Thr Leu
            420                 425                 430

Lys Thr Lys Pro Leu Asn Gln Thr Val Asn Lys Phe Glu Asp Ala Ile
        435                 440                 445

Phe Ser Cys Thr Phe Asp Gly Val Pro Val Pro Ser Ile Glu Trp Ser
    450                 455                 460

Lys Gly Leu Val Leu Ser Asn Ser Ala Lys Tyr Ile Ile Lys Thr Val
465                 470                 475                 480

Gly Ser Thr Ser Gln Leu Lys Val Ile Ser Ser Thr Gln Asn Asp Ala
                485                 490                 495

Gly Gln Tyr Glu Cys Thr Ala Thr Asn Thr Leu Gly Thr Val Lys Gly
            500                 505                 510

Val Val Gln Leu Thr Val Val Asp Pro Thr Thr Thr Leu Leu Pro Val
        515                 520                 525

Val Leu Thr Thr Lys Pro Ala Val Pro Pro Leu Lys Lys Leu Gln Pro
    530                 535                 540

Pro Ser His Leu Ile Ala Arg Pro Leu Lys Ser His Asp Ser Val Glu
545                 550                 555                 560

Leu Val Trp Thr Ser Thr Lys Ala Ser Leu Ser Gln Pro Ile Met Tyr
                565                 570                 575

Thr Val Glu Tyr Arg Lys Val Gly His Lys Met Trp Lys Val Ala Met
            580                 585                 590

Leu Leu Thr Thr Val Asp Arg Cys Lys Val Thr Asn Leu Gln Pro Leu
        595                 600                 605

Thr Met Tyr Glu Phe Ser Val Arg Ala Lys Ala Gly Gln Glu Gln Ser
    610                 615                 620

Lys Arg Thr Thr Thr Arg Phe Lys Thr Arg Lys Thr Ala Thr Ser
625                 630                 635                 640

Val Val Pro Val Ile Pro Arg Lys Pro Arg Pro Thr Thr Phe Gly Pro
                645                 650                 655

Ala Lys Asn Ala Lys Val Ile Val Lys Ala Lys Pro Val Lys Trp Asp
            660                 665                 670

Lys Leu Asn Ile Thr Trp Lys Phe Asp Arg Lys Ile Lys Lys Leu Ser
        675                 680                 685

Ala Gly Phe Asn Val Phe Trp Arg Lys Glu Glu Ser Ala Asp Asp Phe
    690                 695                 700

Lys Gln Met Ala Val Ile Gly Asp Gly Val Gln Glu His Met Leu Asn
705                 710                 715                 720

Gly Leu Ser Ala Asn Thr Ser Tyr Val Ile Gln Val Glu Val Tyr Phe
                725                 730                 735

Ser Lys His Thr Leu Pro Lys Ser Glu Glu Val Val Gly Val Thr Gly
```

```
                740             745             750
Val Arg Asp Lys Gly Leu Ile Val Ile Leu Asp Glu Gly Lys Lys Asp
            755             760             765
Gly Ser Glu Gly Asp Val Gln Ile Ile Gln Ala Asp Thr Lys Ser Gly
            770             775             780
Gly Thr Trp Ser Arg Val Xaa Glu Phe Val Arg Lys Pro Trp Phe Ile
785             790             795             800
Ala Ile Met Gly Gly Ile Leu Trp Ile Gly Leu Phe Val Ile Val Leu
            805             810             815
Phe Leu Tyr Arg Arg Arg Arg Arg Asn Arg Arg Asn Leu Lys Gln Arg
            820             825             830
Lys Leu Lys Leu Gln Ile Ala Glu Ile Gln Arg Ala Pro Thr Ser Pro
            835             840             845
Gln Gly His Lys Thr Leu Trp Met Asp Asp Val Asn Thr Thr Asp Thr
            850             855             860
Pro Pro Gln Gln Leu Ala Asn Asn Arg Ile Ser Asp Thr Ser Ser Thr
865             870             875             880
Glu Cys Leu Asn Arg Ser Val Thr Ser Cys Cys Ala Arg Arg Gly Ile
            885             890             895
Asn Ser Asn Thr Ala Asp Phe Pro Asn Lys Ile Thr Ile Asn Ser Leu
            900             905             910
Thr Gly Ser Arg Leu Gly Glu Pro Asn Gln Phe Asp Ala Ser Thr Glu
            915             920             925
Ser Lys Leu Ser Ser Glu Gly Lys Thr Asn Asn Val His His Ser Ile
            930             935             940
Asn Asn Tyr Arg Glu His Leu Asn Lys Ser Thr Lys Phe Asp Glu Val
945             950             955             960
Gly Glu Arg Gly Ser Leu Gly Ser Arg Ser Gly Ser Glu Ala Thr Leu
            965             970             975
Pro Arg Ala Met Pro Gln Gln Thr Ser Phe Leu Thr Pro Thr Gln Gln
            980             985             990
Phe Ile Asn Arg Lys Lys Ala Asn  Thr Arg Ser Asp Ser  Pro Ala Ser
            995             1000            1005
Gln His  Lys Asp Pro Asn Lys  Thr Pro Asp Ser  Ser Ile Ser
    1010            1015            1020
Glu Lys  Ser Lys Pro Lys Leu  Lys Ile Gln Ser Phe  Glu Met Ala
    1025            1030            1035
Ser Asn  Gly Ser Ile Pro Gly  Thr Thr Thr Phe His  Ala Asp Pro
    1040            1045            1050
Pro Pro  Thr Tyr Glu Ala Val  Leu Lys Glu Thr Glu  Leu Glu Lys
    1055            1060            1065
Gln Leu  Glu Asp Gly Glu Glu  Lys Ser Lys Ser Arg  Glu Glu Leu
    1070            1075            1080
Ala Glu  Lys Leu Lys Gly Thr  Pro Phe Asn Asp Lys  Pro Thr Pro
    1085            1090            1095
Arg Ala  Pro Ser Pro Pro Leu  Ser Glu Arg Ser Cys  Arg Thr Thr
    1100            1105            1110
Ser Ser  Cys Gly Ser Arg Lys  Arg Lys Val Leu Lys  Pro Pro Pro
    1115            1120            1125
Arg Leu  Ala Ile Leu Asn Trp  Ala Asp Leu Leu Pro  Pro Pro Pro
    1130            1135            1140
Ser His  Pro Pro Pro Ser Ser  Leu Gly Ser Pro Pro  Pro Ser Pro
    1145            1150            1155
```

-continued

Pro Phe Ser Leu Arg Ser Gly Met Thr Gly Met Ser Gly Met Thr
1160              1165              1170

Gly Met Ser Gly Leu Thr Gly Met Ser Gly Met Thr Gly Leu Thr
1175              1180              1185

Gly Met Thr Gly Met Thr Gly Arg Thr Gly Lys Ser Ser Gly Asn
1190              1195              1200

Gly Leu Val Asp Asn Glu Ile Pro Glu Arg Pro Arg Lys Lys Pro
1205              1210              1215

Pro Ser Ser Ala Val Ser Asp Ser Ala Val Ser Ala Ala Glu Pro
1220              1225              1230

Lys Val Pro Gly Ser Thr Lys Ser Gly Lys Ser Gly His Lys His
1235              1240              1245

Lys Lys Pro Lys Pro Lys Ala Leu Pro Ile Asp Leu Glu Gly Ile
1250              1255              1260

Thr Ser Asp Ile Ile Met Gln Trp Ala Asp Ser Val Thr Asn Thr
1265              1270              1275

Ser Gly Ser Asp Asp Asp Ser Ser Cys Ser Ser Pro Ser Arg Val
1280              1285              1290

Ser Ser Thr Gly Ser Phe Phe Thr Asp Ala Asp Phe Ala Asn Ala
1295              1300              1305

Val Arg Ala Ala Ala Glu Cys Gly Gly Phe Asn Met Glu Thr Tyr
1310              1315              1320

Gly Leu Met Asp Ser Leu Gly Tyr Pro Pro Tyr Ser Gly Ser
1325              1330              1335

Trp Lys Lys Gly Asn Ser Thr Pro Ser Gly Ser Asp Pro Ser Gly
1340              1345              1350

Pro Ile Thr Ser Thr Pro Arg Asn Pro Gln Asn Lys Thr Lys Trp
1355              1360              1365

Glu Thr Gly Ser Glu Gly Asp Leu Asp Phe Thr Pro Pro Ile Thr
1370              1375              1380

Val Arg Pro Arg Phe Thr Arg Lys Val Gln Pro Asn Glu Asn Gly
1385              1390              1395

Thr Pro Pro Pro Val Ala Pro Ser Lys Met Ala Ala Asp Met Gly
1400              1405              1410

Ile Arg Lys Val Ala Arg Ser Pro Val Pro Leu Val Pro Ser Gln
1415              1420              1425

Pro Arg Arg Pro Ile Pro Arg Ala Ala Arg Met Asn Ser Asn Ser
1430              1435              1440

Pro Val Pro Gly Pro Gly Gln Ile Ile Val Gln Pro Leu Lys Lys
1445              1450              1455

Thr Ser Ala Leu Asn Ala Pro Glu Ser Ala Ser Lys Ile Pro Val
1460              1465              1470

Thr Lys Lys Phe Ala Val Val Lys Lys Ile Pro Gln Ser Lys Asp
1475              1480              1485

Thr Glu Pro Tyr Asn Ser Ala Thr Leu Ser Ser Ser Gly Lys Ser
1490              1495              1500

Ser Thr Ser Thr Ala Ser Thr Val Lys Thr Ser Thr Met Gly Asp
1505              1510              1515

Ser Asp Ala Glu Ser Ala Ala
1520              1525

<210> SEQ ID NO 16
<211> LENGTH: 1651

<212> TYPE: PRT
<213> ORGANISM: Homo sapiens

<400> SEQUENCE: 16

```
Met Lys Trp Lys His Val Pro Phe Leu Val Met Ile Ser Leu Leu Ser
1               5                   10                  15

Leu Ser Pro Asn His Leu Phe Leu Ala Gln Leu Ile Pro Asp Pro Glu
            20                  25                  30

Asp Val Glu Arg Gly Asn Asp His Gly Thr Pro Ile Pro Thr Ser Asp
        35                  40                  45

Asn Asp Asp Asn Ser Leu Gly Tyr Thr Gly Ser Arg Leu Arg Gln Glu
    50                  55                  60

Asp Phe Pro Pro Arg Ile Val Glu His Pro Ser Asp Leu Ile Val Ser
65                  70                  75                  80

Lys Gly Glu Pro Ala Thr Leu Asn Cys Lys Ala Glu Gly Arg Pro Thr
                85                  90                  95

Pro Thr Ile Glu Trp Tyr Lys Gly Gly Glu Arg Val Glu Thr Asp Lys
            100                 105                 110

Asp Asp Pro Arg Ser His Arg Met Leu Leu Pro Ser Gly Ser Leu Phe
        115                 120                 125

Phe Leu Arg Ile Val His Gly Arg Lys Ser Arg Pro Asp Glu Gly Val
    130                 135                 140

Tyr Val Cys Val Ala Arg Asn Tyr Leu Gly Glu Ala Val Ser His Asn
145                 150                 155                 160

Ala Ser Leu Glu Val Ala Ile Leu Arg Asp Asp Phe Arg Gln Asn Pro
                165                 170                 175

Ser Asp Val Met Val Ala Val Gly Glu Pro Ala Val Met Glu Cys Gln
            180                 185                 190

Pro Pro Arg Gly His Pro Glu Pro Thr Ile Ser Trp Lys Lys Asp Gly
        195                 200                 205

Ser Pro Leu Asp Asp Lys Asp Glu Arg Ile Thr Ile Arg Gly Gly Lys
    210                 215                 220

Leu Met Ile Thr Tyr Thr Arg Lys Ser Asp Ala Gly Lys Tyr Val Cys
225                 230                 235                 240

Val Gly Thr Asn Met Val Gly Glu Arg Glu Ser Glu Val Ala Glu Leu
                245                 250                 255

Thr Val Leu Glu Arg Pro Ser Phe Val Lys Arg Pro Ser Asn Leu Ala
            260                 265                 270

Val Thr Val Asp Asp Ser Ala Glu Phe Lys Cys Glu Ala Arg Gly Asp
        275                 280                 285

Pro Val Pro Thr Val Arg Trp Arg Lys Asp Asp Gly Glu Leu Pro Lys
    290                 295                 300

Ser Arg Tyr Glu Ile Arg Asp Asp His Thr Leu Lys Ile Arg Lys Val
305                 310                 315                 320

Thr Ala Gly Asp Met Gly Ser Tyr Thr Cys Val Ala Glu Asn Met Val
                325                 330                 335

Gly Lys Ala Glu Ala Ser Ala Thr Leu Thr Val Gln Glu Pro Pro His
            340                 345                 350

Phe Val Val Lys Pro Arg Asp Gln Val Val Ala Leu Gly Arg Thr Val
        355                 360                 365

Thr Phe Gln Cys Glu Ala Thr Gly Asn Pro Gln Pro Ala Ile Phe Trp
    370                 375                 380

Arg Arg Glu Gly Ser Gln Asn Leu Leu Phe Ser Tyr Gln Pro Pro Gln
385                 390                 395                 400
```

-continued

```
Ser Ser Ser Arg Phe Ser Val Ser Gln Thr Gly Asp Leu Thr Ile Thr
            405                 410                 415

Asn Val Gln Arg Ser Asp Val Gly Tyr Tyr Ile Cys Gln Thr Leu Asn
            420                 425                 430

Val Ala Gly Ser Ile Ile Thr Lys Ala Tyr Leu Glu Val Thr Asp Val
            435                 440                 445

Ile Ala Asp Arg Pro Pro Val Ile Arg Gln Gly Pro Val Asn Gln
450                 455                 460

Thr Val Ala Val Asp Gly Thr Phe Val Leu Ser Cys Val Ala Thr Gly
465                 470                 475                 480

Ser Pro Val Pro Thr Ile Leu Trp Arg Lys Asp Gly Val Leu Val Ser
                485                 490                 495

Thr Gln Asp Ser Arg Ile Lys Gln Leu Glu Asn Gly Val Leu Gln Ile
            500                 505                 510

Arg Tyr Ala Lys Leu Gly Asp Thr Gly Arg Tyr Thr Cys Ile Ala Ser
            515                 520                 525

Thr Pro Ser Gly Glu Ala Thr Trp Ser Ala Tyr Ile Glu Val Gln Glu
            530                 535                 540

Phe Gly Val Pro Val Gln Pro Arg Pro Thr Asp Pro Asn Leu Ile
545                 550                 555                 560

Pro Ser Ala Pro Ser Lys Pro Glu Val Thr Asp Val Ser Arg Asn Thr
                565                 570                 575

Val Thr Leu Ser Trp Gln Pro Asn Leu Asn Ser Gly Ala Thr Pro Thr
            580                 585                 590

Ser Tyr Ile Ile Glu Ala Phe Ser His Ala Ser Gly Ser Ser Trp Gln
            595                 600                 605

Thr Val Ala Glu Asn Val Lys Thr Glu Thr Ser Ala Ile Lys Gly Leu
610                 615                 620

Lys Pro Asn Ala Ile Tyr Leu Phe Leu Val Arg Ala Ala Asn Ala Tyr
625                 630                 635                 640

Gly Ile Ser Asp Pro Ser Gln Ile Ser Asp Pro Val Lys Thr Gln Asp
                645                 650                 655

Val Leu Pro Thr Ser Gln Gly Val Asp His Lys Gln Val Gln Arg Glu
            660                 665                 670

Leu Gly Asn Ala Val Leu His Leu His Asn Pro Thr Val Leu Ser Ser
            675                 680                 685

Ser Ser Ile Glu Val His Trp Thr Val Asp Gln Gln Ser Gln Tyr Ile
            690                 695                 700

Gln Gly Tyr Lys Ile Leu Tyr Arg Pro Ser Gly Ala Asn His Gly Glu
705                 710                 715                 720

Ser Asp Trp Leu Val Phe Glu Val Arg Thr Pro Ala Lys Asn Ser Val
                725                 730                 735

Val Ile Pro Asp Leu Arg Lys Gly Val Asn Tyr Glu Ile Lys Ala Arg
            740                 745                 750

Pro Phe Phe Asn Glu Phe Gln Gly Ala Asp Ser Glu Ile Lys Phe Ala
            755                 760                 765

Lys Thr Leu Glu Glu Ala Pro Ser Ala Pro Pro Gln Gly Val Thr Val
            770                 775                 780

Ser Lys Asn Asp Gly Asn Gly Thr Ala Ile Leu Val Ser Trp Gln Pro
785                 790                 795                 800

Pro Pro Glu Asp Thr Gln Asn Gly Met Val Gln Glu Tyr Lys Val Trp
                805                 810                 815
```

Cys Leu Gly Asn Glu Thr Arg Tyr His Ile Asn Lys Thr Val Asp Gly
                820                 825                 830

Ser Thr Phe Ser Val Val Ile Pro Phe Leu Val Pro Gly Ile Arg Tyr
        835                 840                 845

Ser Val Glu Val Ala Ala Ser Thr Gly Ala Gly Ser Gly Val Lys Ser
    850                 855                 860

Glu Pro Gln Phe Ile Gln Leu Asp Ala His Gly Asn Pro Val Ser Pro
865                 870                 875                 880

Glu Asp Gln Val Ser Leu Ala Gln Gln Ile Ser Asp Val Val Lys Gln
                885                 890                 895

Pro Ala Phe Ile Ala Gly Ile Gly Ala Ala Cys Trp Ile Ile Leu Met
            900                 905                 910

Val Phe Ser Ile Trp Leu Tyr Arg His Arg Lys Lys Arg Asn Gly Leu
        915                 920                 925

Thr Ser Thr Tyr Ala Gly Ile Arg Lys Val Pro Ser Phe Thr Phe Thr
    930                 935                 940

Pro Thr Val Thr Tyr Gln Arg Gly Gly Glu Ala Val Ser Ser Gly Gly
945                 950                 955                 960

Arg Pro Gly Leu Leu Asn Ile Ser Glu Pro Ala Ala Gln Pro Trp Leu
                965                 970                 975

Ala Asp Thr Trp Pro Asn Thr Gly Asn Asn His Asn Asp Cys Ser Ile
            980                 985                 990

Ser Cys Cys Thr Ala Gly Asn Gly  Asn Ser Asp Ser Asn  Leu Thr Thr
        995                 1000                1005

Tyr Ser  Arg Pro Ala Asp Cys  Ile Ala Asn Tyr Asn  Asn Gln Leu
   1010                 1015                 1020

Asp Asn  Lys Gln Thr Asn Leu  Met Leu Pro Glu Ser  Thr Val Tyr
   1025                 1030                 1035

Gly Asp  Val Asp Leu Ser Asn  Lys Ile Asn Glu Met  Lys Thr Phe
   1040                 1045                 1050

Asn Ser  Pro Asn Leu Lys Asp  Gly Arg Phe Val Asn  Pro Ser Gly
   1055                 1060                 1065

Gln Pro  Thr Pro Tyr Ala Thr  Thr Gln Leu Ile Gln  Ser Asn Leu
   1070                 1075                 1080

Ser Asn  Asn Met Asn Asn Gly  Ser Gly Asp Ser Gly  Glu Lys His
   1085                 1090                 1095

Trp Lys  Pro Leu Gly Gln Gln  Lys Gln Glu Val Ala  Pro Val Gln
   1100                 1105                 1110

Tyr Asn  Ile Val Glu Gln Asn  Lys Leu Asn Lys Asp  Tyr Arg Ala
   1115                 1120                 1125

Asn Asp  Thr Val Pro Pro Thr  Ile Pro Tyr Asn Gln  Ser Tyr Asp
   1130                 1135                 1140

Gln Asn  Thr Gly Gly Ser Tyr  Asn Ser Ser Asp Arg  Gly Ser Ser
   1145                 1150                 1155

Thr Ser  Gly Ser Gln Gly His  Lys Lys Gly Ala Arg  Thr Pro Lys
   1160                 1165                 1170

Val Pro  Lys Gln Gly Gly Met  Asn Trp Ala Asp Leu  Leu Pro Pro
   1175                 1180                 1185

Pro Pro  Ala His Pro Pro His  Ser Asn Ser Glu Glu  Tyr Asn
   1190                 1195                 1200

Ile Ser  Val Asp Glu Ser Tyr  Asp Gln Glu Met Pro  Cys Pro Val
   1205                 1210                 1215

Pro Pro  Ala Arg Met Tyr Leu  Gln Gln Asp Glu Leu  Glu Glu Glu

```
                1220                1225                1230

Glu Asp Glu Arg Gly Pro Thr Pro Pro Val Arg Gly Ala Ala Ser
            1235                1240                1245

Ser Pro Ala Ala Val Ser Tyr Ser His Gln Ser Thr Ala Thr Leu
            1250                1255                1260

Thr Pro Ser Pro Gln Glu Glu Leu Gln Pro Met Leu Gln Asp Cys
            1265                1270                1275

Pro Glu Glu Thr Gly His Met Gln His Gln Pro Asp Arg Arg Arg
            1280                1285                1290

Gln Pro Val Ser Pro Pro Pro Pro Arg Pro Ile Ser Pro Pro
            1295                1300                1305

His Thr Tyr Gly Tyr Ile Ser Gly Pro Leu Val Ser Asp Met Asp
            1310                1315                1320

Thr Asp Ala Pro Glu Glu Glu Asp Glu Ala Asp Met Glu Val
            1325                1330                1335

Ala Lys Met Gln Thr Arg Arg Leu Leu Leu Arg Gly Leu Glu Gln
            1340                1345                1350

Thr Pro Ala Ser Ser Val Gly Asp Leu Glu Ser Ser Val Thr Gly
            1355                1360                1365

Ser Met Ile Asn Gly Trp Gly Ser Ala Ser Glu Glu Asp Asn Ile
            1370                1375                1380

Ser Ser Gly Arg Ser Ser Val Ser Ser Ser Asp Gly Ser Phe Phe
            1385                1390                1395

Thr Asp Ala Asp Phe Ala Gln Ala Val Ala Ala Ala Glu Tyr
            1400                1405                1410

Ala Gly Leu Lys Val Ala Arg Arg Gln Met Gln Asp Ala Ala Gly
            1415                1420                1425

Arg Arg His Phe His Ala Ser Gln Cys Pro Arg Pro Thr Ser Pro
            1430                1435                1440

Val Ser Thr Asp Ser Asn Met Ser Ala Ala Val Met Gln Lys Thr
            1445                1450                1455

Arg Pro Ala Lys Lys Leu Lys His Gln Pro Gly His Leu Arg Arg
            1460                1465                1470

Glu Thr Tyr Thr Asp Asp Leu Pro Pro Pro Val Pro Pro Pro
            1475                1480                1485

Ala Ile Lys Ser Pro Thr Ala Gln Ser Lys Thr Gln Leu Glu Val
            1490                1495                1500

Arg Pro Val Val Val Pro Lys Leu Pro Ser Met Asp Ala Arg Thr
            1505                1510                1515

Asp Arg Ser Ser Asp Arg Lys Gly Ser Ser Tyr Lys Gly Arg Glu
            1520                1525                1530

Val Leu Asp Gly Arg Gln Val Val Asp Met Arg Thr Asn Pro Gly
            1535                1540                1545

Asp Pro Arg Glu Ala Gln Glu Gln Gln Asn Asp Gly Lys Gly Arg
            1550                1555                1560

Gly Asn Lys Ala Ala Lys Arg Asp Leu Pro Pro Ala Lys Thr His
            1565                1570                1575

Leu Ile Gln Glu Asp Ile Leu Pro Tyr Cys Arg Pro Thr Phe Pro
            1580                1585                1590

Thr Ser Asn Asn Pro Arg Asp Pro Ser Ser Ser Ser Met Ser
            1595                1600                1605

Ser Arg Gly Ser Gly Ser Arg Gln Arg Glu Gln Ala Asn Val Gly
            1610                1615                1620
```

```
Arg Arg  Asn Ile Ala Glu Met  Gln Val Leu Gly Gly  Tyr Glu Arg
    1625             1630                 1635

Gly Glu  Asp Asn Asn Glu Glu  Leu Glu Glu Thr Glu  Ser
    1640             1645                 1650

<210> SEQ ID NO 17
<211> LENGTH: 1386
<212> TYPE: PRT
<213> ORGANISM: Homo sapiens

<400> SEQUENCE: 17

Met Leu Arg Tyr Leu Leu Lys Thr Leu Leu Gln Met Asn Leu Phe Ala
1               5                   10                  15

Asp Ser Leu Ala Gly Asp Ile Ser Asn Ser Ser Glu Leu Leu Leu Gly
            20                  25                  30

Phe Asn Ser Ser Leu Ala Ala Leu Asn His Thr Leu Leu Pro Pro Gly
        35                  40                  45

Asp Pro Ser Leu Asn Gly Ser Arg Val Gly Pro Glu Asp Ala Met Pro
    50                  55                  60

Arg Ile Val Glu Gln Pro Pro Asp Leu Leu Val Ser Arg Gly Glu Pro
65                  70                  75                  80

Ala Thr Leu Pro Cys Arg Ala Glu Gly Arg Pro Arg Pro Asn Ile Glu
                85                  90                  95

Trp Tyr Lys Asn Gly Ala Arg Val Ala Thr Val Arg Glu Asp Pro Arg
            100                 105                 110

Ala His Arg Leu Leu Leu Pro Ser Gly Ala Leu Phe Phe Pro Arg Ile
        115                 120                 125

Val His Gly Arg Arg Ala Arg Pro Asp Glu Gly Val Tyr Thr Cys Val
    130                 135                 140

Ala Arg Asn Tyr Leu Gly Ala Ala Ala Ser Arg Asn Ala Ser Leu Glu
145                 150                 155                 160

Val Ala Val Leu Arg Asp Asp Phe Arg Gln Ser Pro Gly Asn Val Val
                165                 170                 175

Val Ala Val Gly Glu Pro Ala Val Leu Glu Cys Val Pro Pro Arg Gly
            180                 185                 190

His Pro Glu Pro Ser Val Ser Trp Arg Lys Asp Gly Ala Arg Leu Lys
        195                 200                 205

Glu Glu Glu Gly Arg Ile Thr Ile Arg Gly Gly Lys Leu Met Met Ser
    210                 215                 220

His Thr Leu Lys Ser Asp Ala Gly Met Tyr Val Cys Val Ala Ser Asn
225                 230                 235                 240

Met Ala Gly Glu Arg Glu Ser Ala Ala Ala Glu Val Met Val Leu Glu
                245                 250                 255

Arg Pro Ser Phe Leu Arg Arg Pro Val Asn Gln Val Val Leu Ala Asp
            260                 265                 270

Ala Pro Val Thr Phe Leu Cys Glu Val Lys Gly Asp Pro Pro Pro Arg
        275                 280                 285

Leu Arg Trp Arg Lys Glu Asp Gly Glu Leu Pro Thr Gly Arg Tyr Glu
    290                 295                 300

Ile Arg Ser Asp His Ser Leu Trp Ile Gly His Val Ser Ala Glu Asp
305                 310                 315                 320

Glu Gly Thr Tyr Thr Cys Val Ala Glu Asn Ser Val Gly Arg Ala Glu
                325                 330                 335

Ala Ser Gly Ser Leu Ser Val His Val Pro Pro Gln Leu Val Thr Gln
```

```
                340                 345                 350
Pro Gln Asp Gln Met Ala Ala Pro Gly Glu Ser Val Ala Phe Gln Cys
            355                 360                 365
Glu Thr Lys Gly Asn Pro Pro Ala Ile Phe Trp Gln Lys Glu Gly
        370                 375                 380
Ser Gln Val Leu Leu Phe Pro Ser Gln Ser Leu Gln Pro Thr Gly Arg
385                 390                 395                 400
Phe Ser Val Ser Pro Arg Gly Gln Leu Asn Ile Thr Ala Val Gln Arg
                405                 410                 415
Gly Asp Ala Gly Tyr Tyr Val Cys Gln Ala Val Ser Val Ala Gly Ser
            420                 425                 430
Ile Leu Ala Lys Ala Leu Leu Glu Ile Lys Gly Ala Ser Leu Asp Gly
            435                 440                 445
Leu Pro Pro Val Ile Leu Gln Gly Pro Ala Asn Gln Thr Leu Val Leu
        450                 455                 460
Gly Ser Ser Val Trp Leu Pro Cys Arg Val Thr Gly Asn Pro Gln Pro
465                 470                 475                 480
Ser Val Arg Trp Lys Lys Asp Gly Gln Trp Leu Gln Gly Asp Asp Leu
                485                 490                 495
Gln Phe Lys Thr Met Ala Asn Gly Thr Leu Tyr Ile Ala Asn Val Gln
            500                 505                 510
Glu Met Asp Met Gly Phe Tyr Ser Cys Val Ala Lys Ser Ser Thr Gly
            515                 520                 525
Glu Ala Thr Trp Ser Gly Trp Leu Lys Met Arg Glu Asp Trp Gly Val
        530                 535                 540
Ser Pro Asp Pro Pro Thr Glu Pro Ser Ser Pro Gly Ala Pro Ser
545                 550                 555                 560
Gln Pro Val Val Thr Glu Ile Thr Lys Asn Ser Ile Thr Leu Thr Trp
                565                 570                 575
Lys Pro Asn Pro Gln Thr Gly Ala Ala Val Thr Ser Tyr Val Ile Glu
            580                 585                 590
Ala Phe Ser Pro Ala Ala Gly Asn Thr Trp Arg Thr Val Ala Asp Gly
            595                 600                 605
Val Gln Leu Glu Thr His Thr Val Ser Gly Leu Gln Pro Asn Thr Ile
        610                 615                 620
Tyr Leu Phe Leu Val Arg Ala Val Gly Ala Trp Gly Leu Ser Glu Pro
625                 630                 635                 640
Ser Pro Val Ser Glu Pro Val Arg Thr Gln Asp Ser Ser Pro Ser Arg
                645                 650                 655
Pro Val Glu Asp Pro Trp Arg Gly Gln Gln Gly Leu Ala Glu Val Ala
            660                 665                 670
Val Arg Leu Gln Glu Pro Ile Val Leu Gly Pro Arg Thr Leu Gln Val
            675                 680                 685
Ser Trp Thr Val Asp Gly Pro Val Gln Leu Val Gln Gly Phe Arg Val
        690                 695                 700
Ser Trp Arg Val Ala Gly Pro Glu Gly Gly Ser Trp Thr Met Leu Asp
705                 710                 715                 720
Leu Gln Ser Pro Ser Gln Gln Ser Thr Val Leu Arg Gly Leu Pro Pro
                725                 730                 735
Gly Thr Gln Ile Gln Ile Lys Val Gln Ala Gln Gly Gln Glu Gly Leu
            740                 745                 750
Gly Ala Glu Ser Leu Ser Val Thr Arg Ser Ile Pro Glu Glu Ala Pro
            755                 760                 765
```

```
Ser Gly Pro Pro Gln Gly Val Ala Val Ala Leu Gly Gly Asp Gly Asn
    770                 775                 780

Ser Ser Ile Thr Val Ser Trp Glu Pro Pro Leu Pro Ser Gln Gln Asn
785                 790                 795                 800

Gly Val Ile Thr Glu Tyr Gln Ile Trp Cys Leu Gly Asn Glu Ser Arg
                805                 810                 815

Phe His Leu Asn Arg Ser Ala Ala Gly Trp Ala Arg Ser Ala Met Leu
                820                 825                 830

Arg Gly Leu Val Pro Gly Leu Leu Tyr Arg Thr Leu Val Ala Ala Ala
                835                 840                 845

Thr Ser Ala Gly Val Gly Val Pro Ser Ala Pro Val Leu Val Gln Leu
    850                 855                 860

Pro Ser Pro Pro Asp Leu Glu Pro Gly Leu Glu Val Gly Ala Gly Leu
865                 870                 875                 880

Ala Val Arg Leu Ala Arg Val Leu Arg Glu Pro Ala Phe Leu Ala Gly
                885                 890                 895

Ser Gly Ala Ala Cys Gly Ala Leu Leu Leu Gly Leu Cys Ala Ala Leu
                900                 905                 910

Tyr Trp Arg Arg Lys Gln Arg Lys Glu Leu Ser His Tyr Thr Ala Ser
                915                 920                 925

Phe Ala Tyr Thr Pro Ala Val Ser Phe Pro His Ser Glu Gly Leu Ser
    930                 935                 940

Gly Ala Ser Ser Arg Pro Pro Met Gly Leu Gly Pro Ala Pro Tyr Ser
945                 950                 955                 960

Trp Leu Ala Asp Ser Trp Pro His Pro Ser Arg Ser Pro Ser Ala Gln
                965                 970                 975

Glu Pro Arg Gly Ser Cys Cys Pro Ser Asn Pro Asp Pro Asp Asp Arg
                980                 985                 990

Tyr Tyr Asn Glu Ala Gly Ile Ser  Leu Tyr Leu Ala Gln  Thr Ala Arg
                995                 1000                1005

Gly Thr  Ala Ala Pro Gly Glu  Gly Pro Val Tyr Ser  Thr Ile Asp
    1010                1015                1020

Pro Ala  Gly Glu Glu Leu Gln  Thr Phe His Gly Gly  Phe Pro Gln
    1025                1030                1035

His Pro  Ser Gly Asp Leu Gly  Pro Trp Ser Gln Tyr  Ala Pro Pro
    1040                1045                1050

Glu Trp  Ser Gln Gly Asp Ser  Gly Ala Lys Gly Lys  Lys Val Lys
    1055                1060                1065

Leu Leu  Gly Lys Pro Val Gln  Met Pro Ser Leu Asn  Trp Pro Glu
    1070                1075                1080

Ala Leu  Pro Pro Pro Pro Pro  Ser Cys Glu Leu Ser  Cys Leu Glu
    1085                1090                1095

Gly Pro  Glu Glu Glu Leu Glu  Gly Ser Ser Glu Pro  Glu Glu Trp
    1100                1105                1110

Cys Pro  Pro Met Pro Glu Arg  Ser His Leu Thr Glu  Pro Ser Ser
    1115                1120                1125

Ser Gly  Gly Cys Leu Val Thr  Pro Ser Arg Arg Glu  Thr Pro Ser
    1130                1135                1140

Pro Thr  Pro Ser Tyr Gly Gln  Gln Ser Thr Ala Thr  Leu Thr Pro
    1145                1150                1155

Ser Pro  Pro Asp Pro Pro Gln  Pro Pro Thr Asp Met  Pro His Leu
    1160                1165                1170
```

```
His Gln Met Pro Arg Arg Val Pro Leu Gly Pro Ser  Ser Pro Leu
    1175                1180                1185

Ser Val Ser Gln Pro Met Leu Gly Ile Arg Glu Ala  Arg Pro Ala
    1190                1195                1200

Gly Leu Gly Ala Gly Pro Ala Ala Ser Pro His Leu  Ser Pro Ser
    1205                1210                1215

Pro Ala Pro Ser Thr Ala Ser Ser Ala Pro Gly Arg  Thr Trp Gln
    1220                1225                1230

Gly Asn Gly Glu Met Thr Pro Pro Leu Gln Gly Pro  Arg Ala Arg
    1235                1240                1245

Phe Arg Lys Lys Pro Lys Ala Leu Pro Tyr Arg Arg  Glu Asn Ser
    1250                1255                1260

Pro Gly Asp Leu Pro Pro Pro Leu Pro Pro Pro Pro  Glu Glu Glu
    1265                1270                1275

Ala Ser Trp Ala Leu Glu Leu Arg Ala Ala Gly Ser  Met Ser Ser
    1280                1285                1290

Leu Glu Arg Glu Arg Ser Gly Glu Arg Lys Ala Val  Gln Ala Val
    1295                1300                1305

Pro Leu Ala Ala Gln Arg Val Leu His Pro Asp Glu  Glu Ala Trp
    1310                1315                1320

Leu Pro Tyr Ser Arg Pro Ser Phe Leu Ser Arg Gly  Gln Gly Thr
    1325                1330                1335

Ser Thr Cys Ser Thr Ala Gly Ser Asn Ser Ser Arg  Gly Ser Ser
    1340                1345                1350

Ser Ser Arg Gly Ser Arg Gly Pro Gly Arg Ser Arg  Ser Arg Ser
    1355                1360                1365

Gln Ser Arg Ser Gln Ser Gln Arg Pro Gly Gln Lys  Arg Arg Glu
    1370                1375                1380

Glu Pro Arg
    1385

<210> SEQ ID NO 18
<211> LENGTH: 12
<212> TYPE: PRT
<213> ORGANISM: Artificial sequence
<220> FEATURE:
<223> OTHER INFORMATION: Robo receptor ectodomain D3 dimerization
      interface amino acid sequence

<400> SEQUENCE: 18

Lys Lys Asp Asp Ala Asp Leu Pro Arg Gly Arg Tyr
1               5                   10

<210> SEQ ID NO 19
<211> LENGTH: 12
<212> TYPE: PRT
<213> ORGANISM: Artificial sequence
<220> FEATURE:
<223> OTHER INFORMATION: Robo receptor ectodomain D3 dimerization
      interface amino acid sequence

<400> SEQUENCE: 19

Arg Lys Asp Asp Gly Glu Leu Pro Lys Ser Arg Tyr
1               5                   10

<210> SEQ ID NO 20
<211> LENGTH: 12
<212> TYPE: PRT
<213> ORGANISM: Artificial sequence
<220> FEATURE:
```

<223> OTHER INFORMATION: Robo receptor ectodomain D3 dimerization
      interface amino acid sequence

<400> SEQUENCE: 20

Arg Lys Glu Asp Gly Glu Leu Pro Thr Gly Arg Tyr
1               5                   10

<210> SEQ ID NO 21
<211> LENGTH: 5
<212> TYPE: PRT
<213> ORGANISM: Homo sapiens

<400> SEQUENCE: 21

Pro Arg Asp Gln Ile
1               5

<210> SEQ ID NO 22
<211> LENGTH: 9
<212> TYPE: PRT
<213> ORGANISM: Homo sapiens

<400> SEQUENCE: 22

Gln Asn Leu Leu Phe Pro Asn Gln Pro
1               5

<210> SEQ ID NO 23
<211> LENGTH: 9
<212> TYPE: PRT
<213> ORGANISM: Homo sapiens

<400> SEQUENCE: 23

Ser Arg Cys Ser Val Ser Pro Thr Gly
1               5

<210> SEQ ID NO 24
<211> LENGTH: 9
<212> TYPE: PRT
<213> ORGANISM: Homo sapiens

<400> SEQUENCE: 24

Ala Gly Tyr Tyr Ile Cys Gln Ala Leu
1               5

<210> SEQ ID NO 25
<211> LENGTH: 12
<212> TYPE: PRT
<213> ORGANISM: Homo sapiens

<400> SEQUENCE: 25

Glu Phe Arg Cys Gln Val Gln Gly Asp Pro Gln Pro
1               5                   10

<210> SEQ ID NO 26
<211> LENGTH: 89
<212> TYPE: PRT
<213> ORGANISM: Homo sapiens

<400> SEQUENCE: 26

Met Val Gly Glu Arg Asp Ser Asp Pro Ala Glu Leu Thr Val Phe Glu
1               5                   10                  15

Arg Pro Thr Phe Leu Arg Arg Pro Ile Asn Gln Val Val Leu Glu Glu
            20                  25                  30

Glu Ala Val Glu Phe Arg Cys Gln Val Gln Gly Asp Pro Gln Pro Thr
        35                  40                  45

Val Arg Trp Lys Lys Asp Asp Ala Asp Leu Pro Arg Gly Arg Tyr Asp
 50                  55                  60

Ile Lys Asp Asp Tyr Thr Leu Arg Ile Lys Lys Thr Met Ser Thr Asp
 65                  70                  75                  80

Glu Gly Thr Tyr Met Cys Ile Ala Glu
                 85

<210> SEQ ID NO 27
<211> LENGTH: 64
<212> TYPE: PRT
<213> ORGANISM: Artificial sequence
<220> FEATURE:
<223> OTHER INFORMATION: D4 dimerization interface Amino acid sequence
<220> FEATURE:
<221> NAME/KEY: MISC_FEATURE
<222> LOCATION: (7)..(7)
<223> OTHER INFORMATION: selected from the group consisting of Valine
      and Isoleucine
<220> FEATURE:
<221> NAME/KEY: MISC_FEATURE
<222> LOCATION: (10)..(10)
<223> OTHER INFORMATION: selected from the group consisting of Glutamine
      and Arginine
<220> FEATURE:
<221> NAME/KEY: MISC_FEATURE
<222> LOCATION: (11)..(11)
<223> OTHER INFORMATION: selected from the group consisting of Lysine
      and Arginine
<220> FEATURE:
<221> NAME/KEY: MISC_FEATURE
<222> LOCATION: (16)..(16)
<223> OTHER INFORMATION: selected from the group consisting of
      Asparagine and Valine
<220> FEATURE:
<221> NAME/KEY: MISC_FEATURE
<222> LOCATION: (20)..(20)
<223> OTHER INFORMATION: selected from the group consisting of Proline
      and Serine
<220> FEATURE:
<221> NAME/KEY: MISC_FEATURE
<222> LOCATION: (21)..(21)
<223> OTHER INFORMATION: selected from the group consisting of
      Asparagine, Tyrosine and Serine
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (42)..(43)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid

```
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: MISC_FEATURE
<222> LOCATION: (55)..(55)
<223> OTHER INFORMATION: selected from the group consisting of Alanine
      and Threonine
<220> FEATURE:
<221> NAME/KEY: MISC_FEATURE
<222> LOCATION: (56)..(56)
<223> OTHER INFORMATION: selected from the group consisting of Leucine
      and Valine
<220> FEATURE:
<221> NAME/KEY: MISC_FEATURE
<222> LOCATION: (57)..(57)
<223> OTHER INFORMATION: selected from the group consisting of
      Threonine, Asparagine and Serine
<220> FEATURE:
<221> NAME/KEY: MISC_FEATURE
<222> LOCATION: (64)..(64)
<223> OTHER INFORMATION: selected from the group consisting of Alanine
      and Threonine

<400> SEQUENCE: 27

Gly Asn Pro Gln Pro Ala Xaa Phe Trp Xaa Xaa Glu Gly Ser Gln Xaa
1               5                   10                  15

Leu Leu Phe Xaa Xaa Gln Pro Xaa Gln Xaa Xaa Xaa Arg Xaa Ser Val
            20                  25                  30

Ser Xaa Xaa Gly Xaa Leu Xaa Ile Thr Xaa Xaa Gln Arg Xaa Asp Xaa
        35                  40                  45

Gly Tyr Tyr Xaa Cys Gln Xaa Xaa Xaa Val Ala Gly Ser Ile Leu Xaa
    50                  55                  60

<210> SEQ ID NO 28
<211> LENGTH: 7
<212> TYPE: PRT
<213> ORGANISM: Artificial sequence
<220> FEATURE:
<223> OTHER INFORMATION: hRobo2 receptor ectodomain D4-D5partial
      sequence - 7-residuelong coil

<400> SEQUENCE: 28

Asp Val Leu Thr Asp Arg Pro
1               5

<210> SEQ ID NO 29
<211> LENGTH: 4
<212> TYPE: PRT
<213> ORGANISM: Artificial sequence
<220> FEATURE:
<223> OTHER INFORMATION: partial amino acid sequence of the hRobo2 D3 CD
      loop

<400> SEQUENCE: 29

Asp Asp Ala Asp
1

<210> SEQ ID NO 30
<211> LENGTH: 4
<212> TYPE: PRT
<213> ORGANISM: Artificial sequence
<220> FEATURE:
<223> OTHER INFORMATION: partial amino acid sequence of the mutated form
      of hRobo2 D3 CD loop
```

<400> SEQUENCE: 30

Ser Lys Ala Lys
1

<210> SEQ ID NO 31
<211> LENGTH: 64
<212> TYPE: PRT
<213> ORGANISM: Homo sapiens

<400> SEQUENCE: 31

Gly Asn Pro Gln Pro Ala Val Phe Trp Gln Lys Glu Gly Ser Gln Asn
1               5                   10                  15

Leu Leu Phe Pro Asn Gln Pro Gln Gln Pro Asn Ser Arg Cys Ser Val
            20                  25                  30

Ser Pro Thr Gly Asp Leu Thr Ile Thr Asn Ile Gln Arg Ser Asp Ala
        35                  40                  45

Gly Tyr Tyr Ile Cys Gln Ala Leu Thr Val Ala Gly Ser Ile Leu Ala
    50                  55                  60

<210> SEQ ID NO 32
<211> LENGTH: 64
<212> TYPE: PRT
<213> ORGANISM: Homo sapiens

<400> SEQUENCE: 32

Gly Asn Pro Gln Pro Ala Ile Phe Trp Arg Arg Glu Gly Ser Gln Asn
1               5                   10                  15

Leu Leu Phe Ser Tyr Gln Pro Pro Gln Ser Ser Ser Arg Phe Ser Val
            20                  25                  30

Ser Gln Thr Gly Asp Leu Thr Ile Thr Asn Val Gln Arg Ser Asp Val
        35                  40                  45

Gly Tyr Tyr Ile Cys Gln Thr Leu Asn Val Ala Gly Ser Ile Ile Thr
    50                  55                  60

<210> SEQ ID NO 33
<211> LENGTH: 64
<212> TYPE: PRT
<213> ORGANISM: Homo sapiens

<400> SEQUENCE: 33

Gly Asn Pro Pro Pro Ala Ile Phe Trp Gln Lys Glu Gly Ser Gln Val
1               5                   10                  15

Leu Leu Phe Pro Ser Gln Ser Leu Gln Pro Thr Gly Arg Phe Ser Val
            20                  25                  30

Ser Pro Arg Gly Gln Leu Asn Ile Thr Ala Val Gln Arg Gly Asp Ala
        35                  40                  45

Gly Tyr Tyr Val Cys Gln Ala Val Ser Val Ala Gly Ser Ile Leu Ala
    50                  55                  60

<210> SEQ ID NO 34
<211> LENGTH: 64
<212> TYPE: PRT
<213> ORGANISM: Artificial sequence
<220> FEATURE:
<223> OTHER INFORMATION: Robo receptor ectodomain D4 dimerization
      interface comprises the amino acid sequence
<220> FEATURE:
<221> NAME/KEY: MISC_FEATURE
<222> LOCATION: (7)..(7)
<223> OTHER INFORMATION: selected from the group consisting of Valine
      and Isoleucine

```
<220> FEATURE:
<221> NAME/KEY: MISC_FEATURE
<222> LOCATION: (10)..(10)
<223> OTHER INFORMATION: selected from the group consisting of Glutamine
      and Arginine
<220> FEATURE:
<221> NAME/KEY: MISC_FEATURE
<222> LOCATION: (11)..(11)
<223> OTHER INFORMATION: selected from the group consisting of Lysine
      and Arginine
<220> FEATURE:
<221> NAME/KEY: MISC_FEATURE
<222> LOCATION: (16)..(16)
<223> OTHER INFORMATION: selected from the group consisting of
      Asparagine and Valine
<220> FEATURE:
<221> NAME/KEY: MISC_FEATURE
<222> LOCATION: (20)..(20)
<223> OTHER INFORMATION: selected from the group consisting of Proline
      and Serine
<220> FEATURE:
<221> NAME/KEY: MISC_FEATURE
<222> LOCATION: (21)..(21)
<223> OTHER INFORMATION: selected from the group consisting of
      Asparagine, Tyrosine and Serine
<220> FEATURE:
<221> NAME/KEY: MISC_FEATURE
<222> LOCATION: (24)..(24)
<223> OTHER INFORMATION: selected from the group consisting of
      Glutamine, proline and Leucine
<220> FEATURE:
<221> NAME/KEY: MISC_FEATURE
<222> LOCATION: (26)..(26)
<223> OTHER INFORMATION: selected from the group consisting of Proline
      and Serine
<220> FEATURE:
<221> NAME/KEY: MISC_FEATURE
<222> LOCATION: (27)..(27)
<223> OTHER INFORMATION: selected from the group consisting of
      Asparagine, Serine and threonine
<220> FEATURE:
<221> NAME/KEY: MISC_FEATURE
<222> LOCATION: (28)..(28)
<223> OTHER INFORMATION: selected from the group consisting of Glycine
      and Serine
<220> FEATURE:
<221> NAME/KEY: MISC_FEATURE
<222> LOCATION: (30)..(30)
<223> OTHER INFORMATION: selected from the group consisting of Cysteine
      and Phenylalanine
<220> FEATURE:
<221> NAME/KEY: MISC_FEATURE
<222> LOCATION: (34)..(34)
<223> OTHER INFORMATION: selected from the group consisting of Proline
      and Glutamine
<220> FEATURE:
<221> NAME/KEY: MISC_FEATURE
<222> LOCATION: (35)..(35)
<223> OTHER INFORMATION: selected from the group consisting of Threonine
      and Arginine
<220> FEATURE:
<221> NAME/KEY: MISC_FEATURE
<222> LOCATION: (37)..(37)
<223> OTHER INFORMATION: selected from the group consisting of Aspartic
      acid and Glutamine
<220> FEATURE:
<221> NAME/KEY: MISC_FEATURE
<222> LOCATION: (39)..(39)
<223> OTHER INFORMATION: selected from the group consisting of Threonine
      and Asparagine
<220> FEATURE:
<221> NAME/KEY: MISC_FEATURE
<222> LOCATION: (42)..(42)
<223> OTHER INFORMATION: selected from the group consisting of Alanine
      and Asparagine
<220> FEATURE:
<221> NAME/KEY: MISC_FEATURE
<222> LOCATION: (43)..(43)
<223> OTHER INFORMATION: selected from the group consisting of
```

```
        Isoleucine and Valine
<220> FEATURE:
<221> NAME/KEY: MISC_FEATURE
<222> LOCATION: (46)..(46)
<223> OTHER INFORMATION: selected from the group consisting of Serine
      and Glycine
<220> FEATURE:
<221> NAME/KEY: MISC_FEATURE
<222> LOCATION: (48)..(48)
<223> OTHER INFORMATION: selected from the group consisting of Valine
      and Alanine
<220> FEATURE:
<221> NAME/KEY: MISC_FEATURE
<222> LOCATION: (52)..(52)
<223> OTHER INFORMATION: selected from the group consisting of Valine
      and Isoleucine
<220> FEATURE:
<221> NAME/KEY: MISC_FEATURE
<222> LOCATION: (55)..(55)
<223> OTHER INFORMATION: selected from the group consisting of Alanine
      and Threonine
<220> FEATURE:
<221> NAME/KEY: MISC_FEATURE
<222> LOCATION: (56)..(56)
<223> OTHER INFORMATION: selected from the group consisting of Leucine
      and Valine
<220> FEATURE:
<221> NAME/KEY: MISC_FEATURE
<222> LOCATION: (57)..(57)
<223> OTHER INFORMATION: selected from the group consisting of
      Threonine, Asparagine and Serine
<220> FEATURE:
<221> NAME/KEY: MISC_FEATURE
<222> LOCATION: (64)..(64)
<223> OTHER INFORMATION: selected from the group consisting of Alanine
      and Threonine

<400> SEQUENCE: 34

Gly Asn Pro Gln Pro Ala Xaa Phe Trp Xaa Xaa Glu Gly Ser Gln Xaa
1               5                   10                  15

Leu Leu Phe Xaa Xaa Gln Pro Xaa Gln Xaa Xaa Xaa Arg Xaa Ser Val
            20                  25                  30

Ser Xaa Xaa Gly Xaa Leu Xaa Ile Thr Xaa Xaa Gln Arg Xaa Asp Xaa
        35                  40                  45

Gly Tyr Tyr Xaa Cys Gln Xaa Xaa Xaa Val Ala Gly Ser Ile Leu Xaa
    50                  55                  60

<210> SEQ ID NO 35
<211> LENGTH: 837
<212> TYPE: DNA
<213> ORGANISM: Artificial sequence
<220> FEATURE:
<223> OTHER INFORMATION: AbD32836 Fd chain nucleic acid sequence

<400> SEQUENCE: 35
gaagtgcaat tggtggaaag cggcggtggc ctggtgaaac aggcggcag cctgcgcctg        60 agctgcgccg cctccggatt cacctttcct tcttacgctc tgtcttgggt gcgccaggcc     120
ccgggcaaag gtctcgagtg gtgggccat atcaaatcta aaactgacgg tggtgctact      180
gaatatgccg ccccagtgaa aggccgcttt accattagcc gcgatgattc gaaaaacacc     240
ctgtatctgc aaatgaacag cctgaaaacc gaagatacgg ccgtgtatta ttgcgcgcgt     300
tcttactctg aatacatccc gctgtacgct ttcgctgttt ggggccaagg caccctggtg     360
actgttagct cagcgtcgac caaaggcccg agcgtgtttc cgctggcccc gagcagcaaa     420
agcaccagcg gcggcaccgc cgcactgggc tgcctggtga agattattt cccgaaacca     480 gtgaccgtga gctggaacag cggtgccctg accagcggcg tgcataccct tccggcggtg     540
```

-continued

```
ctgcaaagca gcggcctgta tagcctgagc agcgttgtga ccgtgccgag cagcagcctg    600
ggcacccaga cctatatttg caacgtcaac cataaaccga gcaacaccaa agtcgataaa    660
aaagtcgaac cgaaaagcga attcggtggc gcgccgggca aaccgattcc gaatccgctg    720
ctgggcctgg atagcaccga tgcgccgagc gcgtggagcc atccgcagtt tgaaaaaggt    780
ggcggttctg gtggcggttc tggtggctcc gcgtggtcgc atccacaatt cgagaag      837
```

<210> SEQ ID NO 36
<211> LENGTH: 645
<212> TYPE: DNA
<213> ORGANISM: Artificial sequence
<220> FEATURE:
<223> OTHER INFORMATION: AbD32836 Light chain nucleic acid sequence
<400> SEQUENCE: 36

```
gatatcgtgc tgacccagcc gccgagcgtg agcggtgcac cgggccagcg cgtgaccatt     60
agctgtagcg gcagcagcag caacattggt tctaaatacg tgtcttggta ccagcagctg    120
ccgggcacgg cgccgaaact gctgatctac tacacttctc agcgcccgag cggcgtgccg    180
gatcgcttta gcggatccaa aagcggcacc agcgccagcc tggcgattac cggcctgcaa    240
gcagaagacg aagcggatta ttactgctac gcttgggact ctacttctac ttctactgtg    300
tttggcggcg gcacgaagtt aaccgttctt ggccagccga agccgccccc aagcgtgacc    360
ctgtttccgc cgagcagcga agaactgcaa gccaacaaag ccaccctggt ttgcctgatc    420
agcgattttt atccgggtgc cgtgaccgtg gcctggaaag ccgatagcag cccggtgaaa    480
gccggcgtgg aaaccaccac cccgagcaaa cagagcaaca caaatatgc cgccagcagc     540 tatctgagcc tgacccggg acagtggaaa agccatcgca gctatagttg tcaagtgacc    600
catgaaggca gcaccgtgga aaaaaccgtg gccccgaccg aggcc                   645
```

ROUNDABOUT (ROBO) RECEPTOR INHIBITORS AND USES THEREOF

RELATED APPLICATIONS

This application is a National Phase of PCT Patent Application No. PCT/IL2018/050936 having International filing date of Aug. 24, 2018, which claims the benefit of priority under 35 USC § 119(e) of U.S. Provisional Patent Application No. 62/549,472 filed on Aug. 24, 2017. The contents of the above applications are all incorporated by reference as if fully set forth herein in their entirety.

SEQUENCE LISTING STATEMENT

The ASCII file, entitled 81838SequenceListing.txt, created on Feb. 24, 2020, comprising 120,719 bytes, submitted concurrently with the filing of this application is incorporated herein by reference. The sequence listing submitted herewith is identical to the sequence listing forming part of the international application.

FIELD AND BACKGROUND OF THE INVENTION

First discovered in a *Drosophila* screen for axonal-guidance defects, Robo receptors were later identified as cognate receptors for the Slit secreted guidance factors. In development, Robo receptors are best known for their role in axon navigation at the ventral midline of the nerve cord, where Robo repulsive signaling prevents repeated midline crossing of commissural axons. Besides their role in axonal guidance, Robo receptors participate in regulating several other functions of migrating and non-migrating cells, including neuronal precursor and muscle cells and the organogenesis of lungs, kidneys, heart, diaphragm and bone.

Humans have three Slits (hSlit1-3), three long Robo receptors (hRobo1-3), and one shorter Robo (hRobo4) paralog. In mammals, Slit ligands bind to Robo1 and 2, but not to Robo3, with high affinity, indicating that different ligands or co-receptors may activate Robo3. Robo1, 2 and 3 have similar domain architecture, with eight extracellular domains (D1-D8): five N-terminal Ig-like domains (D1-D5), and three fibronectin (Fn) type-3 (FnIII) domains (D6-D8). The Ig and FnIII domains are followed by a short extracellular juxtamembrane (JM) linker, a single-pass transmembrane segment, and a largely-unstructured intracellular segment, to which enzymatic effectors bind (FIG. 1). Effectors binding the intracellular segment include the actin binding proteins Ena and Canoe/AF-6, the tyrosine kinase Abelson (Abl), the Ras/Rho GEF Son of Sevenless (SOS), and the Rac1/RhoA/CDC42 activating SRGAP proteins. It is thought that Robo signaling is triggered by ligand (e.g. Slit) binding to the extracellular portion of the receptor (ectodomains). Ligand binding to the extracellular portion of Robo stimulates Robo for the recruitment and/or the activation of cytoplasmic effectors that bind to specific conserved motifs within the Robo intracellular domain.

A crystal structure of the complex between the high-affinity interacting domains of Slit (domain 2) and Robo (D1) (pdb 2V9T) reveals the contact surfaces and chemical properties of the major Slit-Robo interaction. It is unclear whether Slit itself is a dimer, through which Robo can also dimerize, and although some Slit segments form dimers, it was also reported that a larger Slit segment is in fact a monomer.

It has been suggested that dimerization plays a role in Robo activation and signaling (Blockus and Chedotal, 2016; Dickson and Gilestro, 2006; Seiradake et al., 2016). Chimera constructs of the intracellular portion of Robo1 fused to the ectodomains of either one of the receptor tyrosine kinases (RTKs) Met and TrkA, elicited characteristic repulsion responses when stimulated by the RTKs' cognate dimerization-inducing ligands (Stein and Tessier-Lavigne, 2001). Additional reports have shown that *Drosophila* Robo1 and Robo2 interact through their extracellular Ig domains (Evans and Bashaw, 2010). Mammalian Robo1, Robo2, and Robo3 were also shown to participate in homotypic and heterotypic interactions (Hivert et al., 2002; Liu et al., 2004; Mambetisaeva et al., 2005 and Sheldon et al., 2009). FRET measurements (Zakrys et al., 2014) have shown that eGFP-tagged recombinant mouse Robo1 exists in a monomer-dimer equilibrium in live cell membranes, concluding that the five Ig domains (D1-D5) are important for dimerization.

Approaches to inhibit the activities of Robo receptors have been described. One is the use of soluble fragments of Robo receptors that include the Slit binding Ig domain 1 (D1) to block Slit and prevent it from binding to- and activating transmembrane endogenic Robo receptors (for example in (Liu et al., 2004; Patel et al., 2001) and in patent publications numbers PCT/US2013/020280 and PCT/FR2011/050811). In another approach, antibodies directed against the Slit-binding D1 of Robo were used to prevent Slit-Robo interaction and Robo stimulation (for example in (Wang et al., 2003; Zhao et al., 2016). However, the high affinity (nano-molar $K_D$) of Slit-Robo interactions, and the high local concentration of Slit at its signaling sites probably diminish the effectiveness of Robo inhibition by means of competing with Slit for Robo1 binding, especially in vivo.

Additional relevant publications include PCT publication WO2011/134420 to Geng et al, US patent publication US 2015/0037325 to Lu et al, US patent publications 2010/0233819, 2009/0155928 and PCT publication WO1999/020764 to Goodman et al., US patent publication 2013/0039912 to Blanche and US patent publication 2013/0143320 to Li.

SUMMARY OF THE INVENTION

According to an aspect of some embodiments of the present invention there is provided an agent capable of specifically binding to a Robo receptor ectodomain polypeptide selected from the group consisting of a Robo receptor Immunoglobulin-like domain 3 (D3), a Robo receptor Immunoglobulin-like domain 4 (D4), a Robo receptor Immunoglobulin-like domain 5 (D5), a Robo receptor Fibronectin type III domain 1 (FnIII-1)(D6), a Robo receptor Fibronectin type III domain 2 (FnIII-2)(D7), a Robo receptor Fibronectin type III domain 3 (FnIII-3)(D8), a Robo receptor D3-D4 hinge region, a Robo receptor D4-D5 hinge region, a Robo receptor D5-D6 hinge region, a Robo receptor D6-D7 hinge region and a Robo receptor D7-D8 hinge region, or a portion thereof, and inhibiting Robo receptor dimerization.

According to some embodiments of the invention the agent comprising a moiety which specifically binds a Robo receptor ectodomain polypeptide selected from the group consisting of Robo receptor Immunoglobulin-like domain 3 (D3), a Robo receptor Immunoglobulin-like domain 4 (D4), a Robo receptor Immunoglobulin-like domain 5 (D5), a Robo receptor Fibronectin type III domain 1 (FnIII-1)(D6), a Robo receptor Fibronectin type III domain 2 (FnIII-2)(D7) and a Robo receptor Fibronectin type III domain 3 (FnIII-3)(D8).

According to some embodiments of the invention the agent does not bind any of Robo receptor D1 or D2.

According to some embodiments of the invention the agent is further capable of inhibiting homo-dimerization of an isolated Robo receptor D4-D5 polypeptide.

According to some embodiments of the invention the agent is further capable of inhibiting homo-dimerization of an isolated Robo receptor D4 polypeptide.

According to some embodiments of the invention the agent is further capable of inhibiting homo-dimerization of an isolated Robo receptor D1-D3 polypeptide.

According to some embodiments of the invention the agent is further capable of inhibiting homo-dimerization of an isolated Robo receptor D3 polypeptide.

According to some embodiments of the invention the binding is characterized by a micromolar or sub-micromolar dissociation constant ($K_D$).

According to some embodiments of the invention the binding is characterized by a dissociation constant in the range of 10 nM-5000 nM.

According to some embodiments of the invention the binding is characterized by a dissociation constant in the range of 10-250 nM.

According to some embodiments of the invention the binding is characterized by a dissociation constant in the range of 10-100 nM.

According to some embodiments of the invention the agent of the invention comprises a moiety binding to Robo receptor ectodomain D4-D4 dimerization interface.

According to some embodiments of the invention the moiety binds to ectodomain D4-D4 dimerization interface or a portion thereof, wherein the binding inhibits Robo receptor D4-D4 dimerization and wherein the agent does not bind either of Robo receptor D1 or D2 or D1-D2 hinge region.

According to some embodiments of the invention the moiety binds to a Robo sequence selected from the group consisting of Robo2(336-340), Robo2(369-377), Robo2 (382-390), Robo 2(402-410) of human Robo2 or the Robo receptor ectodomain D4 dimerization interface of Robo, wherein the binding inhibits Robo receptor D4-D4 dimerization.

According to some embodiments of the invention the Robo receptor ectodomain D4 dimerization interface comprises the amino acid sequence as set forth in SEQ ID NO: 34.

According to some embodiments of the invention the Robo receptor ectodomain D4 dimerization interface comprises the amino acid sequence as set forth in SEQ ID NO: 31.

According to some embodiments of the invention the moiety binds to Robo receptor ectodomain D3-D3 dimerization interface.

According to some embodiments of the invention the moiety binds to ectodomain D3-D3 dimerization interface or a portion thereof, wherein the binding inhibits Robo receptor D3-D3 dimerization and wherein the agent does not bind either of Robo receptor D1 or D2 or D1-D2 hinge region.

According to some embodiments of the invention the moiety binds to Robo sequence selected from the group consisting of Robo2(259-KKDDADLPRGRY SEQ ID NO: 18), Robo 1(296-RKDDGALPKSRY SEQ ID NO: 19), Robo3(292-RKEDGELPTGRY, SEQ ID NO: 20) of human Robo or the Robo receptor ectodomain D3 dimerization interface of Robo, wherein the binding inhibits Robo receptor D3-D3 dimerization.

According to some embodiments of the invention the Robo receptor ectodomain D3 dimerization interface comprises the amino acid sequence as set forth in SEQ ID NO: 18.

According to some embodiments of the invention binding to said Robo receptor ectodomain D3 inhibits intracellular signaling via Robo receptor intracellular domain.

According to some embodiments of the invention the binding to the Robo receptor ectodomain D3 or D4 inhibits intracellular signaling via Robo receptor intracellular domain.

According to some embodiments of the invention the inhibiting of intracellular signaling via Robo receptor intracellular domain comprises inhibiting Robo recruitment of intracellular protein effectors.

According to some embodiments of the invention, the inhibiting intracellular signaling via Robo receptor intracellular domain is selected from the group consisting of inhibiting Robo receptor internalization, inhibiting Robo receptor phosphorylation and inhibiting Robo receptor dephosphorylation.

According to some embodiments of the invention the agent is selected from the group consisting of an antibody, a peptide, a polypeptide, a peptidomimetic, a DNA, an RNA, an aptamer (DNA/RNA), a peptoid, a zDNA, a peptide nucleic acid (PNA), a locked nucleic acid (LNA), a lectin, an adnectin and a dendrimer.

According to some embodiments of the invention the Robo receptor ectodomain is a human Robo receptor ectodomain.

According to some embodiments of the invention the said human Robo receptor ectodomain is selected from the group consisting of a human Robo1 ectodomain, a human Robo 2 ectodomain and a human Robo3 ectodomain.

According to some embodiments of the invention the human Robo receptor ectodomain is a human Robo2 ectodomain.

According to some embodiments of the invention there is provided a nucleic acid sequence encoding the agent, wherein the agent is a peptide or polypeptide agent.

According to some embodiments of the invention there is provided a pharmaceutical composition comprising the agent of the invention and a pharmaceutically acceptable carrier.

According to some embodiments of the invention there is provided the agent for use in treating a Robo receptor associated condition or disorder.

According to some embodiments of the invention the Robo receptor associated condition or disorder is a fibrotic condition or disorder.

According to some embodiments of the invention the fibrotic disorder is selected from the group consisting of liver fibrosis and kidney fibrosis.

According to some embodiments of the invention the Robo receptor associated condition or disorder is a cancer.

According to some embodiments of the invention the cancer is tumor angiogenesis and/or metastatic cancer.

According to some embodiments of the invention the Robo receptor associated condition or disorder is a neurological condition or disorder.

According to some embodiments of the invention the Robo receptor associated condition or disorder is an orthopedic condition or disorder.

According to an aspect of some embodiments of the present invention there is provided a method of identifying an agent for inhibiting Robo receptor activation comprising: contacting candidate agents with a Robo receptor ectodomain polypeptide comprising a Robo receptor Immunoglobulin-like domain 3 (D3), Robo receptor Immunoglobulin-like domain 4 (D4), a Robo receptor Immunoglobulin-like domain 5 (D5), a Robo receptor Fibronectin type III domain 1 (FnIII-1)(D6), a Robo receptor Fibronectin type III domain 2 (FnIII-2)(D7) and a Robo receptor Fibronectin type III domain 3 (FnIII-3)(D8), or a portion thereof and selecting candidate agents capable of binding to said polypeptide or portion thereof with a sub-micromolar dissociation constant.

According to some embodiments of the invention the method comprises selecting candidate agents binding to a Robo receptor ectodomain D4 dimerization interface with a micromillar to sub-micromolar dissociation constant.

According to some embodiments of the invention the Robo receptor the binding is characterized by a dissociation constant in the range of 10-250 nM.

According to some embodiments of the invention the method further comprises selecting candidate agents capable of inhibiting Robo receptor dimerization.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 11B:
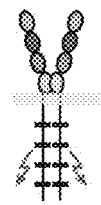

FIG. 1 is a graphic representation of the Robo receptor extracellular immunoglobulin-like (Ig1-Ig5)(D1-D5), fibronectin III (FnIII1-FIII3)(D6-D8) domains, transmembrane domain (TM) and intracellular conserved (cc0-cc3) motifs. Functional domains are indicated for their activity, including D4 dimerization. The hRobo2 receptor D4-D5 fragment used for crystallographic analysis is indicated by an underline;

FIG. 2 is a graph showing the elution profile chromogram of hRobo2 receptor D4-D5 fragment separated by size exclusion chromatography (Superdex 200 26/60, GE Healthcare). The hRobo2 receptor D4-D5 fragment is expressed in a Baculovirus expression system from a modified pFastBac (pK503-9) insect cell expression vector comprising a cDNA encoding a human Robo2 receptor D4-D5 fragment (residues 311-509 of hRobo2 receptor), modified to eliminate N-linked glycosylation. Human Robo2 receptor D4-D5 fragment was secreted into the growth medium and recovered with a metal-chelate (His Trap, GE Healthcare), and then purified on a Superdex 200 26/60 size exclusion (GE Healthcare) column. Inset is a photo showing the migration of the purified human Robo2 D4-D5 fragment size exclusion peak on Coomassie-stained SDS-PAGE;

FIG. 3 is a photograph showing crystals of purified human Robo2 D4-D5 fragment grown by the hanging drop method in 1.1M NaCl and 13% PEG 6000. Single crystal dimensions are approximately 0.05×0.05×0.05 mm;

FIG. 4 is a diffraction image of the human Robo2 D4-D5 fragment crystal, diffracted to a maximum resolution of 2.25 angstrom (A), collected at 100K;

FIG. 5 is a refined 2Fo-Fc electron density map of human Robo2 D4-D5 fragment crystal contoured to 2.6σ and focusing on the D4 dimerization interface, following electron density modification procedures and cycles of model refinement and re-building;

FIG. 6 shows the crystal structure of human Robo2 D4-D5 fragment (PDB code 5NOI), with a crystallographically-related dimer presented on the left, with one protomer displayed as a cartoon and the second with surface representation. On the right, an open-book representation of the D4 dimerization interface (orange and blue) highlights its hydrophobic core residues and peripheral interaction;

FIG. 7 shows a structure-based sequence alignment of human Robo2 receptor D4-D5 fragment sequence (residues 308-510 of SEQ ID NO: 2) to the human Robo1 (residues 345-547 of SEQ ID NO: 16) and Robo3 (residues 345-547 of SEQ ID NO: 17) receptor sequence, as well as to the sequence of Robo1 of Drosophila (residues 339-535 of SEQ ID NO: 13), Sax3 of C. elegans (residues 311-517 of SEQ ID NO: 14), and a Robo-like Cnidarian (jellyfish) protein (residues 325-523 of SEQ ID NO: 15). Orange and blue markers correspond to the D4 dimerization interface residues, as depicted in FIG. 6. Putative Robo ectodomain target sequences for inhibition of D4 dimerization are marked in yellow;

FIGS. 8A-8C are graphs of analytical ultracentrifugation (AUC) sedimentation equilibrium data showing single- and two-species fits for 20 μM wild type (WT, FIG. 8A) and mutant (F357R-FIG. 8B and L394R—FIG. 8C) hRobo2 receptor D4-D5 fragments obtained at a speed of 20000 rpm after 20 hours. Data fitting was performed with Sedphat yielding clear results with small random residuals, indicating a monomer-dimer equilibrium for the WT protein (FIG. 8A) and strict monomers for the two mutants (FIGS. 8B and 8C).

Figure 11C:
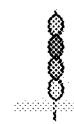
Figure 11D:
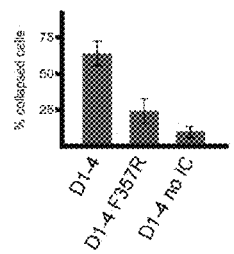
Figure 13:
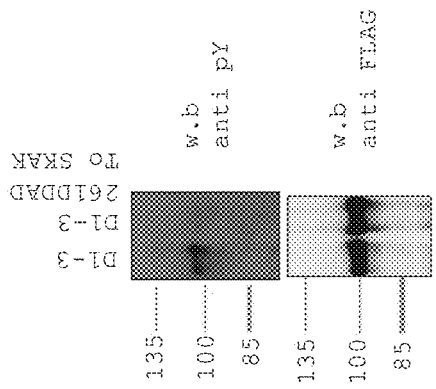
Figure 12A:
Figure 12C:
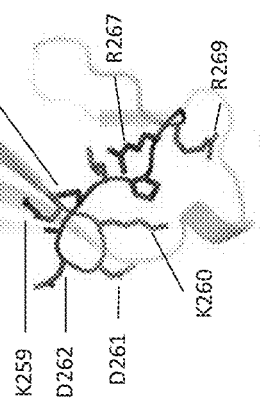
Figure 12B:
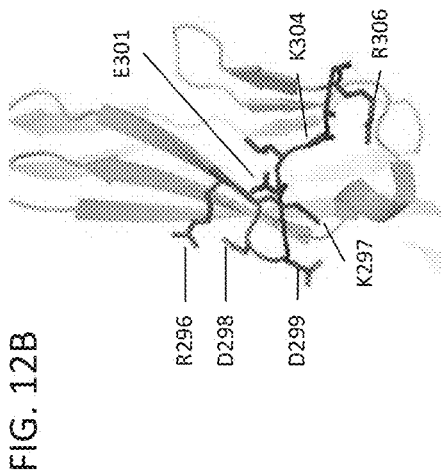
Figure 14:
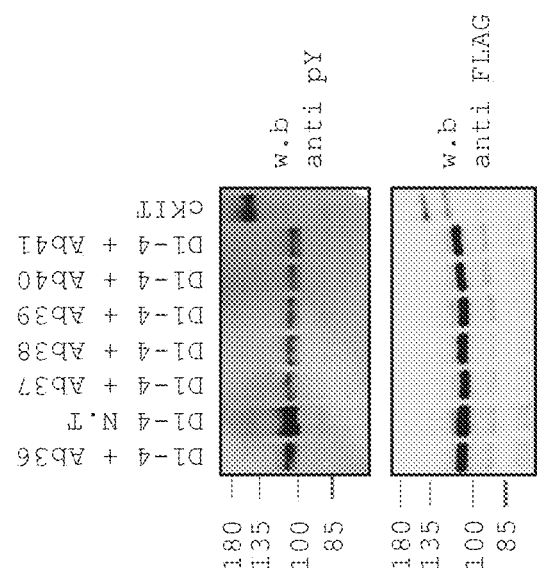
Figure 15B:
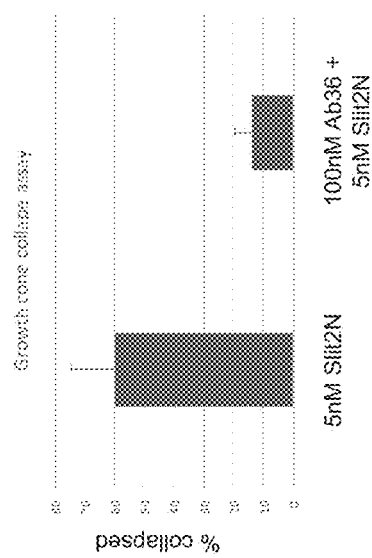
Figure 15A:
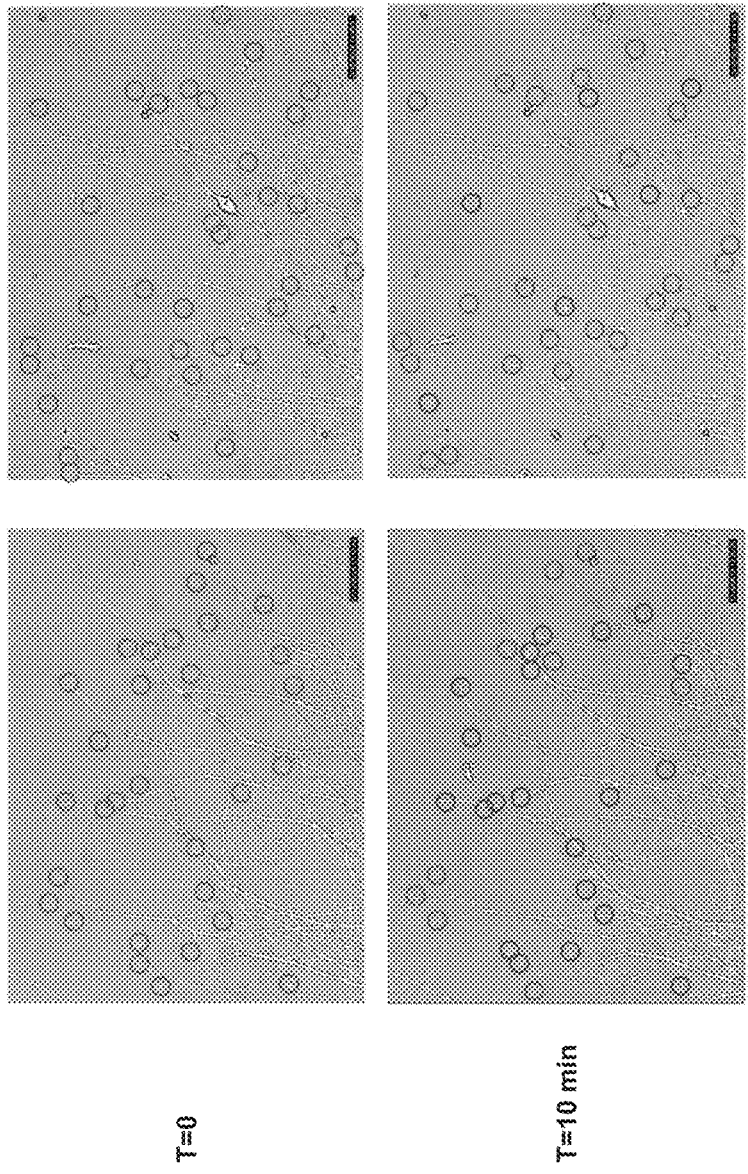

FIG. 9 is a table of the calculated molecular mass, specific volume and dimerization constant $K_D$ for Wild Type hRobo2 receptor D4-D5 fragment. Molecular mass of the WT protein was determined experimentally by mass spectroscopy, revealing a small glycosylation modification. The partial specific volume values were calculated for glycoproteins accordingly. A dimerization constant of 16.9 μM was calculated for the WT hRobo2 receptor D4-D5 fragment;

FIGS. 10A-10F are PAGE data and graphic illustrations of hRobo receptor ectodomain D4-D4 dimerization from a Robo:cKIT chimera phosphorylation assay. Dimerization of the hRobo extracellular domains was measured with a Robo:cKIT chimera trans-phosphorylation assay. The transmembrane and intracellular domains of the Robo receptors were replaced with the kinase domain of the receptor Tyrosine Kinase (RTK) cKIT. cKIT trans-phosphorylates a neighboring cKIT kinase domain, but not itself or a more distant neighbor. For each experiment, cartoons are used to illustrate the constructs that were used and a graph is presented to summarize the relative phosphorylation intensity. Data are means±SEM from three independent experiments. FIG. 10A shows the cKIT trans-phosphorylation assay control. Non-stimulated cKIT is monomeric and is only slightly tyrosine-phosphorylated. Phosphorylation of full-length cKIT is stimulated by stem cell factor (SCF), which is the cKIT ligand that mediates cKIT homo-dimerization (right hand illustration). Truncation of D4, or the substitution of F357, a D4-D4 interface residue (see alignment in FIG. 7), into an arginine (F357R, see FIG. 8B), compromises hRobo2 dimerization in constructs comprising hRobo receptor ectodomains D1-D8 (FIG. 10B), and D1-D4 (FIGS. 10C and 10D). These results are consistent with the analytical ultracentrifuge (AUC) results presented in FIGS. 8A-8C and FIG. 9. Similar D4-mediated dimerization was also observed also for a hRobo1 receptor ectodomain-RTK-cKIT chimera (FIG. 10E) and a hRobo3 receptor ectodomain-RTK-cKIT chimera (FIG. 10F);

FIGS. 11A-11D are fluorescent photomicrographs of COS-7 cells, showing the effect of hRobo2 receptor activation by dimerization on COS-7 cell morphology (COS-7 collapse assay). In this assay, COS-7 cells were transfected with GFP-labeled hRobo2 (green) truncation constructs (see cartoons at right) comprising intact D1-D4 ectodomains and intracellular (IC) segment [hRobo2 (D1-4), FIG. 11A], mutant D1-D4 ectodomains and intact intracellular (IC) segment [hRobo2 (D1-4 F357R), FIG. 11B] and intact D1-D4 ectodomains with no intracellular (IC) segment [hRobo2 (D1-4 no IC), FIG. 11C], fixed and stained with phalloidin (cytoskeleton stain, red) and DAPI (nuclear stain, blue). While un-transfected cells are spread-out, COS-7 cells expressing hRobo2 D1-4 show a dramatic decrease in surface area (FIG. 11A). A milder collapse phenotype is observed with cells transfected with the F357R mutant, due to reduced or abolished D4 mediated dimerization (FIG. 11B). The hRobo2 D1-4 construct lacking the intracellular (IC) segment had very little or no effect on COS-7 cell morphology (FIG. 11C). FIG. 11D is a graph summarizing the percentage of collapsed cells transfected with each of the different constructs. Data are means±SEM from three independent experiments, each including at least 30 cells. Note a clear effect of hRobo2 on the morphology of COS-7 cells, with the strongest effect on cell morphology exerted by the dimerizing hRobo2 D1-4 construct (FIG. 11A);

FIGS. 12A-12C are graphic representations of the molecular structure of human Robo ectodomain fragments, constructed from X-ray crystallography data. FIG. 12A is a graphic representation of the crystal structure of hRobo2 D2-3. FIGS. 12B and 12C are graphic representations of different views of the crystal structure of D3, showing the potential for salt bridges between oppositely charged residues in the CD loops, when accurately apposed;

FIG. 13 shows PAGE data of hRobo receptor ectodomain D3-D3 dimerization from a Robo:cKIT chimera phosphorylation assay (see FIGS. 10A-10F for assay details), comparing cKIT kinase phosphorylation of chimeras with wild type Robo2 ectodomain D1-3 (D1-3) with phosphorylation of D1-3 chimeras with mutated CD loop residues D1-3 261DDAD to SKAK). Alteration of the charge in the CD loop of D3 compromises hRobo2 D1-3 dimerization (loss of anti-pY antigenicity);

FIG. 14 shows PAGE data illustrating inhibition of hRobo2 D1-4 dimerization using the Robo:cKIT chimera trans-phosphorylation assay (see FIGS. 10A-10F for assay details). Addition of 1:200 v/v of six anti-hRobo2 D4-D4 dimerization interface Fab antibodies (Ab36 . . . Ab41) to the growth culture media for overnight incubation reduces hRobo2 D1-4 chimera dimerization relative to untreated controls (NT), as evaluated by the tyrosine phosphorylation;

FIGS. 15A and 15B are photomicrographs and graphic representation showing inhibition of Slit2N-mediated DRG growth cone collapse by anti-hRobo2 D4-D4 dimerization interface antibodies. FIG. 15A: Panels show images from real-time videos of mouse dorsal root ganglion explant culture with (#AbD332836.1+SlitN2) and without (+SlitN2) pretreatment with anti-hRobo2 D4-D4 dimerization site antibody, at 0 time (T=0) and 10 minutes (T=10 min) after addition of SlitN2. Green circles indicate growth cones, red circles indicate collapsed growth cones. FIG. 15B is a histogram showing quantitative representation of the effect of antibody's disruption of dimerization on growth cone collapse.

DESCRIPTION OF SPECIFIC EMBODIMENTS OF THE INVENTION

The present invention, in some embodiments thereof, relates to inhibitory compositions binding to the ectodomain of a Roundabout (Robo) receptor and to the use of same for downregulating Robo-mediated signaling. In particular, the present invention provides moieties that bind to and prevent dimerization of an Ig-like Robo receptor ectodomain, thereby inhibiting Robo receptor activity.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Inhibition of Robo receptor activation by disruption of Slit binding to the Robo receptor ectodomain has been suggested, but is kinetically problematic. The present inventors have identified the extracellular Ig-like domain 4 (D4) as a Robo receptor dimerization domain and uncovered that Robo receptor ectodomain D4-mediated dimerization is critical for Robo receptor's activity.

Through laborious experimentation the inventors have determined the crystal structure of the tandem human Robo2 receptor ectodomains Ig4-5 domains (D4-D5) of human Robo2 (residues 308-510 of human Robo2 receptor polypeptide) and found that a hydrophobic surface on D4 mediates homotypic close contacts with a reciprocal D4. Analytical ultracentrifugation (AUC) measurements of: 1) intact human Robo2 receptor D4-D5, and 2) human Robo2 receptor D4-D5 mutated at the dimerization interface, shows that dimerization through the D4 interface is specific and has a dimerization dissociation constant of 16.9 µM in solution. Dimerization measurements of chimera proteins consisting of different constructs of the ectodomain of Robo2, and the transmembrane and intracellular portions of the receptor tyrosine kinase (RTK) cKIT, in mammalian cultured cells further corroborated hRobo2 dimerization through D4. Using the same chimera cKit assay it was uncovered that D4 mediates dimerization in Robo1 and in Robo3. Antibody fragments (Fab) exclusively binding the native hRobo2D4 dimerization surface inhibited hRobo2 D1-4 dimerization in the chimera cKit assay, and, more importantly, effectively blocked Robo2-mediated cellular responses to SlitN2 activation in cultured Dorsal Root Ganglion explants.

In further studies the present inventors have revealed a secondary Robo receptor dimerization site in the extracellular Ig-like domain 3 (D3), indicating that Robo receptor ectodomain D3-mediated dimerization can also be important for Robo receptor's activity.

The inventors have determined the crystal structure of the tandem human Robo2 receptor ectodomains Ig2-3 domains (D2-D3) of human Robo2 (residues 130-312 of human Robo2 receptor polypeptide). Using the same chimera cKit assay described for D1-4 (see FIG. 10A-10C), it was uncovered that mutating residues within the D3 CD loop interferes with D1-D3 dimerization.

Thus, according to some embodiments of an aspect of the present invention there is provided an agent capable of specifically binding to a Robo receptor ectodomain polypeptide selected from the group consisting of a Robo receptor Immunoglobulin-like domain 3 (D3), a Robo receptor Immunoglobulin-like domain 4 (D4), a Robo receptor Immunoglobulin-like domain 5 (D5), a Robo receptor Fibronectin type III domain 1 (FnIII-1)(D6), a Robo receptor Fibronectin type III domain 2 (FnIII-2)(D7), a Robo receptor Fibronectin type III domain 3 (FnIII-3)(D8), a Robo receptor D3-D4 hinge region, a Robo receptor D4-D5 hinge region, a Robo receptor D5-D6 hinge region, a Robo receptor D6-D7 hinge region and Robo receptor D7-D8 hinge region and a Robo receptor juxtamembrane linker connecting the ectodomaine and the cytosolic portion of Robo, a portion thereof, and inhibiting Robo receptor dimerization.

In other embodiments, the agent comprises a moiety capable of specifically binding to a Robo receptor ectodomain polypeptide selected from the group consisting of Robo receptor Immunoglobulin-like domain 3 (D3), a Robo receptor Immunoglobulin-like domain 4 (D4), a Robo receptor Immunoglobulin-like domain 5 (D5), a Robo receptor Fibronectin type III domain 1 (FnIII-1)(D6), a Robo receptor Fibronectin type III domain 2 (FnIII-2)(D7) and a Robo receptor Fibronectin type III domain 3 (FnIII-3)(D8), or a portion thereof, and inhibiting Robo receptor dimerization.

As used herein, the term "Robo" refers to the Roundabout family of cell surface receptors for the secreted ligand Slit, Robo1, Robo2, Robo3 and Robo4. Typically, Robo contains five Ig motifs (D1-D5) and three fibronectin type III (FNIII) repeats (FnIII 1-FnIII-3 or D6-D8) in its extracellular domain (see FIG. 1). While both immunoglobulin (Ig) domains 1 and 2 interact with Slit, the first Ig1 domain of Robo (D1) is the primary binding site for Slit. The intracellular domain of Robo has four cytoplasmic conserved (CC) sequences: CC0, CC1, CC2, and CC3. CC0 and CC1 contain tyrosine, while CC2 and CC3 are proline-rich stretches. The cell-repulsion activity of Slit-Robo signaling inhibits actin polymerization or induces F-actin depolymerization.

As used herein, the term "Robo receptor" refers to a Roundabout1, Roundabout2, Roundabout3 receptor of any origin from eukaryotic (including, but not limited to molluscs, flatworms, nematodes, echinoderms, cnidarians, brachiopods, arthropods, reptiles, amphibians, birds, fish, placentals and mammals) organisms. In some embodiments, Robo receptor is a human Robo1, Robo2 or Robo3 receptor, or isoform, homologue or orthologue thereof. Human Robo receptors suitable for use with the instant invention include, but are not limited to human Robo receptors having amino acid sequences (Uniprot accession numbers) Q9Y6N7-1,2, 3,4,5,6 (hRobo1), Q9HCK4-1,2,3 (hRobo2), Q96MS0-1,2 (hRobo3). In some embodiments, the human Robo polypeptide is at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or at least 100% identical to the amino acid sequence of the respective native human Robo polypeptide.

Typically, but not exclusively, as used herein, Robo2 or Robo2 receptor refers to any human Robo2. The Robo2 gene is conserved in chimpanzee, Rhesus monkey, dog, cow, mouse, rat, chicken, zebrafish, fruit fly, mosquito, and *C. elegans*. In particular embodiments, "hRobo2" refers to a human Robo2 receptor polypeptide *Homo sapiens* roundabout homolog 2 isoform Robo2a; SEQ ID NO: 1, as described by, e.g., Accession Number NP_001122401.1 and encoded by Accession Number NM_001128929.2; or *Homo sapiens* roundabout homolog 2 isoform Robo2b (SEQ ID NO: 2), as described by, e.g., GenBank Accession number NP_002933.1 or Uniprot Accession Q9HCK4 and encoded by Accession Number NM_002942.4, together with any naturally occurring allelic, splice variants, and processed forms thereof. Specific residues of Robo2 can be referred to as, for example, "Robo2(30)", and specific amino acid sequences can be referred to as, for example, Robo2(311-312) or Robo2(349-377). In particular embodiments, Robo1 refers to a human Robo1 receptor polypeptide *Homo sapiens* roundabout homolog 1 as described by, e.g. Uniprot Accession Number Q9Y6N7, having the amino acid sequence SEQ ID NO: 16. In particular embodiments, Robo3 refers to a human Robo3 receptor polypeptide *Homo sapiens* roundabout homolog 3 as described by, e.g. Uniprot Accession Number Q96MS0, having the amino acid sequence SEQ ID NO: 17. Other suitable Robo proteins include, but are not limited to *Drosophila* Robo1 receptor polypeptide roundabout homolog 1 as described by, e.g. GeneBank Accession Number AAC38849.1, having the amino acid sequence SEQ ID NO: 13, *C. elegans* SAX-3 receptor polypeptide roundabout homolog as described by, e.g. GeneBank Accession Number NP_001024990.1, having the amino acid sequence SEQ ID NO: 14 and Cnidaria Robo-like receptor polypeptide roundabout homolog as described by, e.g. GeneBank Accession Number KXJ15078.1, having the amino acid sequence SEQ ID NO: 15.

Specific domains of Robo2 can be referred to by such nomenclature as well. The N-terminal or "extracellular domain of Robo2", comprising the five immunoglobulin motifs and three fibronectin type III (FNIII) repeats can be referred to as Robo2(22-859), for example. The immunoglobulin (Ig) motifs D1 and D2 that interact with Slit2, or the "Ig SLIT binding domain" can be referred to as Robo2(D1, 28-129) and Robo2(D2, 130-223). The Immunoglobulin-like motifs D3-D5 and fibronectin III motifs D6-D8 of Robo2 can be referred to as Robo2 D3(224-312), Robo2 D4 (313-410), Robo2 D4-D5 linker (411-415), Robo2 D5(416-508), Robo2 D5-D6 linker (509-519), Robo2 D6 (520-616), Robo2 D6-D7 linker (617-626), Robo2 D7(627-733) and Robo2 D8 (734-838), Robo2 extracellular-juxtamembrane segment (839-859), ectodomains, respectively of human Robo2. Similarly, the "intracellular domain" comprising the "Nck intracellular binding domain," which comprises the four intracellular proline rich motifs, described herein, can be referred to as Robo2(881-1378) of human Robo2.

According to the present invention, the agent specifically binding to a Robo receptor domain or portion thereof is capable of inhibiting Robo receptor dimerization. The present inventors have deciphered the crystal structure of human Robo receptor ectodomains D2-D3 and D4-D5, identifying epitopes (e.g., conformational epitopes, sequences) comprising regions of the Robo ectodomain which the agents and moieties of the present invention may target, in order to prevent the dimerization of the Robo receptor ectodomain. In some embodiments, the agents and moieties of the invention bind the Robo receptor ectodomain polypeptide in the region of Robo receptor ectodomain D3 and/or D4 dimerization interface. In some embodiments, the Robo receptor ectodomain D4 dimerization interface comprises an amino acid sequence spanning residues 339-402 of hRobo2 (SEQ ID NO: 31). In other embodiments, the Robo receptor ectodomain D4 dimerization interface comprises an amino acid sequence spanning residues 376-439 of hRobo1 (SEQ ID NO: 32), or an amino acid sequence spanning residues 372-435 of hRobo3 (SEQ ID NO: 33). In specific embodiments, the Robo receptor ectodomain D4 dimerization interface comprises an amino acid sequence spanning residues 339-402 of hRobo2 (SEQ ID NO: 31).

In other embodiments, the Robo receptor ectodomain D4 dimerization interface comprises an amino acid sequence corresponding to residues 339-402 of hRobo2, including regions of residues conserved between human Robo1, Robo2 and Robo3 receptors (e.g. hRobo2 339-344, hRobo2 350-353 and the like), the conserved regions separated by non-conserved residues, as shown in the alignment of FIG. 7. In one embodiment, such a Robo receptor ectodomain D4 dimerization interface including non-conserved residues comprises the amino acid sequence SEQ ID NO: 34. In other embodiments, the amino acid sequence of the Robo receptor D4 ectodomain dimerization interface comprises conserved regions corresponding to Robo2 339-361 (344×1346-347×2×3350-353×4355-357×5×6360-361), . . . 369-371 (369×7×8), . . . and 391-402 (391-392×9×10×11396-401×12) wherein x1 is selected from the group consisting of Valine and Isoleucine; x2 is selected from the group consisting of Glutamine and Arginine; x3 is selected from the group consisting of Lysine and Arginine; x4 is selected from the group consisting of Asparagine and Valine; x5 is selected from the group consisting of Proline and Serine; x6 is selected from the group consisting of Asparagine, Tyrosine and Serine; x7 is selected from the group consisting of Proline and Glutamine; x8 is selected from the group consisting of Threonine and Arginine; x9 is selected from the group consisting of Alanine and Threonine; x10 is selected from the group consisting of Leucine and Valine; x11 is selected from the group consisting of Threonine, Asparagine and Serine; x12 is selected from the group consisting of Alanine and Threonine, grouped into three regions (corresponding to hRobo2 339-361, 369-371 and 391-402) separated by non-dimerization interface sequences consistent with the overall three-dimensional configuration of the Robo2 receptor D4 ectodomain. In some embodiments, such a Robo receptor ectodomain D4 dimerization interface separated by non-dimerization sequences comprises the amino acid sequence SEQ ID NO: 27. In some embodiments, the Robo receptor ectodomain D3 dimerization interface comprises the amino acid sequence KKDDADLPRGRY (SEQ ID NO: 18) [hRobo2 (UniProtKB-Q9HCK4) D3 Dimerization interface, starting at amino acid residue 259]. In other embodiments, the Robo receptor ectodomain D3 dimerization interface comprises the amino acid sequence RKDDGELPKSRY (SEQ ID NO: 19) [hRobo1 (UniProtKB-Q9Y6N7) D3 Dimerization interface, starting at amino acid residue 296]. In yet another embodiment, the Robo receptor ectodomain D3 dimerization interface comprises the amino acid sequence RKEDGELPTGRY (SEQ ID NO: 20) [hRobo3 (UniProtKB-Q96N7) D3 Dimerization interface, starting at amino acid residue 292]. In specific embodiments, binding of the agent or moiety to the D3-D3 and/or D4-D4 dimerization interface inhibits Robo receptor D4-D4 dimerization. In some embodiments, the agents and moieties of the invention bind the Robo receptor ectodomain polypeptide within the Robo receptor ectodomain D3 and/or D4 dimerization interface. In some embodiments, the agents and moieties of the invention bind the Robo receptor ectodomain polypeptide at the Robo receptor ectodomain D3 and/or D4 dimerization interface.

The present inventors have also identified sequences flanking and within the Robo receptor ectodomain D3 and/or D4 dimerization interface which can be targeted by the agents and moieties of the invention for inhibition of Robo receptor dimerization. Thus, in other embodiments the agent or moiety binds to any one of Robo receptor ectodomain sequences Robo2(336-340, SEQ ID NO: 21), Robo2(369-377, SEQ ID NO: 22), Robo2(382-390, SEQ ID NO: 23) and Robo 2(402-410, SEQ ID NO: 24), or combinations thereof. In specific embodiments, binding of the agent or moiety to Robo2(336-340, SEQ ID NO: 21), Robo2(369-377, SEQ ID NO: 22), Robo 2(382-390, SEQ ID NO: 23), Robo2(402-410, SEQ ID NO: 24) of human Robo2 or the Robo receptor ectodomain D4 dimerization interface of Robo2 inhibits Robo receptor D4-D4 dimerization. In other embodiments, binding of the agent or moiety to Robo2 (259-270, SEQ ID NO: 25), of human Robo2 or the Robo receptor ectodomain D3 dimerization interface of Robo2 inhibits Robo2 receptor D3-D3 dimerization. In still other embodiments, binding of the agent or moiety to epitopes comprised within hRobo2 D3 ectodomain (224-312, SEQ ID NO: 26), of human Robo2 or epitopes comprising the Robo receptor ectodomain D3 dimerization interface of Robo2 inhibits Robo2 receptor D3-D3 dimerization.

The inventors have uncovered that the Slit ligand binding portion of the Robo receptor ectodomain may not be required for Robo receptor activation via D4-D4 dimerization. In some embodiments, the agent of the invention is specific for Robo receptor ectodomains D3-D8. In particular embodiments, the agent of the invention does not bind any of the Slit binding domains, for example, any one or more of Robo receptor immunoglobulin-like ectodomains D1 or D2, D1-D2 or D1-D2 hinge region.

In other embodiments, the agent or moiety of the invention binds to at least one of Robo D3 to Robo D8, Robo2 (259-270, SEQ ID NO: 25), Robo2(336-340, SEQ ID NO: 21), Robo 2(369-377, SEQ ID NO: 22), Robo2(382-390, SEQ ID NO: 23), Robo2(402-410, SEQ ID NO: 24) of human Robo2 or the Robo receptor ectodomain D4 dimerization interface of Robo or a portion thereof, wherein the binding inhibits Robo receptor D3-D3 and/or D4-D4 dimerization and the agent does not bind either of Robo receptor D1 or D2 or D1-D2 hinge region.

As used herein, the term "Robo receptor dimerization" refers to a chemical union between two Robo receptor monomers or portions thereof, forming a dimer. The chemical union of the dimer is the result of a non-covalent union, such as, for example, hydrogen bonding, or it may be the result of a covalent union, such as, for example, a cysteine-cysteine disulfide bond. In some embodiments, Robo receptor dimerization comprises both covalent and non-covalent bonding between the two Robo receptor monomers.

Some Robo receptor polypeptides are occasionally associated in an inactive oligomeric conformation on the cell surface, but which oligomeric conformation is insufficient to allow activation of the Robo receptor (e.g. mouse Robo1, Zakrys et al, 2005). According to some aspects of some embodiments, Robo receptor dimerization is coordinated dimerization, occurring between the D4-D4 dimerization interface of adjacent Robo receptor ectodomains and facilitating activation of the Robo receptor and intracellular signaling.

In some embodiments Robo dimerization is between identical Robo polypeptides, e.g., human Robo2 D3-D3 or D4-D4 or D3-D3/D4-D4 homodimers (homodimerization forming Robo homodimers). In other embodiments, the Robo dimerization can be between dissimilar Robo polypeptides (monomers), e.g. Robo heterodimerization. In specific embodiments, the agent or moiety inhibits homodimerization of the D4 domain of Robo2 receptor, for example, human Robo 2 receptor D4-D4 dimerization. In other specific embodiments, the agent or moiety inhibits homodimerization of the D3 domain of Robo2 receptor, for example, human Robo2 receptor D3-D3 dimerization. In yet other specific embodiments, the agent or moiety inhibits homodimerization of both the D3 and the D4 domain of Robo2 receptor, for example, human Robo2 receptor D3-D3/D4-D4 dimerization.

In some embodiments, binding of the agent of the invention affects the positioning, orientation and/or distance between the two monomers (e.g., the D3-D3, D4-D4 or both D3-D3 and D4-D4 domains of a Robo receptor), thereby inhibiting the activity of the Robo receptor. In some examples, the agent and/or moiety of the invention may allow ligand-induced dimerization of the Robo receptor ectodomains, but affect the positioning of the two ectodomains at the cell surface interface or alter or prevent conformational changes in the Robo receptors, thereby inhibiting the activity of the Robo receptor. In some examples, the agent and/or moiety of the invention may allow ligand-induced dimerization of Robo receptor ectodomains, but affect the positioning of more than two ectodomains at the cell surface interface (e.g. D3-D3 and D4-D4) or alter or prevent conformational changes in the Robo receptors, thereby inhibiting the activity of the Robo receptor.

According to other specific embodiments, inhibition of dimerization of Robo receptors may be by at least a 10%, at least 20%, at least 30%, at least 40%, at least 50%, at least 60%, at least 70%, at least 80%, at least 90%, at least 95% or at least 99% inhibition of dimerization. In other embodiments, inhibition of dimerization of Robo receptors is in the range of 10%-95%, 15%-50%, 20%-60%, 25%-75%, 30%-85%, 35%-75%, 40%-90%, 40%-80%, 40%-75%, 40%-60% inhibition of dimerization. In some embodiments, inhibition of Robo receptor dimerization is expressed as the degree (e.g. amount, percentage, negative fold increase, etc.) of dimerization relative to dimerization of similar or identical Robo receptors under similar or identical conditions not exposed to the agent or moiety of the invention.

The instant inventors have uncovered the association between Robo receptor dimerization and Robo receptor activation. As used herein, the term "Robo activation" or "Robo receptor activation" refers to Robo (e.g. mammalian, such as human, Robo) biological activity in vitro, in situ, and/or in vivo, including activity of downstream pathways mediated by Robo2 signaling, such as, for example, Robo2 interaction with the adaptor protein Nck and/or complex formation with nephrin, SLIT2-Robo2 mediated inhibition of nephrin-mediated actin polymerization, and/or elicitation of a cellular response to Robo2, Robo receptor internalization and/or phosphorylation and dephosphorylation (e.g. of the receptor), recruitment of intracellular protein effectors and/or activation of downstream signaling pathways.

Thus, in some embodiments, binding of the agent and/or moiety of the invention to the Robo ectodomain or portion thereof inhibits intracellular signaling via the Robo receptor intracellular domain. In other embodiments, inhibition of the intracellular signaling via the Robo intracellular domain downregulates activity of Robo-associated (e.g. directly and indirectly dependent on Robo activation) pathways. As used herein, the term "inhibiting intracellular signaling", "inhibiting Robo activation" or "inhibiting Robo receptor activation" refers to significantly blocking, inhibiting, reducing, or interfering with biological activity in vitro, in situ, and/or in vivo, including activity of downstream pathways mediated by Robo2 signaling, such as, for example, Robo2 interaction with the adaptor protein Nck and/or complex formation with nephrin, SLIT2-Robo2 mediated inhibition of nephrin-mediated actin polymerization, and/or elicitation of a cellular response to Robo2, Robo receptor internalization and/or phosphorylation and dephosphorylation (e.g. of the receptor), recruitment of intracellular protein effectors and/or activation of downstream signaling pathways. Intracellular protein effectors in Robo-associated pathways include, but are not limited to the actin binding proteins Ena and Canoe/AF-6, the tyrosine kinase Abelson (Abl), the Ras/Rho GEF Son of Sevenless (SOS), and Rac1/RhoA/CDC42 activating SRGAP proteins.

Assays useful for assessing binding of the agent and/or moiety of the invention to a Robo receptor ectodomain polypeptide, and dimerization of the Robo receptor polypeptide include, but are not limited to sedimentation equilibrium-analytical unitracentrifugation, chromatography, mass spectroscopy, electrophoretic methods, immunodetection assays such as ELISA and western blot analysis and immunohistochemistry. Functional assays for assessment of cellular effects of Robo binding and dimerization include, but are not limited to detecting the expression level of RNA of Robo-associated genes, for example, Northern Blot analysis, RT-PCR analysis, RNA in situ hybridization stain, In situ RT-PCR stain, DNA microarrays/DNA chips, Oligonucleotide microarrays, detecting expression and/or activity of proteins such as enzyme linked immunosorbent assay (ELISA), Western blot, Radio-immunoassay (RIA), Fluorescence activated cell sorting (FACS), Immunohistochemical analysis, in situ activity assay in-vivo and in vitro activity assays. In some embodiments, the biological activity associated with "Robo activation" or "Robo receptor activation" includes a growth cone collapse and axon retraction assay [for example, in cultured Dorsal Root Ganglion (DRG) cells].

According to some embodiments, the agent or moiety binding to the Robo receptor and inhibiting Robo dimerization is selected from the group consisting of an antibody, a peptide, a polypeptide, a peptidomimetic, a DNA, an RNA, an aptamer (DNA/RNA), a peptoid, a zDNA, a peptide nucleic acid (PNA), a locked nucleic acid (LNA), a lectin, an adnectin and a dendrimer.

One agent which can be used to inhibit Robo receptor dimerization and/or activation is an antibody. Another agent which can be used along with some embodiments of the invention to downregulate Robo receptor dimerization and/or activation is an aptamer. As used herein, the term "aptamer" refers to double stranded or single stranded RNA molecule that binds to specific molecular target, such as a protein. Various methods are known in the art which can be used to design protein specific aptamers. The skilled artisan can employ SELEX (Systematic Evolution of Ligands by Exponential Enrichment) for efficient selection as described in Stoltenburg R, Reinemann C, and Strehlitz B (Biomolecular engineering (2007) 24(4):381-403).

Another agent capable of downregulating Robo receptor dimerization and/or activation would be any molecule which binds to and/or cleaves the Robo ectodomain sequences or portions detailed herein. Such molecules can be a small molecule, antagonists, or Robo ectodomain interaction inhibitory peptide.

It will be appreciated that a non-functional analogue of at least a binding portion of a Robo receptor can be also used as an agent which downregulates Robo receptor dimerization and/or activation.

According to specific embodiments the agent capable of binding to a Robo ectodomain or portion thereof is an antibody or antibody fragment capable of specifically binding a Robo receptor ectodomain or portion thereof. Preferably, the antibody or antibody fragment specifically binds at least one epitope of a Robo receptor domain. As used herein, the term "epitope" refers to any antigenic determinant on an antigen to which the paratope of an antibody binds. Epitopic determinants usually consist of chemically active surface groupings of molecules such as amino acids or carbohydrate side chains and usually have specific three dimensional structural characteristics, as well as specific charge characteristics.

Antibodies or antibody fragments (e.g. Fab) specifically binding hRobo2 wild type polypeptides can eliminate hRobo2 D4-D4 dimerization (see, for example, FIGS. 8A-8C and 14). Thus, in some embodiments, the agent capable of binding to a Robo ectodomain or portion thereof is an antibody or antibody fragment which specifically binds a dimerizing Robo receptor ectodomain or portion thereof. Non-limiting example of such anti-Robo receptor antibody or antibody fragments include, but are not limited to antibody AbD32836.1. In some embodiments, the anti-Robo receptor antibody or antibody fragment is an antibody or antibody fragment which binds a dimerizing interface of a Robo receptor ectodomain, for example, at the D3-D3 dimerizing interface or the D4-D4 dimerizing interface. In some embodiments, the anti-Robo receptor antibody or antibody fragment is an antibody or antibody fragment which binds a dimerizing interface of a Robo receptor ectodomain and is specific for an epitope of an "active" dimerizing interface, e.g, an antibody or antibody fragment which exhibits differential binding for a Robo receptor ectodomain dimerizing interface which facilitates dimerization under physiological conditions (e.g. wild-type Robo receptor ectodomain dimerizing interface), and which antibody or antibody fragment does not bind to a Robo receptor ectodomain dimerizing interface which does not dimerize under physiological conditions (e.g. mutated Robo receptor ectodomain dimerizing interface). Non-limiting examples of such an anti-Robo receptor antibody or antibody fragments having differential specificity include, but are not limited to Fab AbD32836.1.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference, and detailed description below).

The term "antibody" as used in this invention includes intact molecules as well as functional fragments thereof (such as Fab, F(ab')2, Fv, scFv, dsFv, or single domain molecules such as VH and VL) that are capable of binding to an epitope of an antigen.

Suitable antibody fragments for practicing some embodiments of the invention include a complementarity-determining region (CDR) of an immunoglobulin light chain (referred to herein as "light chain"), a complementarity-determining region of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single chain Fv (scFv), a disulfide-stabilized Fv (dsFv), an Fab, an Fab', and an F(ab')2.

As used herein, the terms "complementarity-determining region" or CDR" are used interchangeably to refer to the antigen binding regions found within the variable region of the heavy and light chain polypeptides. Generally, antibodies comprise three CDRs in each of the VH (CDR HI or HI; CDR H2 or H2; and CDR H3 or H3) and three in each of the VL (CDR LI or LI; CDR L2 or L2; and CDR L3 or L3).

The identity of the amino acid residues in a particular antibody that make up a variable region or a CDR can be determined using methods well known in the art and include methods such as sequence variability as defined by Kabat et al. (See, e.g., Kabat et al., 1992. Sequences of Proteins of Immunological Interest, 5th ed., Public Health Service, NIH, Washington D.C.), location of the structural loop regions as defined by Chothia et al. (see, Chothia et al. Nature 342: 877-883, 1989), a compromise between Kabat and Chothia using Oxford Molecular's AbM antibody modeling software (now Accelrys®, see. Martin et al., 1989. Proc. Natl Acad Sci USA. 86:9268; and world wide web site www(dot)bioinf-org(dot)uk/abs), available complex crystal structures as defined by the contact definition (see MacCallum et al., J. Mol. Biol. 262:732-745, 1996) and the "conformational definition" (see, e.g., Makabe et al. Journal of Biological Chemistry, 283:1156-1 166, 2008).

As used herein, the "variable regions" and "CDRs" may refer to variable regions and CDRs defined by any approach known in the art, including combinations of approaches.

Functional antibody fragments comprising whole or essentially whole variable regions of both light and heavy chains are defined as follows:

(i) Fv, defined as a genetically engineered antibody fragment consisting of the variable region of the light chain (VL) and the variable region of the heavy chain (VH) expressed as two chains;

(ii) single chain Fv ("scFv"), a genetically engineered single chain molecule including the variable region of the light chain and the variable region of the heavy chain, linked by a suitable polypeptide linker as a genetically fused single chain molecule.

(iii) disulfide-stabilized Fv ("dsFv"), a genetically engineered antibody including the variable region of the light chain and the variable region of the heavy chain, linked by a genetically engineered disulfide bond.

(iv) Fab, a fragment of an antibody molecule containing a monovalent antigen-binding portion of an antibody molecule which can be obtained by treating whole antibody with the enzyme papain to yield the intact light chain and the Fd fragment of the heavy chain which consists of the variable and CH1 domains thereof;

(v) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule);

(vi) F(ab')2, a fragment of an antibody molecule containing a monovalent antigen-binding portion of an antibody molecule which can be obtained by treating whole antibody with the enzyme pepsin (i.e., a dimer of Fab' fragments held together by two disulfide bonds); and (vii) Single domain antibodies or nanobodies are composed of a single VH or VL domains which exhibit sufficient affinity to the antigen.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

According to a specific embodiment, the Robo binding moiety of the present invention is a Fab antibody fragment. An exemplary Fab antibody fragment which may be used in accordance with the present teachings is AbD32836.1 and comprises complementarity determining regions (CDRs) SEQ ID NOs: 5-10. Accordingly, CDRs 1-3 (SEQ ID NOs: 8, 9 and 10, respectively) are located on the light chain of the antibody and CDRs 1-3 (SEQ ID NOs: 5, 6 and 7, respectively) are located on the heavy chain of the antibody. Fab antibody fragment AbD32836.1 further comprises the Fd chain (including tags) as set forth in SEQ ID NO: 3. The amino acid sequence of the light chain of Fab antibody or antibody fragment AbD32836.1 is as set forth in SEQ ID NO: 4. CL and CH1 sequences of the Fab antibody or antibody fragment AbD32836.1 are as set forth in SEQ ID NO: 11 and 12, respectively. Positions of the CDRs of antibody or antibody fragment AbD32836.1 are as defined by Kabat et al.

According to another embodiment, the antibody of the present invention is a single chain antibody. A single chain antibody which may be used in accordance with the present teachings comprises complementarity determining regions (CDRs) selected from SEQ ID NOs: 8-10 (Light Chain) and 5-7 (Heavy Chain).

According to another embodiment, an antibody of the present invention comprises the amino acid sequences as set forth in SEQ ID NOs: 3 and 4.

According to another embodiment, an isolated antibody or Fab fragment of the present invention comprises the amino acid sequence as set forth in SEQ ID NOs: 3 and 4.

Antibody fragments according to some embodiments of the invention can be prepared by proteolytic hydrolysis of the antibody or by expression in *E. coli* or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This antibody fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain antibody fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10,: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

In some embodiments, the agent or moiety capable of binding Robo receptor and inhibiting dimerization thereof is a peptide.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated amide bonds (—N(CH3)-CO—), ester bonds (—C(=O)—O—), ketomethylene bonds (—CO—CH2-), sulfinylmethylene bonds (—S(=O)—CH2-), α-aza bonds (—NH—N(R)—CO—), wherein R is any alkyl (e.g., methyl), amine bonds (—CH2-NH—), sulfide bonds (—CH2-S—), ethylene bonds (—CH2-CH2-), hydroxyethylene bonds (—CH(OH)—CH2-), thioamide bonds (—CS—NH—), olefinic double bonds (—CH=CH—), fluorinated olefinic double bonds (—CF=CH—), retro amide bonds (—NH—CO—), peptide derivatives (—N(R)—CH2-CO—), wherein R is the "normal" side chain, naturally present on the carbon atom.

These modifications can occur at any of the bonds along the peptide chain and even at several (2-3) bonds at the same time.

Natural aromatic amino acids, Trp, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halogenated derivatives of Phe or O-methyl-Tyr.

The peptides of some embodiments of the invention may also include one or more modified amino acids or one or more non-amino acid monomers (e.g. fatty acids, complex carbohydrates etc.).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodemosine, nor-valine, nor-leucine and ornithine. Furthermore, the term "amino acid" includes both D- and L-amino acids.

Tables 1 and 2 below list naturally occurring amino acids (Table 1), and non-conventional or modified amino acids (e.g., synthetic, Table 2) which can be used with some embodiments of the invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| Ornithine | Orn | hydroxyproline | Hyp |
| α-aminobutyric acid | Abu | aminonorbornyl-carboxylate | Norb |

TABLE 2-continued

| Non-conventional amino acid | Code | Non-conventional amino acid | Code |
| --- | --- | --- | --- |
| D-alanine | Dala | aminocyclopropane-carboxylate | Cpro |
| D-arginine | Darg | N-(3-guanidinopropyl)glycine | Narg |
| D-asparagine | Dasn | N-(carbamylmethyl)glycine | Nasn |
| D-aspartic acid | Dasp | N-(carboxymethyl)glycine | Nasp |
| D-cysteine | Dcys | N-(thiomethyl)glycine | Ncys |
| D-glutamine | Dgln | N-(2-carbamylethyl)glycine | Ngln |
| D-glutamic acid | Dglu | N-(2-carboxyethyl)glycine | Nglu |
| D-histidine | Dhis | N-(imidazolylethyl)glycine | Nhis |
| D-isoleucine | Dile | N-(1-methylpropyl)glycine | Nile |
| D-leucine | Dleu | N-(2-methylpropyl)glycine | Nleu |
| D-lysine | Dlys | N-(4-aminobutyl)glycine | Nlys |
| D-methionine | Dmet | N-(2-methylthioethyl)glycine | Nmet |
| D-ornithine | Dorn | N-(3-aminopropyl)glycine | Norn |
| D-phenylalanine | Dphe | N-benzylglycine | Nphe |
| D-proline | Dpro | N-(hydroxymethyl)glycine | Nser |
| D-serine | Dser | N-(1-hydroxyethyl)glycine | Nthr |
| D-threonine | Dthr | N-(3-indolylethyl)glycine | Nhtrp |
| D-tryptophan | Dtrp | N-(p-hydroxyphenyl)glycine | Ntyr |
| D-tyrosine | Dtyr | N-(1-methylethyl)glycine | Nval |
| D-valine | Dval | N-methylglycine | Nmgly |
| D-N-methylalanine | Dnmala | L-N-methylalanine | Nmala |
| D-N-methylarginine | Dnmarg | L-N-methylarginine | Nmarg |
| D-N-methylasparagine | Dnmasn | L-N-methylasparagine | Nmasn |
| D-N-methylasparatate | Dnmasp | L-N-methylaspartic acid | Nmasp |
| D-N-methylcysteine | Dnmcys | L-N-methylcysteine | Nmcys |
| D-N-methylglutamine | Dnmgln | L-N-methylglutamine | Nmgln |
| D-N-methylglutamate | Dnmglu | L-N-methylglutamic acid | Nmglu |
| D-N-methylhistidine | Dnmhis | L-N-methylhistidine | Nmhis |
| D-N-methylisoleucine | Dnmile | L-N-methylisolleucine | Nmile |
| D-N-methylleucine | Dnmleu | L-N-methylleucine | Nmleu |
| D-N-methyllysine | Dnmlys | L-N-methyllysine | Nmlys |
| D-N-methylmethionine | Dnmmet | L-N-methylmethionine | Nmmet |
| D-N-methylornithine | Dnmorn | L-N-methylornithine | Nmorn |
| D-N-methylphenylalanine | Dnmphe | L-N-methylphenylalanine | Nmphe |
| D-N-methylproline | Dnmpro | L-N-methylproline | Nmpro |
| D-N-methylserine | Dnmser | L-N-methylserine | Nmser |
| D-N-methylthreonine | Dnmthr | L-N-methylthreonine | Nmthr |
| D-N-methyltryptophan | Dnmtrp | L-N-methyltryptophan | Nmtrp |
| D-N-methyltyrosine | Dnmtyr | L-N-methyltyrosine | Nmtyr |
| D-N-methylvaline | Dnmval | L-N-methylvaline | Nmval |
| L-norleucine | Nle | L-N-methylnorleucine | Nmnle |
| L-norvaline | Nva | L-N-methylnorvaline | Nmnva |
| L-ethylglycine | Etg | L-N-methyl-ethylglycine | Nmetg |
| L-t-butylglycine | Tbug | L-N-methyl-t-butylglycine | Nmtbug |
| L-homophenylalanine | Hphe | L-N-methyl-homophenylalanine | Nmhphe |
| α-naphthylalanine | Anap | N-methyl-α-naphthylalanine | Nmanap |
| Penicillamine | Pen | N-methylpenicillamine | Nmpen |
| γ-aminobutyric acid | Gabu | N-methyl-γ-aminobutyrate | Nmgabu |
| cyclohexylalanine | Chexa | N-methyl-cyclohexylalanine | Nmchexa |
| cyclopentylalanine | Cpen | N-methyl-cyclopentylalanine | Nmcpen |
| α-amino-α-methylbutyrate | Aabu | N-methyl-α-amino-α-methylbutyrate | Nmaabu |
| α-aminoisobutyric acid | Aib | N-methyl-α-aminoisobutyrate | Nmaib |
| D-α-methylarginine | Dmarg | L-α-methylarginine | Marg |
| D-α-methylasparagine | Dmasn | L-α-methylasparagine | Masn |
| D-α-methylaspartate | Dmasp | L-α-methylaspartate | Masp |
| D-α-methylcysteine | Dmcys | L-α-methylcysteine | Mcys |
| D-α-methylglutamine | Dmgln | L-α-methylglutamine | Mgln |
| D-α-methyl glutamic acid | Dmglu | L-α-methylglutamate | Mglu |
| D-α-methylhistidine | Dmhis | L-α-methylhistidine | Mhis |
| D-α-methylisoleucine | Dmile | L-α-methylisoleucine | Mile |
| D-α-methylleucine | Dmleu | L-α-methylleucine | Mleu |
| D-α-methyllysine | Dmlys | L-α-methyllysine | Mlys |
| D-α-methylmethionine | Dmmet | L-α-methylmethionine | Mmet |
| D-α-methylornithine | Dmorn | L-α-methylornithine | Morn |
| D-α-methylphenylalanine | Dmphe | L-α-methylphenylalanine | Mphe |
| D-α-methylproline | Dmpro | L-α-methylproline | Mpro |
| D-α-methylserine | Dmser | L-α-methylserine | Mser |
| D-α-methylthreonine | Dmthr | L-α-methylthreonine | Mthr |
| D-α-methyltryptophan | Dmtrp | L-α-methyltryptophan | Mtrp |
| D-α-methyltyrosine | Dmtyr | L-α-methyltyrosine | Mtyr |
| D-α-methylvaline | Dmval | L-α-methylvaline | Mval |
| N-cyclobutylglycine | Ncbut | L-α-methylnorvaline | Mnva |
| N-cycloheptylglycine | Nchep | L-α-methylethylglycine | Metg |
| N-cyclohexylglycine | Nchex | L-α-methyl-t-butylglycine | Mtbug |
| N-cyclodecylglycine | Ncdec | L-α-methyl-homophenylalanine | Mhphe |
| N-cyclododecylglycine | Ncdod | α-methyl-α-naphthylalanine | Manap |

TABLE 2-continued

| Non-conventional amino acid | Code | Non-conventional amino acid | Code |
|---|---|---|---|
| N-cyclooctylglycine | Ncoct | α-methylpenicillamine | Mpen |
| N-cyclopropylglycine | Ncpro | α-methyl-γ-aminobutyrate | Mgabu |
| N-cycloundecylglycine | Ncund | α-methyl-cyclohexylalanine | Mchexa |
| N-(2-aminoethyl)glycine | Naeg | α-methyl-cyclopentylalanine | Mcpen |
| N-(2,2-diphenylethyl)glycine | Nbhm | N-(N-(2,2-diphenylethyl) carbamylmethyl-glycine | Nnbhm |
| N-(3,3-diphenylpropyl)glycine | Nbhe | N-(N-(3,3-diphenylpropyl) carbamylmethyl-glycine | Nnbhe |
| 1-carboxy-1-(2,2-diphenyl ethylamino)cyclopropane | Nmbc | 1,2,3,4-tetrahydroisoquinoline-3-carboxylic acid | Tic |
| phosphoserine | pSer | phosphothreonine | pThr |
| phosphotyrosine | pTyr | O-methyl-tyrosine | |
| 2-aminoadipic acid | | hydroxylysine | |

The peptides of some embodiments of the invention are preferably utilized in a linear form, although it will be appreciated that in cases where cyclicization does not severely interfere with peptide characteristics, cyclic forms of the peptide can also be utilized.

Since the present peptides are preferably utilized in therapeutics or diagnostics which require the peptides to be in soluble form, the peptides of some embodiments of the invention preferably include one or more non-natural or natural polar amino acids, including but not limited to serine and threonine which are capable of increasing peptide solubility due to their hydroxyl-containing side chain.

The peptides of some embodiments of the invention may be synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of peptide synthesis is disclosed in U.S. Pat. No. 6,472,505.

A preferred method of preparing the peptide compounds of some embodiments of the invention involves solid phase peptide synthesis.

Large scale peptide synthesis is described by Andersson Biopolymers 2000; 55(3):227-50.

In some embodiments, the present invention provides a polynucleotide comprising a nucleic acid sequence encoding the agent or moiety binding the Robo receptor ectodomain polypeptide. Such polynucleotides can be used to clone and express the agents and/or moieties of the invention in transformed cells. Methods for cloning, transforming cells and expressing recombinant peptides or polypeptides well known in the art can be used with this invention.

In particular embodiments, it is desirable for the binding of the agent or moiety to the Robo receptor ectodomain polypeptide to be high affinity binding, and in some embodiments, binding of affinity greater than the affinity of Robo receptor ectodomain monomers for one another. Binding affinity is typically characterized by the dissociation constant ($K_D$) of the product of binding (e.g. Robo receptor dimer), with the binding affinity in an inverse relationship to the dissociation constant.

Thus, in some embodiments, binding of the agent (or moiety) to the Robo receptor ectodomain polypeptide is characterized by a dissociation constant in the micromolar and sub-micromolar range (i.e. $K_D$=10 microM to 1 pM). In particular embodiments, binding of the agent (or moiety) to the Robo receptor ectodomain polypeptide is characterized by a dissociation constant in the range of 1 nM-10000 nM, 5 nM-8000 nM, 10 nM-5000 nM, 15 nM-4000 nM, 20 nM-2000 nM, 25 nM-1000 nM, 10 nM-500 nM, 15 nM-400 nM, 20 nM-300 nM, 25 nM-200 nM, 25 nM-100 nM and 25 nM-150 nM. In some embodiments, binding of the agent (or moiety) to the Robo receptor ectodomain polypeptide is characterized by a dissociation constant of about 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 85 nM, 90 nM, 95 nM, 100 nM, 105 nM, 110 nM, 115 nM or about 120 nM. In a specific embodiment, binding of the agent (or moiety) to the Robo receptor ectodomain polypeptide is characterized by a dissociation constant in the range of 10-100 nM.

In other embodiments, the agent or moiety is an antibody binding to a Robo receptor D3 or D4 ectodomain polypeptide, the antibody being characterized by a dissociation constant in the range of 100-250 nM. In a specific embodiment, binding of the agent (or moiety) to the Robo receptor ectodomain polypeptide is characterized by a dissociation constant in the range of 10-200 nM, more particularly, a dissociation constant of 150-200 nM, or a dissociation constant of 180 nM. In specific embodiments, the agent or moiety is a Fab antibody fragment binding to a Robo receptor D3 or D4 ectodomain polypeptide, characterized by a dissociation constant in the range of 100-250 nM, more particularly, a dissociation constant of 150-200 nM, or a dissociation constant of 180 nM.

Each of the upregulating or downregulating agents described hereinabove can be administered to the individual per se or as part of a pharmaceutical composition which also includes a physiologically acceptable carrier. The purpose of a pharmaceutical composition is to facilitate administration of the active ingredient to an organism.

The term "agent" as used herein in reference to a Robo inhibitor means any compound or substance such as, but not limited to, a small molecule, nucleic acid, polypeptide, peptide, drug, ion, etc. An "agent" can be any chemical, entity, or moiety, including, without limitation, synthetic and naturally-occurring proteinaceous and non-proteinaceous entities. In some embodiments of the aspects described herein, an agent is a nucleic acid, a nucleic acid analogue, a protein, an antibody, a peptide, an aptamer, an oligomer of nucleic acids, an amino acid, or a carbohydrate, and includes, without limitation, proteins, oligonucleotides, ribozymes, DNAzymes, glycoproteins, antisense RNAs, siRNAs, lipoproteins, aptamers, and modifications and combinations thereof etc. Compounds for use in the therapeutic compositions and methods described herein can be known to have a desired activity and/or property, or can be selected from a library of diverse compounds, using screening methods known to one of ordinary skill in the art.

In some embodiments, the agents and/or moieties of the invention can be used for treatment of a Robo receptor-associated disorder or condition. Robo-associated conditions include, but are not limited to fibrotic conditions and disorders, cancerous conditions, orthopedic conditions and neurological conditions.

As used herein, neurological disorders include, but are not limited to Alexander disease, Alpers' disease, Alzheimer's disease (AD), amyotrophic lateral sclerosis, ataxia telangiectasia, Canavan disease, Cockayne syndrome, corticobasal degeneration, Creutzfeldt-Jakob disease, Huntington disease, Kennedy's disease, Krabbe disease, Lewy body dementia, Machado-Joseph disease, multiple sclerosis, PD, Pelizaeus-Merzbacher disease, Pick's disease, primary lateral sclerosis, Ref sum's disease, Sandhoff disease, Schilder's disease, Steele-Richardson-Olszewski disease, tabes dorsalis, frontal temporal dementia, vascular dementia, Down's syndrome, and Guillain-Barre Syndrome.

In some embodiments, the neurological disorder is a proteopathy (e.g., a synucleinopathy, AD, Alexander disease, amyotrophic lateral sclerosis (ALS), a prion disease (e.g., Creutzfeldt-Jakob disease), Huntington's disease, Machado-Joseph disease, Pick's disease, or frontotemporal dementia). In some embodiments of any of the foregoing methods, the neurological disorder is a synucleinopathy such as Parkinson's disease (PD), dementia with Lewy bodies, pure autonomic failure, multiple system atrophy, incidental Lewy body disease, pantothenate kinase-associated neurodegeneration, Alzheimer's disease, Down's Syndrome, Gaucher disease, or the Parkinsonism-dementia complex of Guam. In some embodiments of any of the foregoing methods, the neurological disorder is a progressive neurodegenerative disorder (e.g. Alpers' disease, ataxia telangectsia, Canavan disease, Cockayne syndrome, corticobasal degeneration, Kennedy's disease, Krabbe disease, Pelizaeus-Merzbacher disease, primary lateral sclerosis, Refsum's disease, Sandhoff disease, Schilder's disease, Steele-Richardson-Olszewski disease, tabes dorsalis, vascular dementia, or Guillain-Barre Syndrome). In some embodiments of any of the foregoing methods, the neurological disorder is an ApoE-associated neurodegenerative disorder (e.g., AD, vascular cognitive impairment, cerebral amyloid angiopathy, traumatic brain injury, or multiple sclerosis).

In other embodiments, the neurological condition is a traumatic injury or the results thereof, e.g. injured or damaged neural tissue. As used herein, the terms "injured" and "damaged" refer not only to a disrupted physical state of the neural tissue, but also to a disrupted functional state of the neural tissue, which may appear anatomically sound but suffer from absent or improper (excess or limited) neural transmission and/or signaling. In some embodiments, the neural injury or damage can be caused by a condition such as peripheral nerve injury or neuropathy (traumatic nerve injury, lower motor neuron lesion, demyelinating disease, diabetic neuropathy, and the like), cranial or cerebral trauma, aneurysm, spinal cord injury, stroke and disease. In a specific embodiment, the subject is suffering from traumatic brain injury (TBI). In some embodiments, the traumatic brain injury is a blunt trauma to the brain. In other embodiments, the traumatic brain injury is a cortical injury or cortical wound.

As used herein, orthopedic disorders or conditions include any acute, chronic, traumatic, and overuse injury or disorder of the musculoskeletal system. Orthopedic disorders or conditions that suitable for treatment using the present invention or methods include orthopedic joint disorders including hip, knee, shoulder, ankle, elbow, wrist, toe, finger, sacro-iliac, and spinal facet joint disorders.

In other embodiments, the present invention or methods can be used in the treatment of patients to prevent, delay, postpone, reduce, eliminate, or improve the outcome of surgery, e.g., orthopedic surgery, such as knee arthroscopy and meniscectomy, shoulder arthroscopy and decompression, carpal tunnel release, knee arthroscopy and chondroplasty, removal of support implant, knee arthroscopy and anterior cruciate ligament reconstruction, knee replacement, knee arthroscopy repair of both menisci, hip replacement, shoulder arthroscopy/distal clavicle excision, repair of rotator cuff tendon, fracture repair (including femoral neck fracture, femoral shaft fracture, trochanteric fracture, ankle fracture (e.g., bimalleolar type and fibula type), bone/ulna fracture, and distal part of radius fracture), bone grafting, hand surgery, and sports' medicine surgeries.

As used herein, the term "bone loss" includes a decrease in both mineral content and protein matrix components of the bone, and leads to an increased fracture rate of the femoral bones and bones in the forearm and vertebrae predominantly. These fractures, in turn, lead to an increase to general morbidity, a marked loss of stature and mobility, and in many cases, an increase in mortality resulting from complications. A number of bone growth disorders are known which cause an imbalance in the bone remodeling cycle. Chief among these are metabolic bone diseases, such as osteoporosis, rickets, osteomalacia, chronic renal failure and hyperparathyroidism, which result in abnormal or excessive loss of bone mass (osteopenia). Other bone diseases, such as Paget's disease, also cause excessive loss of bone mass at localized sites.

Fibrotic diseases effect many tissues within the body as a result of inflammation or damage. Tissues that can be effected by fibrotic diseases include those of the bone marrow, gallbladder, blood vessels, heart, joints, kidney, liver, lung, muscle, pancreas, penis, skin, soft tissue, eye, adrenal glands, thyroids and/or uterus. As used herein, exemplary fibrotic conditions include, but are not limited to aberrant wound healing, acute interstitial pneumonitis, arthrofibrosis, asthma, atherosclerosis, bone-marrow fibrosis, cardiac fibrosis, chronic kidney disease, cirrhosis of gallbladder, cirrhosis of liver, colloid and hypertrophic scar, Crohn's disease, cryptogenic organizing pneumonia, cystic fibrosis, desquamative interstitial pneumonia, diffuse parenchymal lung disease, Dupuytren's contracture, endomyocardial fibrosis, fibrosis as a result of Graft-Versus-Host Disease (GVHD), glomerulonephritis, idiopathic interstitial fibrosis, interstitial lung disease, interstitial pneumonitis, keloid scar, hypertrophic scar, liver fibrosis, lymphocytic interstitial pneumonia, morphea, multifocal fibrosclerosis, muscle fibrosis, myelofibrosis, nephrogenic systemic fibrosis, nonspecific interstitial pneumonia, organ transplant fibrosis, pancreatic fibrosis, Peyronie's disease, pulmonary fibrosis, renal fibrosis, respiratory bronchiolitis, retroperitoneal fibrosis, scarring after surgery, scleroderma, subepithelial fibrosis, or uterine fibrosis.

As used herein, the phrases "cancer", "malignancy", "solid tumor" or "hyperproliferative disorder" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancerous" or "malignant cell" or "solid tumor cell" is understood as a cell having specific structural properties, lacking differentiation and being capable of invasion and metastasis. "Cancer" refers to all types of cancer or neoplasm or malignant tumors found in mammals, including carcinomas and sarcomas. Examples are cancers of the breast, lung, non-small cell lung, stomach, brain, head and neck, medulloblastoma, bone, liver, colon, genitourinary, bladder, urinary, kidney, testes, uterus, ovary, cervix, prostate, melanoma, mesothelioma, sarcoma, (see DeVita, et al., (eds.), 2001, Cancer Principles and Practice of Oncology, 6th. Ed., Lippincott Williams & Wilkins, Philadelphia, Pa.; this reference is herein incorporated by reference in its entirety for all purposes).

"Hyperproliferative disease" refers to any disease or disorder in which the cells proliferate more rapidly than normal tissue growth. Thus, a hyperproliferating cell is a cell that is proliferating more rapidly than normal cells.

"Neovascularization" and "angiogenesis" refer to the growth of new blood vessels. Pathological angiogenesis or neovascularization refers to unbalanced new blood vessel growth, including non-self-limiting endothelial and periendothelial cell-proliferation. "Angiogenic diseases" are conditions of unregulated angiogenesis, for example, cancer, ocular neovascularization, arthritis, diabetes, skin diseases, chronic inflammatory diseases such as rheumatoid arthritis, psoriasis and synovitis.

"Advanced cancer" means cancer that is no longer localized to the primary tumor site, or a cancer that is Stage III or IV according to the American Joint Committee on Cancer (AJCC).

"Well tolerated" refers to the absence of adverse changes in health status that occur as a result of the treatment and would affect treatment decisions.

"Metastatic" refers to tumor cells, e.g., human solid tumor or thyroid malignancy, that are able to establish secondary tumor lesions in the lungs, liver, bone or brain of immune deficient mice upon injection into the mammary fat pad and/or the circulation of the immune deficient mouse.

A "solid tumor" includes, but is not limited to, sarcoma, melanoma, carcinoma, or other solid tumor cancer. "Sarcoma" refers to a tumor which is made up of a substance like the embryonic connective tissue and is generally composed of closely packed cells embedded in a fibrillar or homogeneous substance. Sarcomas include, but are not limited to, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

"Melanoma" refers to a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, metastatic melanoma, nodular melanoma, subungal melanoma, and superficial spreading melanoma.

"Carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidernoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma viflosum.

Additional cancers include, for example, Leukemia, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, papillary thyroid cancer, neuroblastoma, neuroendocrine cancer, esophageal cancer, genitourinary tract cancer, malignant hypercalcemia, cervical cancer, endometrial cancer, adrenal cortical cancer, and prostate cancer.

In specific embodiments, Robo-associated conditions can be used to treat or prevent or ameliorate chronic kidney disease and proteinuria, liver fibrosis, ocular-neo-vascular disorders, spinal cord injuries, tumor angiogenies, loss of bone mass, metastases and tumor or tumor-related fibers or tumor fibrosis.

Treatment with the agent and/or moiety of the invention comprises, inter-alia, administering the agent and/or moiety to a subject in need thereof. The agents and/or moieties of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agent and/or moiety accountable for the biological effect. Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method. Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch. The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents. Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions. Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (e.g. anti-D4-D4 antibody) effective to prevent, alleviate or ameliorate symptoms of a disorder (e.g., kidney fibrosis) or prolong the survival of the subject being treated. Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide the subject or patient, or lesions with levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease. As used herein, the term "subject" includes mammals, preferably human beings at any age which suffer from the pathology. Preferably, this term encompasses individuals who are at risk to develop the pathology.

As used herein the phrase "treatment regimen" refers to a treatment plan that specifies the type of treatment, dosage, schedule and/or duration of a treatment provided to a subject in need thereof (e.g., a subject diagnosed with a pathology). The selected treatment regimen can be an aggressive one which is expected to result in the best clinical outcome (e.g., complete cure of the pathology) or a more moderate one which may relief symptoms of the pathology yet results in incomplete cure of the pathology. It will be appreciated that in certain cases the more aggressive treatment regimen may be associated with some discomfort to the subject or adverse side effects (e.g., a damage to healthy cells or tissue). The type of treatment can include a surgical intervention (e.g., removal of lesion, diseased cells, tissue, or organ), a cell replacement therapy, an administration of a therapeutic drug (e.g., receptor agonists, antagonists, hormones, chemotherapy agents) in a local or a systemic mode, an exposure to radiation therapy using an external source (e.g., external beam) and/or an internal source (e.g., brachytherapy) and/or any combination thereof. The dosage, schedule and duration of treatment can vary, depending on the severity of pathology and the selected type of treatment, and those of skills in the art are capable of adjusting the type of treatment with the dosage, schedule and duration of treatment.

In some embodiments of these methods and all such methods described herein, the method further comprises administering to the subject an additional therapeutic agent, in addition to the Robo receptor ectodomain binding agent and/or moiety of the invention. Such an additional therapeutic agent can be co-administered with the Robo receptor ectodomain binding agent and/or moiety. As used herein, the phrase "co-administering" or to "co-administer" means the administration of a Robo receptor ectodomain binding agent and/or moiety described herein and another compound, e.g., a therapeutic agent, separately, simultaneously, and/or sequentially over a period of time as determined by a qualified care giver. Additional compounds or therapeutic agents suitable for use with the methods of the invention include, but are not limited to antifibrotic agents, anti-cancer agents, drugs and treatments for renal and hepatic conditions and hypertension.

In some embodiments of the invention, there is provided a method of identifying an agent for inhibiting Robo receptor activation comprising contacting candidate agents with a Robo receptor ectodomain polypeptide comprising a Robo receptor Immunoglobulin-like domain 3 (D3), Robo receptor Immunoglobulin-like domain 4 (D4), a Robo receptor Immunoglobulin-like domain 5 (D5), a Robo receptor Fibronectin type III domain 1 (FnIII-1)(D6), a Robo receptor Fibronectin type III domain 2 (FnIII-2)(D7) and a Robo receptor Fibronectin type III domain 3 (FnIII-3)(D8), a Robo receptor ectodomain D4-D5 linker sequence, a Robo receptor ectodomain D5-D6 linker sequence, a Robo receptor ectodomain D6-D7 linker sequence, a Robo receptor ectodomain D7-D8 linker sequence and the juxtamembrane segment sequence linking Robo receptor domain D8 and the transmembrane domain or a portion thereof and selecting candidate agents capable of binding to said polypeptide or portion thereof with a sub-micromolar dissociation constant. In some embodiments, identifying the agent comprising selecting candidate agents binding to a Robo receptor ectodomain D4 dimerization interface with a sub-micromolar dissociation constant. In specific embodiments, the binding is characterized by a dissociation constant in the range of 10-250 nM. In yet further embodiments, identifying the agent further comprises selecting candidate agents capable of inhibiting Robo receptor dimerization.

Robo receptor ectodomain binding agents and/or moieties for use in the compositions and methods described herein can be identified or characterized using methods known in the art, such as protein-protein binding assays, biochemical screening assays, immunoassays, and cell-based assays, which are well known in the art, including, but not limited to, those described herein in the Examples. For example, to identify a molecule that inhibits dimerization between Robo receptor ectodomains, immobilized or solution-based D3-D3, D4-D4 or D3-D3/D4-D4 binding assays can be used. Cell-based or membrane-based assays can also be used to identify molecules that inhibit dimerization between Robo receptor ectodomains. In some embodiments, the cell-based assay is a cKIT chimera-transphosphorylation assay or a neural cell (DRG) growth cone collapse assay. Such a molecule that inhibits dimerization between Robo receptor ectodomains can further be tested using in vivo animal models of chronic kidney disease, such as glomerular and interstitial injury models, models of cancer and metastatic disease, and models of fibrotic disease.

As used herein the term "about" refers to ±10%.

The terms "comprises", "comprising", "includes", "including", "having" and their conjugates mean "including but not limited to".

The term "consisting of" means "including and limited to".

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" ($8^{th}$ Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1, 2, 317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Experimental Procedures hRobo2 Receptor Ectodomain D4-D5 Fragment Subcloning:

Human Robo2 D4-5 (residues 311-509) was amplified from the complete cDNA of human Robo2. The insert was ligated into a modified pFastBac® (pK503-9) insect cell expression vector containing an N-terminal FLAG tag and a C-terminal hexahistidine tag, followed by a stop codon, as in (Opatowsky et al., 2014). To eliminate N-linked glycosylation that may hamper crystallization, Asn426, which is predicted to undergo glycosylation, was replaced with a methionine (N426M) using single assembly PCR.

hRobo2 Receptor Ectodomain D4-D5 Fragment Expression and Purification:

Baculovirus expressing WT hRobo2 D4-5 and the mutants (F357R and L394R) were prepared according to procedures described in the Bac-to-Bac® instruction manual (Invitrogen). Insect Sf9 cells were grown in 4 L culture of protein-free ESF 921 insect cell culture medium (Expression Systems) in spinner flasks, and incubated for 5 days post-infection. Growth medium with secreted hRobo2 receptor ectodomain D4-D5 fragment was concentrated and buffer-exchanged to 50 mM Tris, pH 7.6, 0.3 M NaCl and 10% glycerol using the QuixStand benchtop system. The concentrated and buffer-exchanged medium was then loaded onto a metal-chelate column (HisTrap, GE Healthcare) pre-equilibrated with buffer A (50 mM phosphate buffer, pH 7.4, 0.3 M NaCl, 10% glycerol) at a flow rate of 3 ml/min. The column was washed with buffer A until a stable baseline of background absorbance was achieved. hRobo2 receptor ectodomain D4-D5-containing fractions were eluted with a 70-200 mM imidazole gradient, pooled and loaded onto a preparative gel filtration column (Superdex 200 HiLoad 26/60, GE Healthcare), pre-equilibrated with buffer B (20 mM Hepes, pH 7.4, and 150 mM NaCl), for size exclusion chromatography. hRobo2 receptor ectodomain D4-D5-containing fractions were pooled and concentrated to 16 mg ml$^{-1}$ using a spin concentrator. The purified hRobo2 receptor ectodomain D4-D5 preparation was divided into aliquots and flash-frozen in liquid Nitrogen.

Crystallization, Data Collection, and Structure Determination—

Samples of hRobo2 receptor ectodomain D4-D5 at a concentration of 16 mg ml$^{-1}$ were screened for crystal growth conditions with the commercial crystallization screens Crystal Screen®, PegRX®, PEG/Ion®, and SaltRX® (Hampton Research) in 277 degrees Kelvin and 293 degrees Kelvin in 96-well hanging-drop clear polystyrene microplates (TTP LabTech) using the mosquito robot for crystallography (TTP LabTech). A 1:1 sample:reservoir ratio was used with a drop size of 0.2 µl. Small hexagonal crystals appeared after two weeks in 277K with a precipitant solution containing 2 M NaCl and 10% PEG 6000. Crystallization conditions were refined using 24-well hanging drop vapor-diffusion plates by varying the NaCl and PEG concentrations. Optimal crystal growth conditions were found to be 1.1 M NaCl and 11-13% PEG 6000. Crystals were harvested and flash-frozen with liquid Nitrogen after a cryo-protectant solution (15% PEG 6000, 5% glycerol, and 2 M NaCl) was gradually added to the crystallization drop. Diffraction data were measured at 100K on beamlines ID30-B (Zander et al., 2015) at the European Synchronotron (ESRF) and ID14.1 (Mueller U, 2012) at BESSY II, and were processed and scaled using the XDSAPP software package (Krug, 2012). Molecular replacement and initial model building were carried out using PHASER-MR, which placed the two Ig domains in the asymmetric unit. Further manual model building and refinement were performed using COOT (Emsley et al., 2010), Phenix-refine (Adams et al., 2010; Afonine et al., 2012), and the ReDo server (Joosten R P, 2012). Data collection and model statistics are summarized in Table 3:

TABLE 3

Summary of crystallographic statistics

| Data collection statistics | |
|---|---|
| Crystal hRobo2 D4-5 | |
| Beamline | ID-30B ESRF |
| Wavelength (Å) | 1.008 |
| Space group | I 41 2 2 |
| Unit Cell Parameters (Å) | a = b = 99.749, |
|  | c = 123.465, |
|  | α = β = γ = 90° |
| Total reflections[a] | 156736 (15623) |
| Unique reflections[a] | 12530 (1222) |
| Completeness (%)[a] | 100 (100) |
| $R_{meas}$ (%)[a,b] | 7.66 (167.5) |
| Mean I/σ[a] | 21.6 (1.47) |
| Resolution range (Å)[a] | 38.8-2.39 (2.48-2.39) |
| CC1/2[a] | 0.99 (0.62) |
| Refinement Statistics | |
| $R_{work}$ (%)[a] | 0.24 (0.38) |
| $R_{free}$(%)[a] | 0.27 (0.40) |
| mber of non-hydrogen ato | 1490 |
| Macromolecules | 1476 |
| Water | 24 |
| Protein residues | 198 |
| RMS bond lengths (Å) | 0.022 |
| RMS bond angles (°) | 1.94 |
| Ramachandran favored (%) | 94 |
| Ramachandran outliers (%) | 0.52 |
| Clashscore | 20.46 |
| Average B-factor | 77.86 |
| RCBS PDB code | 5NOI |

[a]Values for the highest resolution shell are given in parentheses
/$\Sigma_h \Sigma_i I_{h,i} | I_{h,i} - <I_h>_i |$
[b]$R_{meas} = \Sigma_h [m/(m-1)]^{1/2} \Sigma$ Analytical Ultracentrifugation—

All the sedimentation equilibrium experiments with hRobo2 receptor ectodomain D4-D5 constructs were performed using an XL-I analytical ultracentrifuge (Beckman-Coulter Inc.), with a UV-visible optics detection system, using an An60Ti rotor and 12-mm double sector centerpieces. Sedimentation curves were recorded and analyzed at 280 nm while spinning at 20° C. at 20,000 rpm in 10, 12, 14, and 20 hour time points, to assure that equilibrium was reached. Three concentrations (10, 20, and 30 µM) of WT hRobo2 receptor ectodomain D4-D5 (N426M) were measured. The F357R and L394R mutants were measured and analyzed in 20 µM. The molecular weight of WT hRobo2 receptor ectodomain D4-D5 fragment (N426M) was determined by mass spectroscopy using the Orbitrap Fusion Lumos with electron transfer dissociation (ETD), with both instrument and chromatography set up especially for the analysis of intact proteins. The recombinant protein includes an N' terminal FLAG and C' terminal 6XHis tags. Mass-Spectroscopy analysis revealed an additional 655 Da glycosylation, resulting in a total protein size of 24677 Da. Taking into account the glycosylation component, the partial specific volume ($\bar{v}$) of the glycoprotein was set at 0.722, as suggested in (Lewis and Junghans, 2000). The sedimentation coefficient distributions were calculated using SEDFIT and SEDPHAT (Gabrielson et al., 2007; Schuck et al., 2014).

Robo-cKit Chimera Phosphorylation Assay:

DNA subcloning—All constructs were prepared by PCR amplification from human Robo2 (accession no. BC146772.1) and human cKit (accession no. X06182.1). First, the PCR product of the full cKit (residues 33-976) and the intracellular c-Kit (IC-Kit, residues 514-976, including the transmembrane segment) were cloned into p3XFLAG-CMV™-10 Expression Vector (Sigma-Aldrich). For the hRobo2-cKit chimeras, hRobo2 receptor ectodomains D1-D3 (residues 22-312), hRobo2 receptor ectodomains D1-D4 (residues 22-413) and hRobo2 receptor ectodomains D1-D8 (residues 22-838) were amplified and cloned into IC-cKit-p3XFLAG-CMV™-10. The F357R mutations on hRobo2 receptor ectodomains D1-D4, 261SKAK (SEQ ID NO: 30) mutations on the hRobo2 receptor ectodomains D1-3 and hRobo2 receptor ectodomains D1-D8 were generated by Assembly PCR.

Cell Culture and Transfection—

HEK293 cells were maintained in Dulbecco's Modified Eagle's Medium (DMEM) supplemented with 10% fetal bovine serum (FBS), 2 mM 1-glutamine, 100 units/mL penicillin, and 100 µg/ml streptomycin, at 37° C., under 5% $CO_2$. For transfection, cells were seeded at 5×10$^4$ cells in a 6-well plate, cultured for 24 h, and transiently transfected with 5 µg DNA using a calcium phosphate-mediated transfection protocol. Transfected cells were incubated at 37° C., 5% $CO_2$ for 24 h.

In Vitro Phosphorylation Assay for cKit and Robo-cKit Chimeras—

Cells were serum-starved for 16 h, washed twice with PBS and solubilized in lysis buffer containing 120 mM NaCl, 25 mM Hepes (pH 7.4), 1 mM EGTA, 0.75 mM MgCl$_2$, 10% glycerol, 1% triton, 1 mM NaF, 2 mM sodium orthovanadate, protease inhibitor cocktail (Complete Mini EDTA-free, Roche). For the cKit positive control, the SCF ligand (expressed and purified as in Yuzawa et al., 2007) was added in a concentration of 2.5 ng/ml for 10 min at 37° C. before cell wash and lysis. Lysates were then immunoprecipitated with ANTI-FLAG® M2 Affinity Gel (Sigma-Aldrich) for 2 h at 4° C. After incubation, immunopellets were washed twice with 120 mM NaCl, 25 mM Hepes (pH 7.4), 1 mM EGTA, 0.75 mM MgCl$_2$, 10% glycerol, 0.1% triton, 2 mM sodium orthovanadate and analyzed by SDS/PAGE followed by immunoblotting with anti-flag M2 and antiphosphotyrosine antibodies (PY20, Biorad).

COS7 Collapse Assay:

hRobo2 DNA subcloning—All constructs were prepared by PCR amplification from the complete cDNA clone (Ima-Genes) of human Robo2 (Acc. no. BC146772.1). First, the PCR product of the full hRobo2 receptor (residues 1-1378) was cloned into the pEYFP-N1 plasmid (Clontech). The constructs hRobo2 receptor ectodomain D1-D4 (residues 1-410) and hRobo2 receptor ectodomain D1-D3 (residues 1-310) were generated by removing D5-D8 and D4-D8, respectively, using PCR mutagenesis. COS7 cells were maintained in Dulbecco's Modified Eagles Medium (DMEM) supplemented with 10% fetal bovine serum (FBS), 2 mM 1-glutamine, 100 units/mL penicillin and 100 m/ml streptomycin, at 37° C. under 5% CO2. For transfection, cells were seeded at 0.35×105 cells in a 24-well plate with a bottom coverslip, cultured for 24 h and transiently transfected with 300 ng DNA using TurboFect Transfection Reagent™ (Thermo Fisher Scientific). Transfected cells were incubated at 37° C. for 24 h, washed twice with phosphate-buffered saline (PBS) and fixed with 4% PFA. After fixation, cells were permeabilized with 0.1% Triton for 5 minutes and stained with Acti-Stain™ 670 phalloidin (ENCO) and bisBenzimide Hoechst (SIGMA-ALDRICH). Coverslips were dipped in distilled water and mounted on glass slides using Fluorescent Mounting Medium (GBI LABS). Images were obtained using Leica SP8 Confocal live microscope.

X-Ray Crystal Structure of hRobo2 D2-3 hRobo2 D2-3 Expression and Purification:

Baculovirus expressing hRobo2 D2-3 (residues 129-311 of SEQ ID NO: 1) were prepared according to procedures described in the Bac-to-Bac instruction manual (Invitrogen). Insect Sf9 cells were grown in 4 L culture of protein-free ESF 921 insect cell culture medium (Expression Systems, Davis, Calif.) in spinner flasks, and incubated for 5 days post-infection. Growth medium with secreted D2-3 was concentrated and buffer-exchanged to 50 mM Tris, pH 7.6, 0.3 M NaCl and 10% glycerol using the QuixStand benchtop system.

The concentrated and buffer-exchanged medium was then loaded onto a metal-chelate column (HisTrap, GE Healthcare) pre-equilibrated with buffer A (50 mM phosphate buffer, pH 7.4, 0.3 M NaCl, 10% glycerol) at a flow rate of 3 ml/min. The column was washed with buffer A until a stable baseline was achieved. After applying a 70-200 mM imidazole gradient elution, D2-3-containing fractions were pooled and loaded onto Superdex 200 HiLoad 26/60 (GE Healthcare), pre-equilibrated with buffer B (20 mM Hepes, pH 7.4, and 150 mM NaCl), for size exclusion chromatography. D2-3-containing fractions were pooled and concentrated to 19.5 mg ml$^{-1}$ using a spin concentrator. The purified D2-3 preparation was split into aliquots and flash-frozen in liquid N$_2$.

Crystallization, Data Collection, and Structure Determination—

Samples of D2-3 at a concentration of 19.5 mg ml$^{-1}$ were screened for crystal growth conditions with the commercial crystallization screens Crystal screen, PegRX, PEG/Ion, and SaltRX (Hampton Research, Aliso Viejo, Calif.) at 277K and 293K in 96-well hanging-drop clear polystyrene microplates (TTP LabTech, Hertfordshire, UK) using the mosquito robot for crystallography (TTP LabTech) with a 1:1 sample:reservoir ratio of 0.4 µl drops size.

Anti-hRobo2 D4 Dimerization Interface Antibodies and Antibody Fragments

Using isolated hRobo2 D4-5 (residues 311-509 of SEQ ID NO: 1, human Robo2) as the antigen, thirteen anti-Robo Fab antibody fragments were isolated from the Human Combinatorial Antibody Library (HuCAL) phage display library by BioRad AbD Serotec (Puchheim, Germany). The anti hRobo2 D4-5Fab antibodies were provided at 1 mg/ml concentration in preservative-free, endotoxin-free, phosphate buffered saline (PBS). Antibody Fab AbD32836.1 is encoded by SEQ ID NO: 35 (Fd chain with tags) and SEQ ID NO: 36 (Light chain).

Dorsal Root Ganglion (DRG) Growth Cone Collapse Assay

Explant culture DRG were dissected from E12.5 wild-type mice, and plated in 24-wells dishes coated with 10 ug/ml poly-d-lysine (Sigma-Aldrich, St Louis, Mo.) and 10 µg/ml mouse Laminin 1 (Sigma-Aldrich). DRGs were plated in serum-free Neurobasal medium supplemented with B27 (Gibco, Waltham, Mass.), penicillin-streptomycin solution, glutamine (Biological Industries, Beit HaEmek, Israel), and NGF (Alomone Labs, Jerusalem, Israel), and cultured overnight in a humidified incubator (37° C., 5% CO2).

Live Imaging—

E12.5 DRG explants were cultured for 12-18 h after plating. Differential interference contrast (DIC) videos were acquired on a real time cell history recorder (JuLI™ Stage, NanoEntek, Waltham, Mass.) under a humidified incubator (37° C., 5% CO2) environment. Images were acquired and controlled by JuLi™ software. For analysis of growth cone structure, images were acquired every minute. Quantification of growth cone area and growth cone retraction was characterized by manually outlining the growth cones.

Slit2N and antibodies were diluted in 20 mM Tris-HCl pH 8.8, 150 mM NaCl or 3*PBS respectively and added to the plate wells at a final concentration of 5 nM and 1 µM, respectively. Controls were performed to test whether the addition of the buffer would have an effect on growth cone motility. The antibodies and Slit2N were added either separately or sequentially.

Anti-hRobo2 Fab Binders Epitope Mapping

ELISA—

High binding flat-bottomed 96-well plates were coated with 1 µg Biorad-Antibodies in 50 mM bicarbonate buffer pH=9.6 (50 µL per well) and incubated overnight at 4° C. After washing 3 times with PBS, plates were blocked (PBS+3% skim milk powder) for 2 hours at RT with gentle shaking. The antigens (Flag-Robo2 Ig4-Ig5 WT, and the mutants F357R and L394R) were prepared at 200 nM in blocking buffer and added to the corresponding rows in duplicate. Plates were incubated for 90 min at RT and washed subsequently. Plates were incubated with 50 µL/well of anti-Flag HRP (1:4000 diluted in blocking buffer) for 60 min at RT. A final wash step was performed and plates were developed using TMB reagent (SouthernBiotech, Birmingham, Ala.) and 0.1M HCl stop solution. The optical density (OD) at 450 nm was read on an infinite 200 Pro (Tecan, Mannesdorf, Switzerland).

Molecular Graphics—

Molecular images were produced using PyMOL (see pymol dot sourceforge dot net).

Structure Deposition

The atomic coordinates and structure factors were deposited in the protein data bank (PDB) with the identification code 5N01.

EXPERIMENTAL RESULTS

Example 1: Expression, Purification and Crystallography of Human Robo2

Native hRobo2 receptor ectodomain D4-D5 was expressed in Sf9 cells, and purified to homogeneity from the buffer-exchanged growth medium using Ni-chelate and size exclusion chromatography. The purified protein was concentrated, flash-frozen in liquid N2, and screened for crystallization conditions. Since no crystallization conditions for native hRobo2 receptor ectodomain D4-D5 were identified, it was proposed that glycosylation of hRobo2 receptor ectodomain D4-D5 glycosylation may hamper crystallization. In order to evaluate the contribution of glycosylation to the difficulties encountered in crystallization, a predicted (Uniprot) glycosylation site on asparagine 426 ($^{426}$NQT) was substituted with a methionine. The hRobo2 receptor ectodomain D4-D5 N426M protein was expressed in a 3 L Sf9 cell culture suspension. Secreted hRobo2 receptor ectodomain D4-D5 N426M was buffer-exchanged, concentrated, and purified to homogeneity using Ni-chelate followed by size exclusion chromatography (FIG. 2), yielding a total of 12 mg purified protein. The protein was concentrated to 16 mg/ml, divided into aliquots, and flash-frozen in liquid Nitrogen. The concentrated hRobo2 receptor ectodomain D4-D5 N426M was screened for crystallization conditions using commercial sparse-matrix and grid screens in 96-well hanging-drop vapor-diffusion plates with a drop size of 400 nl (protein:precipitant ratio of 1:1). Small hexagonal crystals were detected in a drop containing 2 M NaCl and 10% PEG 6000 at 277K. Optimal crystal growth conditions consisted of a reservoir content of 1.1 M NaCl and 11-13% PEG 6000, with precipitant-to-protein ratios of 1:1 or 1:2 at 277K (FIG. 3). Crystals were gradually introduced to a cryo-protectant solution consisting of 15% PEG 6000, 5% glycerol, and 2 M NaCl that was added to the mother-liquor, and flash-frozen in liquid Nitrogen.

The crystals belonging to the 14122 space group, with unit cell dimensions of a=b=99.745 c=123.46 α=γ=β=90, have one molecule in the asymmetric unit, and a solvent content of 64%. The crystals diffracted to a maximal resolution of 2.25 Å (FIG. 4). We solved the crystal structure by standard molecular replacement using Phaser-MR (McCoy et al., 2007) with the first Ig domain of Obscurin (Pernigo et al., 2015) (PDB 4C4K) and the NMR solution of hRobo2 receptor ectodomain D5 h (PDB 2EDJ) as search models. Molecular replacement was followed by electron density modification procedures and cycles of model refinement and re-building using COOT (Emsley et al., 2010), PHENIX refine (Afonine et al., 2012), and the ReDo server (Joosten R P, 2012). The quality of the resulting electron density (FIG. 5) ensured correct assignment of all amino acid side chains.

Overall Crystal Structure of hRobo2 Receptor Ectodomain D4-D5

The crystal structure of hRobo2 receptor ectodomain D4-D5 (FIG. 6) shows that both the D4 and D5 ectodomains of hRobo2 receptor have an I-type Ig fold, each with strands AA'BB'DE on one beta sheet, and strands CFG on the opposite sheet. Di-sulfide bonds covalently link the two sheets at strands B and F in both D4 and D5 (Cys335 to Cys391 and Cys439 to Cys488, respectively), and 310 helices appear on the EF loop of both domains. A 7-residue-long coil ($^{410}$DVLTDRP, SEQ ID NO: 28) links the two domains that have no direct contact points and appear in a "beads on a string" arrangement. While the sequence of the D4-D5 linker is not conserved, the linker minimum length is preserved in all other Robo orthologs and paralogs—and includes at least six residues. It is, therefore, likely that the distancing and flexibility afforded by the D4-D5 linker serves a structural purpose that plays a role in the function of all Robo receptors.

hRobo2 Receptor Ectodomain D4-D5 Crystal-Contact Analysis

In order to elucidate possible biologically relevant interface areas between symmetry mates in the hRobo2 receptor ectodomain D4-D5 crystal lattice, the jsPISA server (Krissinel, 2015) was employed to obtain the total binding energy of each crystal contact, calculated from the total of hydrogen bonds, ionic, solvent-mediated, and hydrophobic interactions, as well as from the buried surface area of the interfaces. Analysis of the amino acid conservation landscape of the entire molecular surface of hRobo2 receptor ectodomain D4-D5 and of each one of the investigated interfaces against Robo paralogs and orthologs, including human, *drosophila*, nematode, and cnidaria sequences revealed four crystal contacts with a buried surface area greater than 100 Å$^2$. Of these, one interface stands out with the highest calculated total binding energy of −15.5 kcal/mol, and the lowest (that is, the strongest) hydrophobic P-value of 0.006. Critical residues of this hydrophobic interface are conserved throughout all the Robo homologs analyzed (FIG. 7). Interestingly, these include an Ig transmembrane receptor suspected to be a Robo ortholog from the *Radiata Exaiptasia pallida* (FIG. 7), supporting the hypothesis that Robo signaling is not restricted to bilateral creatures and precedes the emergence of Bilateria.

Example 1A

Expression, Purification and Crystallography of hRobo2 D2-3:

Expression of recombinant hRobo2 D2-D3 polypeptides was performed in a Baculovirus expression system (Invitrogen, Carlsbad, Calif.). Insect Sf9 cells were grown in cell culture medium (Expression Systems, Davis, Calif.) in spinner flasks, and incubated for 5 days post-infection. Growth medium with secreted D2-3 was concentrated and buffer-exchanged to 50 mM Tris, pH 7.6, 0.3 M NaCl and 10% glycerol using the QuixStand benchtop system.

Recovery and isolation of the secreted D2-3 polypeptides was performed in a metal-chelate column (HisTrap, GE Healthcare), washing with buffer until a stable baseline was achieved, and elution with a 70-200 mM imidazole gradient elution. The D2-3-containing fractions were pooled and further fractionated by size exclusion chromatography. D2-3-containing fractions were pooled and concentrated to 19.5 mg ml$^{-1}$ using a spin concentrator. The purified D2-3 preparation was split into aliquots and flash-frozen in liquid N$_2$.

Crystallization, Data Collection, and Structure Determination—

Samples of D2-3 at a concentration of 19.5 mg ml$^{-1}$ were screened for crystal growth conditions with the commercial crystallization screens as described in "Methods".

A single crystal that was formed under Peg/Ion screen well G4 was harvested and flash-frozen in liquid N$_2$. Diffraction data were measured at 100K on beamline ID14.2 then processed and scaled using the XDSAPP graphic interface for processing X-ray diffraction data sets.

The crystals belonging to the P212121 space group, with unit cell dimensions of a=62.224 b=70.524 c=97.274 α=γ=β3=90, have two molecules in the asymmetric unit, and diffracted to a maximal resolution of 2.46 Å. The crystal structure was solved by molecular replacement using the online BALBES molecular replacement server (Long et al., 2008). Molecular replacement was followed by electron density modification procedures and cycles of model refinement and re-building using COOT (Emsley et al., 2010), PHENIX refine (Afonine et al., 2012), and the ReDo server (Joosten R P, 2012). The quality of the resulting electron density ensures correct assignment of all amino acid side chains. The crystal structure refinement R/Rfree values are 25/28%.

From the crystal structures of hRobo2 D2-3 it can be discerned that the CD loops of D3 (D3 crystal structure shown in FIG. 12A) from the adjacent protomers are closely positioned to each other. The D3's CD loop includes both positive and negative residues that may form matching salt bridges, if positioned accurately (FIGS. 12B and 12C).

Example 2: Affinity and Specificity of the D4-D4 Dimer

The oligomeric state of hRobo2 receptor ectodomain D4-D5 in solution was determined by sedimentation equilibrium analytical ultracentrifugation (SE-AUC) (FIGS. 8A-8C). Three concentrations (10, 20, and 30 μM) of hRobo2 receptor ectodomain D4-D5 N426M were centrifuged at 10,000 rpm for 20 h, displaying a consistent monomer-dimer equilibrium in solution. The nonlinear least square fit to an ideal monomer-dimer model resulted in the determination of a dimerization dissociation constant ($K_D$) of 16.9±1.5 μM. Without wishing to ascribe to a single hypothesis, it is possible that, since unlike the soluble hRobo2 receptor ectodomain D4-D5 N426M, transmembrane Robo receptors are restricted to diffusion in two, rather than three dimensions and have less rotational freedom, it is expected that D4-mediated dimeric interactions of the intact receptors would be stronger than those observed in solution.

In order to explore structure-function relationships in the region of hRobo2 receptor ectodomain D4-D5, the dimer hydrophobic interface was mutated in two distal positions: either in F357R or L394R (FIGS. 8B and 8C, respectively). SE-AUC measurements of the mutants, conducted under similar conditions as the non-mutated hRobo2 receptor ectodomain D4-D5, show an exclusive monomeric form of the mutants (FIGS. 8B and 8C, and FIG. 9), confirming the specificity of the D4-D4 dimerization interface interaction, and ruling out the existence of strong, secondary oligomerization interactions in hRobo2 receptor ectodomain D4-D5.

D4-D4 Dimerization in Transmembrane Robo Receptors

In order to validate D4-D4 Robo-mediated dimerization in cells, a dimerization assay of chimera proteins consisting different constructs of the ectodomain of Robo1, 2, and 3, fused to the transmembrane and intracellular portions of the receptor tyrosine kinase (RTK) cKit (FIGS. 10A-10F) was developed. cKit phosphorylation was chosen to detect oligomerization because cKit can phosphorylate a juxtapositioned neighboring cKit kinase domain, but not itself or a more distant neighbor. Using the hRobo2 receptor ectodomain RTK-cKit phosphorylation assay, the activity of several constructs and mutants of truncated hRobo1, 2, and 3 have been compared. Activity was assessed for hRobo2 receptor ectodomain D1-3, hRobo2 receptor ectodomain D1-D4, hRobo2 receptor ectodomain D1-D8, hRobo2 receptor ectodomain D1-D4 F357R, and hRobo2 receptor ectodomain D1-D8 F357R. For hRobo1, hRobo1 receptor ectodomain D1-D4 was evaluated. For hRobo3, hRobo3 receptor ectodomain D1-D3 and D1-D4 were evaluated.

The results show that hRobo2 receptor ectodomain D1-D4 construct has a higher level of phosphorylation than hRobo2 receptor ectodomain D1-D3, which confirms D4 as a dimerization domain. The lower level of phosphorylation of D1-D8 may be due to autoinhibition by domains D5-D8. A lower level of phosphorylation in the D1-D4 F357R, and D1-D8 F357R mutants in comparison to the corresponding non-mutated constructs further confirm the key role of D4 in dimerization. The phosphorylation data are consistent with the SE-AUC experiments, and demonstrate hRobo2 receptor ectodomain D4-mediated dimerization also in a transmembrane receptor setting in a cell culture system. These results also corroborate the crystallographic findings that D4 is a dimerization domain within the hRobo2 receptor ectodomain.

Linking Robo Dimerization and Signaling

These results establish that Robo receptors dimerize through D4. In order to evaluate the influence of Robo dimerization on cell morphology, several GFP-fused hRobo2 constructs were transiently expressed in COS—7 cells (FIGS. 11A-11C) and the effect on COS—7 cells size and the actin cytoskeleton structure was monitored.

In this "cytoskeleton collapse" cell assay, ectopic expression of repulsion receptors in commonly used cell lines results in visible outcomes to the morphology of the cell, for example, the "contraction phenotype" of COS—7 cells expressing a constitutively active mutant of PlxnA4, while the expression of WT PlxnA4 does not elicit a similar response (Kong et al., 2016).

The cells were fixed and stained 24 hours post-transfection, and the resultant effects on the cells observed using a fluorescent microscope.

Expression of hRobo2 receptor ectodomain D1-D4 in the COST cells resulted in a dramatic reduction in cells' surface area, in comparison to that of neighboring untransfected cells. hRobo2 receptor ectodomain D1-D4 F357R mutant, which shows reduced dimerization in the SE-AUC and cKit-Robo phosphorylation assays, has a weaker effect on COS—7 collapse. A hRobo2 receptor ectodomain D1-D4 construct missing the entire intracellular (IC) segment, which cannot recruit intracellular effector proteins and initiate downstream signaling events was expressed as a control. As expected, the hRobo2 receptor ectodomain D1-D4 no-IC construct had no effect on the morphology of the transfected COS—7 cells.

D4 Dimerization Antagonists: Anti-hRobo2 D4 Dimerization Interface Binders

Thirteen anti-hRobo2 D4-5 antibodies were isolated from the Human Combinatorial Antibody Library (HuCAL) phage display library, and antibodies specific for the dimerization interface were identified and purified.

Twelve of the thirteen anti-Robo Fab antibodies were screened for their ability to differentially bind to wild type vs. two hRobo2 D4-5 mutants in an ELISA binding assay.

The hRobo2 D4-5 mutants tested (F357R and L394R), both located at opposing sides of the D4 dimerization interface (see FIG. 6), have been shown to eliminate hRobo2 D4-5 dimerization in sedimentation equilibrium analytical ultracentrifugation (SE-AUC) (see FIGS. 8A-8C). In this way, differential binding of individual Fab to wild type (w.t.) hRobo2 D4-5 and mutants provides further evidence for overlapping between the Fab binding site and the D4 dimerization interface.

Six of the thirteen anti-Robo antibody Fabs showed partial or full differential binding. Of these, Fab AbD32836.1 binds well to the w.t. hRobo2 D4-5, with apparent $K_D$ value of 0.18 microM, but showed no association to either of the two mutants (F357R and L394R), thereby mapping its binding site to cover the entire D4 dimerization interface.

The anti-hRobo2 D1-D4 dimerization site Fab antibodies were than tested for their ability to inhibit hRobo2 D1-4 dimerization using the Robo:cKIT chimera trans-phosphorylation assay. Indeed, addition of 1:200 v/v anti-hRobo2 D1-D4 dimerization site antibody Fabs (FIG. 14, lanes D1-4+Ab36 ... D1-4+Ab41) to the growth culture media for overnight incubation reduced hRobo2 D1-4 dimerization, compared to the dimerization of untreated chimeras (FIG. 14, Lane NT), as evaluated by tyrosine phosphorylation (FIG. 14).

Anti-hRobo2 D1-D4 Dimerization Site Fab AbD32836.1 Inhibits hSlitN2 Activity in a Biological Assay To demonstrate the biological activity of Fab AbD32836.1, the Fab fragment was assayed for inhibition of hSlitN2 activation of the Robo pathway using the growth cone collapse assay. Rodent Dorsal Root Ganglions (DRG) expresses Robo2, and dish-cultured DRG explants show growth cone collapse and axon retraction responses to SlitN2 treatment (Hussain et al., 2006; McConnell et al., 2016; Piper et al., 2006; Seiradake et al., 2009; Yuasa-Kawada et al., 2009). Pre-treatment with 100 nM Fab #AbD32836.1, significantly reduced growth cone collapse from 60% to 14%, 10 min after 5 nM SlitN2 treatment (FIGS. 15A and 15B), confirming that blocking of the D4-D4 dimerization by a binding moiety specific for the D4-D4 dimerization interface (e.g. Fab #AbD32836.1) exerts a biological activity on endogenous tissue that is antagonistic to SlitN2 activation, consistent with inhibition of the Robo2 signal pathway.

Example 3: hRobo2 D3-D3 Dimerization in Transmembrane Robo Receptors

X-ray crystallographic data from hRobo1 1-4 supports the feasibility of D3-D3 dimerization at the D3 CD loop, presumably by salt bridge formation between adjacent oppositely charged residues (see FIGS. 12B and 12C). In order to evaluate the contribution of these residues to D3-D3 dimerization, the crystal structure of hRobo2 D2-3 was determined (FIG. 12A and above), and based on the new structural information, a mutated hRobo2 D1-3 (residues 22-312 of SEQ ID NO: 1) having inverted charges due to substitution of three of the aspartates in the hRobo2 D3 CD loop (SEQ ID NO: 18) with serine and lysine residues (261DDAD SEQ ID NO: 29 to SKAK, SEQ ID NO: 30) was designed. When the function of the mutated hRobo2 D1-3 was assessed in the hRobo2 receptor ectodomain RTK-cKit phosphorylation assay (FIG. 13), it was evident that the mutated hRobo2 D1-3 (FIG. 13, D1-3 261DDAD, SEQ ID NO: 29 to SKAK, SEQ ID NO: 30) exhibited only weak level of dimerization when compared to the non-mutated hRobo2 D1-3 protein, corroborating the crystallographic findings that D3 is also a dimerization domain within the hRobo2 receptor ectodomain, and demonstrating the importance of the D3 CD loop in hRobo2 dimerization (FIG. 13).

Taken together, the results presented herein clearly indicate that Robo receptor ectodomain D4 mediates Robo dimerization and signaling, and that compromising D4-mediated dimerization significantly and substantially diminishes Robo dimerization and signaling. Further, the identification of a secondary dimerization site at Robo receptor ectodomain D3 suggests an important contribution of D3 to Robo dimerization and signaling.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An antibody or a portion thereof specifically binding to a Robo2 receptor Immunoglobulin-like domain 4 (D4) dimerization interface and inhibiting Robo2 D4-D4 receptor dimerization, wherein said portion is a Fab antibody, wherein the light chain of said antibody is encoded by SEQ ID NO: 36 and the Fd chain of said antibody is encoded by SEQ ID NO: 35.

2. The antibody of claim 1, wherein said antibody does not bind any of Robo2 receptor D1 or D2.

3. The antibody of claim 1, wherein said antibody inhibits homo-dimerization of an isolated Robo receptor selected from the group consisting of an isolated Robo2 receptor D4-D5 polypeptide and an isolated Robo2 receptor D4 polypeptide.

4. The antibody of claim 1, wherein said binding is characterized by a dissociation constant ($K_D$) in the range of 10 nM-5000 nM.

5. The antibody of claim 4, wherein said binding is characterized by a dissociation constant in the range of 10-250 nM.

6. The antibody of claim 1, wherein said Robo2 receptor Immunoglobulin-like domain D4 dimerization interface comprises the amino acid sequence as set forth in SEQ ID NO: 31.

* * * * *